(12) United States Patent
Smith et al.

(10) Patent No.: US 9,176,094 B2
(45) Date of Patent: Nov. 3, 2015

(54) PERFORMANCE OF AN ANALYZER FOR BIOLOGICAL SAMPLES

(75) Inventors: Stan Smith, Phoenix, AZ (US); Brett Duane, Phoenix, AZ (US); Cedric Hurth, Tempe, AZ (US); David Nguyen, Phoenix, AZ (US); Amol Surve, Phoenix, AZ (US); Ralf Lenigk, Chandler, AZ (US); Frederic Zenhausern, Fountain Hills, AZ (US)

(73) Assignees: WHITESPACE ENTERPRISE CORPORATION, Fountain Hills, AZ (US); THE ARIZONA BOARD OF REGENTS, Scottsdale, AZ (US)

(*) Notice: Subject to any disclaimer, the term of this patent is extended or adjusted under 35 U.S.C. 154(b) by 0 days.

(21) Appl. No.: 13/819,411

(22) PCT Filed: Aug. 25, 2011

(86) PCT No.: PCT/US2011/049141
§ 371 (c)(1),
(2), (4) Date: Sep. 9, 2013

(87) PCT Pub. No.: WO2012/027567
PCT Pub. Date: Mar. 1, 2012

(65) Prior Publication Data
US 2013/0341191 A1    Dec. 26, 2013

Related U.S. Application Data

(60) Provisional application No. 61/377,831, filed on Aug. 27, 2010.

(51) Int. Cl.
*G01N 15/06* (2006.01)
*G01N 33/00* (2006.01)
(Continued)

(52) U.S. Cl.
CPC ........ *G01N 27/447* (2013.01); *B01L 3/502715* (2013.01); *G01N 35/00029* (2013.01); *H05K 1/11* (2013.01); *B01L 7/52* (2013.01);
(Continued)

(58) Field of Classification Search
USPC .......... 422/68.1, 81, 502, 503, 504, 509, 554; 436/43
See application file for complete search history.

(56) References Cited

U.S. PATENT DOCUMENTS 6,841,739 B2    1/2005    Moore

FOREIGN PATENT DOCUMENTS

| WO | WO 2006/103440 | 10/2006 |
|----|----------------|---------|
| WO | WO 2009/021240 | 2/2009  |
| WO | WO 2010/091410 | 8/2010  |

OTHER PUBLICATIONS

International Search Report and Written Opinion for International Application No. PCT/US2011/049141 mailed Nov. 11, 2011.

*Primary Examiner* — Brian J Sines
(74) *Attorney, Agent, or Firm* — Merchant & Gould P.C.

(57) ABSTRACT

An apparatus (11) for processing a sample, circuit board (8008) suited to use in such an apparatus and a method of processing are provided in which the apparatus (11) is provided with alignment features to assist in provided the circuit board and a sample cartridge (9) in the correct position relative to one another. In this way, the plurality of sections for processing a sample in the cartridge (9) are positioned against a plurality of elements, such as a heater (4) for heating the sample cartridge (9) or an electrical contact (EP1-EP4) for powering features on the sample cartridge (9), correctly and can operate independently of one another.

9 Claims, 32 Drawing Sheets

(51) Int. Cl.
- *G01N 33/48* (2006.01)
- *G01N 27/447* (2006.01)
- *B01L 3/00* (2006.01)
- *G01N 35/00* (2006.01)
- *H05K 1/11* (2006.01)
- *B01L 7/00* (2006.01)
- *B01L 9/00* (2006.01)

(52) U.S. Cl.
CPC ............ *B01L9/527* (2013.01); *B01L 2200/025* (2013.01); *B01L 2200/14* (2013.01); *B01L 2300/0816* (2013.01); *B01L 2300/1822* (2013.01); *B01L 2400/0475* (2013.01)

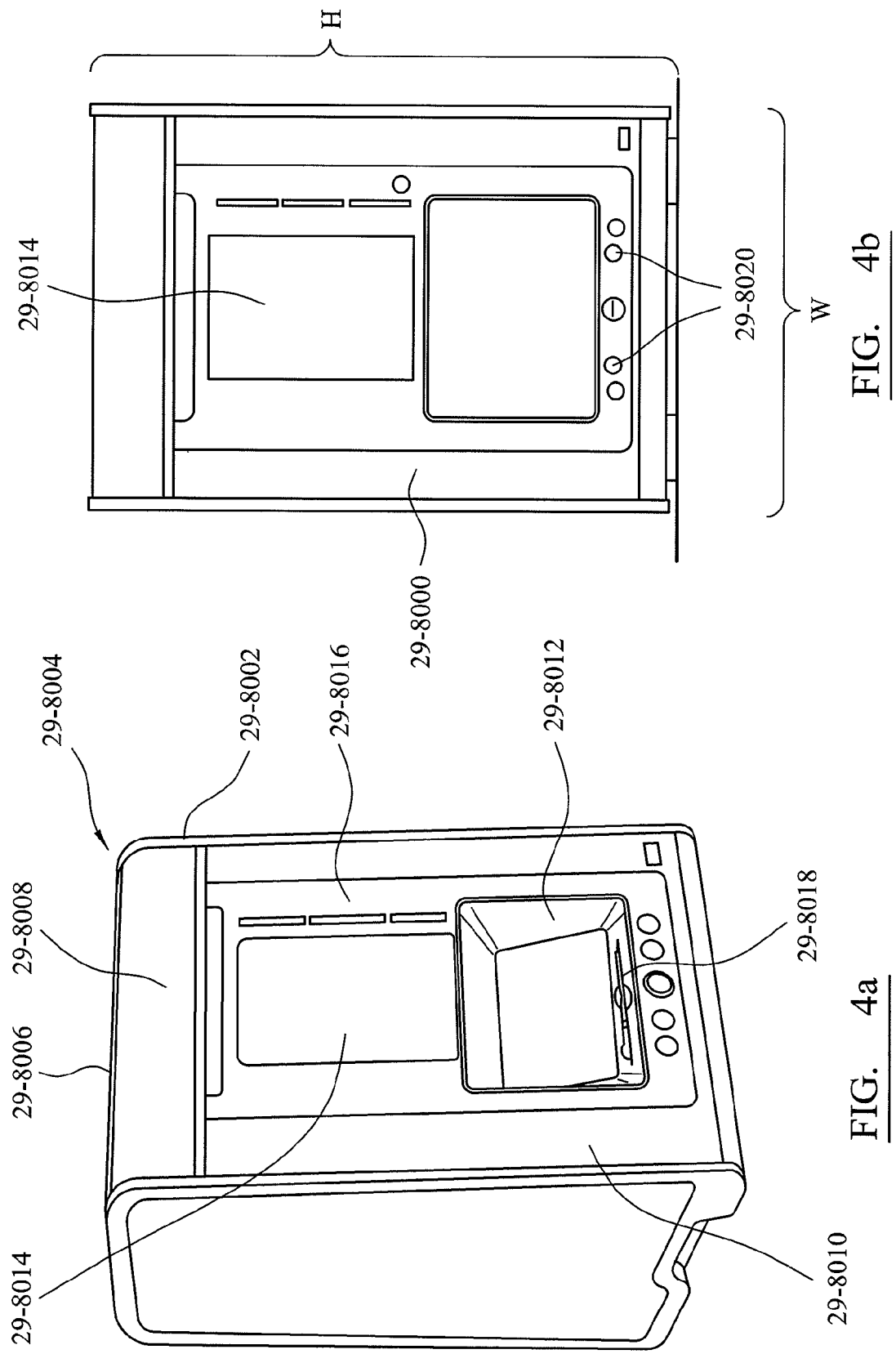

FIG. 11b

Design Specifications

Design Specification : fSS Buccal

| Functional Chambers | Volume | Depth | Tool | Vent | Note |
|---|---|---|---|---|---|
| C1 (Lysis) | 300ul total | 1mm | | | |
| C2 (Purification/Beads) | 311ul total | 0.75mm | | Yes | |
| Expansion Chamber | 67ul total | 0.75mm | | | |
| C3 (Dwell) | 250ul total | 0.5mm | | Yes | |
| C4 (Heating/Magnet) | 250ul total | 1.0mm | | Yes | |
| Bead Storage Chamber | 30ul total | 1.0mm | | Yes | |
| PCR Chamber | 23ul | 1.0mm | | | |
| Binding Buffer Chamber | 40ul total | 2.0mm | | Yes | |
| Auxiliary Chambers | | | | | |
| Elution | 150ul total | 2.0mm | | Yes | |
| Wash Buffer | 250ul total | 1.0mm | | No | |
| Recovery | 200ul | 2.0mm | | Yes | |
| EC Pump | 1124ul total | 2.0mm | | | |
| Waste | 1000ul total | 2.5mm | | Yes | |
| Channel | | | | | |
| Flow Channel | | 0.5mm | 0.5mm BEM | | |
| Pump Channel | | 0.5mm | 0.5mm BEM | | See A.N. |
| PCR Entrance Channel | | 1.0mm | 1.5mm BEM | | |
| Paraffin Valve | Diameter | | | | |
| Open Valve | 1.0mm | 0.5mm | | | |
| Close Valve | 2.0mm | 1.0mm | | | |
| Close Valve 12/13 | 3.0mm | 1.0mm | | | PCR Close valves enlarged |
| Cartridge Specification | | | | | |
| Height | 160mm | | | | |
| Width | 125mm | | | | |
| Thickness | 3.0mm | | | | |
| Electrode Glue | UV Glue | | | | |
| Alignment Pin | 2.3mm | | | | |
| Bonding Tape | 90106 | | | | |
| Fabrication Note | | | | | |
| Tape trimmed in chambers | | | | | |

| Functional Chambers | Volume | Depth | Tool | Vent | Note |
|---|---|---|---|---|---|
| C1 (Lysis) | 300ul | 1mm | Std Cutter | No | |
| C2 (Purification) | 311ul | 0.75mm | Std Cutter | Yes | |
| Expansion/Mixing Chambers | 67ul | 0.75mm | Std Cutter | No | |
| C3 (Dwell or Initial Binding)) | 250ul | 0.5mm | Std Cutter | Yes | |
| C4 (PCR washing and release) | 250ul | 1.0mm | Std Cutter | Yes | |
| Bead Storage (BSC) | 30ul | 1.0mm | Std Cutter | No | |
| Binding Buffer (BBC) | 40ul | 2.0mm | Std Cutter | No | |
| Elution | 150ul | 2.0mm | Std Cutter | No | |
| Wash Buffer | 250ul | 2.0mm | Std Cutter | No | |
| Archive | 200ul | 2.0mm | Std Cutter | No | |
| Waste | 1000ul | 2.5mm | Std Cutter | Yes | |
| PCR | 10ul | 1.0mm | Std Cutter | No | |
| Formamide | 105ul | 1.0mm | Std Cutter | No | |
| Denaturing | 105ul | 1.0mm | Std Cutter | No | |
| Channel | | | | | |
| PCR Red | | 0.25mm | 0.5mm BEM | | Sigma-Aldrich 411663 |
| PCR Cyan | | 1.0mm | 1.0mm BEM | | Sigma-Aldrich 411663 |
| PCR White/Black | | 0.35mm | 0.5mm BEM | | Saso:wax H1 |
| Magenta | | 0.5mm | 1.0mm BEM | | |
| EC PUMP Yellow | | 2.0mm | 1.0mm BEM | | |
| Paraffin Valve | Volume | Depth | Tool | | |
| LMW OV's 1.5mm diameter | 1.77ul | 0.5mm | Std Cutter | | |
| LMW OV's 3.0mm diameter | 7.1ul | 1.0mm | Std Cutter | | |
| HMWV CV15 | 7.1ul | 1.0mm | Std Cutter | | |
| Cartridge Specification | | | | | |
| Substrate width - 175mm | | | | | |
| Substrate length - 228mm | | | | | |
| Substrate 3.0mm PC | | | | | |
| Capping Layer 0.5mm PC | | | | | |
| PSA 90106 cold bond assy | | | | | Adhesives Research |
| EC pump UV glue 1180-M | | | | | |
| Bar Code pocket | N/A | 0.2mm | Std Cutter | | May opt for flduclai:marks instead |

FIG. 15b

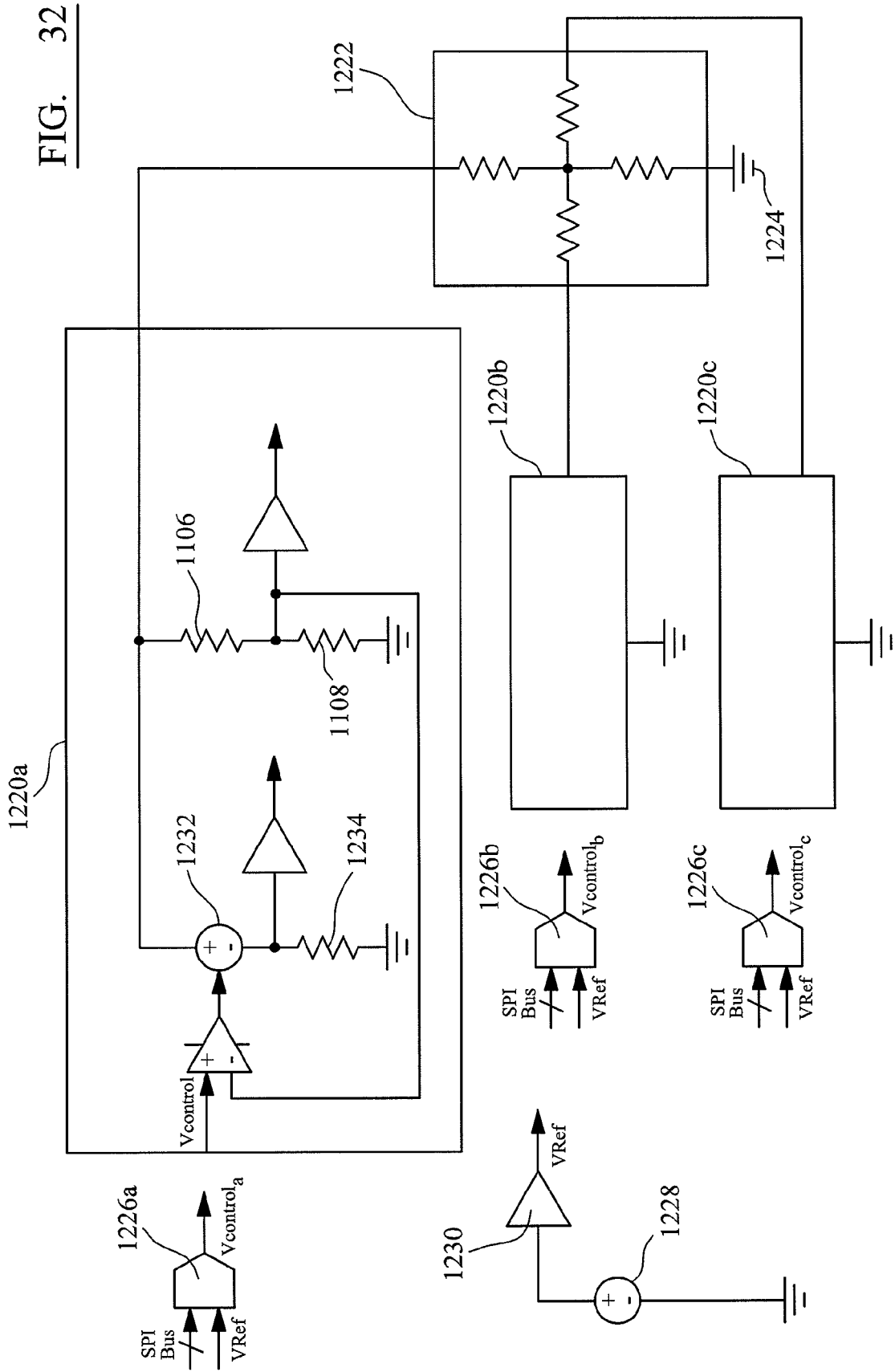

PERFORMANCE OF AN ANALYZER FOR BIOLOGICAL SAMPLES

This application is a National Stage Application of PCT/US2011/049141, filed 25 Aug. 2011, which claims priority to U.S. patent application Ser. No. 61/377,831 filed on 27 Aug. 2010, and which applications are incorporated herein by reference. To the extent appropriate, a claim of priority is made to each of the above disclosed applications.

BACKGROUND OF THE INVENTION

The invention concerns improvements in and relating to analysis, particularly, but not exclusively, in relation to biological samples.

Analysis of samples, for example biological samples, is known. However, such analysis typically involves many process steps, requires skilled operatives and is labour intensive. It would be desirable to at least partly automate the analysis. It would also be desirable to reduce the requirement for skilled operatives.

SUMMARY OF THE INVENTION

According to a first aspect of the invention, there is provided a circuit board for interfacing with a sample cartridge, wherein the sample cartridge comprises a working surface defining a plurality of sections for processing a sample; wherein the circuit board is configured to be adjacent the working surface in use and comprises:

a plurality of elements, each of the plurality of elements is associated with one of the plurality of sections and is arranged to be positioned adjacent the associated one of the plurality of sections in use; and wherein the circuit board further delimits at least one alignment feature for engaging a corresponding alignment feature on the cartridge and ensuring that the plurality of elements are positioned adjacent the associated one of the plurality of sections in use.

The elements can be passive or active. An example of an active component is a heater for heating the sample cartridge. An example of a passive component is an electrical contact for powering features on the sample cartridge, such as pumps.

According to this aspect of the invention, the automation of processing a sample is improved. The sample cartridge provides a plurality of sections and the circuit board enables these sections to be activated as required for processing the sample. The at least one alignment feature ensures that the features on the circuit board are aligned correctly with the corresponding features on the sample cartridge.

The circuit board may further comprise an edge delimiting an opening corresponding to a sample processing chamber on the sample cartridge. A sample processing chamber may require fine control over processing in the chamber. This may be provided by features separate from the circuit board. The opening allows access to the chamber by additional components that the circuit board as may be required.

The circuit board may further define a window allowing, in use, a feature of the working surface to be visually inspected through the circuit board. The window may be an opening delimited by an interior edge of the circuit board or a transparent section of the circuit board. The portion of the working surface of the sample cartridge adjacent the window may be visually inspected when the sample cartridge is installed in the apparatus. This is particularly advantageous if an identifier, such as a bar code is printed on the portion of the sample cartridge adjacent the window.

The circuit board may further comprise projections extending from its surface in a direction such that, in use, they are directed towards the cartridge. The projections are conductive to allow an electrical current to be supplied to the sample cartridge through the projections.

The projections may have sharp tips. This can help in penetrating any oxide layer that may have formed on a corresponding portion of the sample cartridge.

The projections may be resiliently mounted. For example they may be spring loaded so that when a sample cartridge is installed in the apparatus a force is applies to the projections to bias them towards the sample cartridge and improve the electrical contact. In one embodiment the projections may be pogo pins.

In a related aspect, an apparatus for analyzing a sample provided in a sample cartridge comprises a circuit board as discussed above (with or without one or more of the optional features also discussed above). At least part of a section for receiving the sample cartridge may be mounted with a resilient element for providing a force to press the circuit board and the working surface of the sample cartridge together in use. Alternatively, the apparatus may comprise a platen for acting against a non-working surface of the sample cartridge and the platen may be moved to press the working surface of the sample cartridge against the circuit board. This can enhance the electrical contact between the circuit board and the sample cartridge. The sample cartridge may be placed in a holder before being inserted to the apparatus.

A common requirement when processing a sample is to provide reliable heating of the sample. This can be difficult when several processing steps are automated using a sample cartridge because reliable, localized heating is required. It would therefore be desirable to provide a reliable localized heater assembly.

According to another aspect of the invention, there is provided a resistive heater assembly comprising:

a circuit board; and a resistive heating element mounted on the circuit board having a substantially flat upper surface;

wherein in use the substantially flat upper surface is arranged to be substantially in contact with a item to be heated.

It has been found that a resistive heating element provides reliable heating and the resistive nature means that the heat generated can be accurately and simply controlled. In order to ensure that the heat generated is directed to a specific area to be heated, the resistive heating element has a substantially flat surface for contacting the area to be heated. This allows control over the area to be heated by controlling the area of the substantially flat upper surface.

The resistive heating element may have a surface coating. The surface coating can improve the physical properties of the substantially flat upper surface. For example, it may provide protection to the heating element, or improve the contact with the item to be heated. Preferably, the surface coating is flexible to improve contact, for example it may be formed from silicone.

The resistive heating element is preferably soldered to the circuit board with a solder configured to have a melting point greater than 450° C. Preferably, the solder is a lead-free solder composition. The heating element may reach local temperatures that melt conventional solders. Preferably, the solder comprises silver and has a melting point of 680° C. or higher.

Advantageously, the resistive heating element may comprise at least one surface mount resistor. Surface mount resistors have been found to be well suited to use as heater, they have a suitable substantially flat upper surface and can be attached to a circuit board using known techniques. The choice of type and number of resistors depends on the area to be heated and the temperature to be achieved. This will determine the required power input that the surface mount resistor must handle.

The assembly may further comprise a temperature sensor for sensing the temperature of the resistive heating element. The temperature sensor allows use of feedback control to determine the temperature of heating.

Preferably, the temperature sensor is located in a recess formed on the circuit board. This allows it to be located close to the heating element to provide a more accurate measurement of temperature.

In a related aspect, an apparatus for analyzing a sample provided in a sample cartridge is provided. The apparatus comprises a resistive heating assembly as discussed above (with or without one or more of the optional features also discussed above). The heating assembly allows reliable localized heating of a portion of the sample cartridge.

The accuracy of an automated heating step during processing of a sample can be improved through feedback control. In order to provide accurate feedback control, it is desirable to have an accurate temperature measurement of the heater.

Accordingly, in a further aspect of the invention, a temperature sensor is provided for sensing the temperature of a resistive heating element, the temperature sensor comprises:
 a bridge circuit comprising first and second arms;
 a thermistor for sensing the temperature of a resistive heating element connected in one arm of the bridge circuit; and
 an ADC connected between the first and second arms of the bridge circuit for digitizing the voltage difference across the first and second arms of the bridge.

The resistance of the thermistor changes according to the temperature, altering the voltage balance across the arms of the bridge circuit. Preferably, the ADC is a differential ADC to allow direct measurement across the bridge circuit. The thermistor is preferably positioned close to the resistive heating element, for example within a few millimeters, more preferably within 5 mm, of the center of a heating surface to ensure as accurate a measurement as possible. A heating surface may comprise more than one heating element arranged as a group, for example a group of surface mount resistors. In that case the center of the heating surface formed by the group of heating elements gives the most representative temperature. The thermistor may be positioned in a recess formed in a PCB, this is particularly advantageous when the sensor of this aspect is used with the above described resistive heater assembly.

The sensor may further comprise a voltage source which is connected as a reference for the bridge circuit and as a power supply for the ADC. This simplifies the construction of the sensor.

In use, the power dissipation in the thermistor is preferably less than 10 µW. This power dissipation may be achieved through choice of voltage and/or of the bridge components, for example the resistance of elements of the bridge. By keeping the power dissipation low, the influence of any resistive heating from the thermistor on the temperature to be measured is reduced.

Preferably, a predetermined number of the most significant bits output from the ADC may be used. For example the ADC may produce an output with a predetermined number of bits, but less than the predetermined number of bits are used. This can improve the accuracy of measurement, because variation in the least significant bits is ignored, reducing the susceptibility to errors. For example, only the most significant 14 bits of a 22 bit ADC may be used. Other choices may be used in alternative embodiments.

In a related aspect, an apparatus for analyzing a sample provided in a sample cartridge is provided, wherein the apparatus comprises a resistive heating assembly and a temperature sensor as discussed above (with or without one or more of the optional features).

It is desirable to provide accurate control of heating in sample processing. In particular it is desirable to control heating so that the desired temperature is achieved as quickly as possible, but without overshoot. While conventional control techniques, including proportional, integral and derivative control can provide a good response, it would be desirable to further reduce the time taken to reach a desired temperature.

Accordingly, in another aspect of the invention, a method of generating a signal for controlling the temperature of a resistive heating element using feedback control is provided, wherein an error signal value used in the feedback control is adjusted if the absolute value of the error signal value is greater than 1.

If the absolute value of an error signal is greater than 1, this indicates that the actual temperature is still some way from the desired temperature. In order to reach the desired temperature as quickly as possible, the error signal is adjusted. Preferably the error signal is amplified, for example by applying a gain to the error signal.

Preferably, if the absolute value of the error signal value is greater than 1, the error signal value is adjusted by squaring the error signal value and applying the sign of the error signal value to the result. This ensures that the greater the error the greater the compensation that is applied to it, so that the actual temperature should reach the desired temperature quicker. As the temperature approaches the desired temperature, the error signal reduces and the impact of the squaring reduces, smoothly reducing the effect for smaller errors.

The output of the method may be a PWM signal, and the method may further comprise setting the signal for controlling the temperature to a maximum value if it is determined that the PWM signal will be saturated. In PWM control, the output cannot be increased beyond saturation of the signal at 100% duty cycle, i.e. the output is on continually. In that case, setting the output to the maximum avoids potential problems with the PWM generation.

The feedback control may comprise proportional control and integral control and the method may further comprise resetting the integral control if it is determined that on the basis of the output of the proportional control the PWM signal will be saturated. This avoids integral wind-up, where the integral portion acquires a large value before the proportional component comes out of saturation.

The control method of this aspect may also be applied to control of other processes than heating, it can be applied to any feedback control method based on an error signal.

It may be required to heat a relatively large area, in comparison to the surface area of a typical surface mount resistor. This may require an unacceptably large number of resistors to be provided to heat the area required. In such cases it would be desirable to provide an alternative heater assembly. Such a heater assembly may comprise any suitable thermal source, including an electromagnetic power source.

Accordingly, a yet further aspect of the invention provides a heater comprising a printed circuit board, wherein the printed circuit board comprises:

a heating layer having at least one trace for providing resistive heating when an electrical current flows through the trace; and a heat spreading layer forming a heating surface and positioned above the heating layer.

It has been found that a trace or track of a printed circuit board can provide enough heat output to act as heater, for example as discussed in U.S. Pat. No. 6,841,739. However, simply using a trace as a heater may not give a sufficiently even heat distribution for use in sample analysis. The present aspect of the invention therefore provides a heat spreading layer which provides a heating surface and is formed adjacent the heating layer so that the heat is spread evenly. The heat spreading layer can be manufactured using known techniques for printed circuit boards so the heater can be manufactured simply and cost effectively.

Preferably, the at least one trace of the heating layer follows a path configured to provide substantially uniform heating. Despite the presence of the heat spreading layer, the configuration of the heating layer is still important to provide uniform heat distribution.

The at least one trace may follow a tortuous, winding or snaking path over substantially all the area of the printed circuit board.

At least a part of the at least one trace may follow an undulating path having peaks and troughs including a portion wherein peaks of an outward path extend under peaks of a return path and troughs of the return path are contained within troughs of the outward path. Here, "outward" and "return" are relative terms, the outward path is electrically before a return path, if polarity is reversed the "outward" path will then become the "return" path and vice versa.

At least a part of the at least one trace may follow an undulating path having peaks and troughs, wherein peaks of an outward path are adjacent troughs of a return path and vice versa.

The heater may further comprise a protective layer formed on the heat spreading layer.

The heater may further comprise a temperature sensor. The temperature sensor may comprise a thermistor, for example according to one of the aspects described above (with or without one or more of the optional features). The heater may be controlled by the method described above (with or without one or more of the optional features).

The printed circuit board may further define a recess in which the temperature sensor is provided.

The heating layer may be electrically isolated or grounded.

In a related aspect, an apparatus for analyzing a sample provided in a sample cartridge is provided, wherein the apparatus comprises a heater according as discussed above (with or without one or more of the optional features).

During sample analysis it may be necessary to control different parts of an analysis section to different values. An example is during capillary electrophoresis, where different elements may be required to be at different voltages. It would be desirable to ensure that all elements reach the required value at the same time, so that the relative values remain constant.

Accordingly, another aspect of the present invention provides a high voltage power supply comprising:
 a first power converter for generating a first output voltage;
 a second power converter for generating a second output voltage, which is different from the first output voltage; and
 a controller for controlling the first power converter and the second power converter such that, when first and second voltage are changed simultaneously, the output from the first power converter reaches the first output voltage and the second power converter reaches the second output voltage substantially simultaneously.

The apparatus may further comprise an interlock to disconnect power from the first power converter and second power converter when a housing is open.

In a related aspect, an apparatus for analyzing a sample using capillary electrophoresis is provided, comprising a high voltage power supply as discussed above (with or without the optional feature) for providing the voltages used in the capillary electrophoresis.

In another related aspect, a method of controlling a power convertor to reach an output voltage in a predetermined time is provided, the method comprising:
 calculating an output voltage change required in the predetermined time;
 dividing the predetermined time into a plurality of consecutive steps, each of the plurality of steps lasting the same time;
 calculating the output voltage change required in each of the plurality of steps;
 adjusting the output voltage by the output voltage change in each of the plurality of consecutive steps.

By ensuring that an output voltage is reached in a predetermined time, multiple voltages can reach their respective output voltage at the same time, by using the same predetermined time for each one. The controller discussed above may be adapted to use this method.

In another related aspect a method of controlling a first power converter to reach a first output voltage and a second power converter to reach a second output voltage substantially simultaneously is provided, the method comprising:
 determining a delay time after which the first power converter will reach the first output voltage and the second power converter to reach the second output voltage substantially simultaneously;
 dividing the delay time into a plurality of consecutive steps, each of the plurality of steps lasting the same time;
 calculating a first output voltage change required for the first power convertor in each of the plurality of consecutive steps;
 calculating a second output voltage change required for the second power convertor in each of the plurality of consecutive steps;
 adjusting the output voltage of the first power convertor by the first output voltage change and adjusting the output voltage of the second power convertor by the second output voltage change in each of the plurality of consecutive steps.

The controller discussed above may be adapted to use this method. It will appreciated that the method is not limited to only first and second power convertors, it can be extended to three, four, or more power convertors as required.

During sample processing it may be required to expose a sample to a controlled magnetic field.

Accordingly in a further aspect, the present invention provides an apparatus for interfacing with a sample cartridge, wherein the sample cartridge comprises a section for processing a sample in a predetermined magnetic field; wherein the apparatus comprises a magnet assembly for providing a variable, controlled magnetic field strength and the magnet assembly is positioned such that in use, when the apparatus is interfaced with the biological sample cartridge, the magnet assembly is adjacent the section for processing a biological sample in a predetermined magnetic field.

The predetermined magnetic field may be in the range 300-1200 Gauss, more preferably 350-550 Gauss or 800-1200 Gauss. The predetermined magnetic field is typically used in combination with magnetic beads in the sample cartridge. In that case the material and size of the magnetic beads will generally determine the required magnetic field strength, with smaller beads needing higher field strengths than larger beads of the same material.

Preferably, the magnet assembly comprises a permanent magnet and an actuator for controlling the position of the permanent magnet. The position of the permanent magnet therefore controls the field strength. Alternatively, an electromagnet may be used, in that case the input to the electromagnet determines the field strength.

The magnet assembly may further comprise a shield for limiting the magnetic field in at least one predetermined direction. This can ensure that the magnetic field is directed to the required location.

The magnet assembly may further comprise a magnetic field focuser. This may be a metal film, for example a nickel film.

Some sample processing steps may require use of a laser focused on a particular sample stage. Using mechanical features of a sample cartridge and corresponding analysis apparatus to align a laser with a sample cartridge may not align them reliably. There remains a problem that the laser may not be correctly focused or aligned with the sample cartridge.

Accordingly, a yet further aspect of the invention provides an apparatus for aligning a capillary of a biological sample cartridge with a laser, wherein the apparatus comprises:
a laser;
an optical path from the laser to the biological sample cartridge comprising at least one lens to focus emitted light from the laser onto the biological sample cartridge;
a CCD;
a cartridge actuator for adjusting the position of the biological sample cartridge; and
a controller for controlling the cartridge actuator on the basis of feedback from the CCD to align the capillary with the laser.

The apparatus may further comprise a lens actuator for moving the at least one lens; and wherein the controller is further for controlling the lens actuator.

The at least one lens may be formed in the sample cartridge.

In a related aspect, the present invention also provides a method of aligning a capillary of a biological sample cartridge with a laser, the method comprising:
illuminating the biological sample cartridge with the laser;
detecting reflected light using a CCD;
moving the biological sample cartridge and determining the optimum position of the biological sample cartridge using output from the CCD.

The reflected light arises from the geometry of a capillary in the sample cartridge. The laser lights the capillary and the geometry and material of the capillary determines the profile of light reflected back to the CCD. This will vary depending on the configuration and material of the capillary, for example glass will have a different response to plastic.

The step of moving the biological sample cartridge may include moving the sample cartridge through its full range of movement and recording the output of the CCD. From this output the optimal position is determined, for example by choosing a peak response, or another feature of the response. The response may have been previously measured for a particular design of sample cartridge, such a capillary of particular dimensions and material to provide a template to assist in choosing the optimum position from the CCD output.

The method may further comprise adjusting focus of a lens in the optical path of the laser using output from the CCD. For example, the output from the CCD may be maximized.

The method may further comprise further comprising adjusting focus of a lens in the optical path of the laser based on a scattering pattern detected by the CCD.

An automated analysis procedure can produce an analysis result without requiring user input. Depending on the analysis many intermediate steps may be carried out before the result is given. It would be advantageous if the user can have access to the results of intermediate steps if required.

Accordingly, a still further aspect of the present invention provides an apparatus for analyzing a sample contained within a sample cartridge, comprising:
a identification reader for reading an identification of an inserted sample cartridge;
a storage device for storing data obtained from analysis of the sample, wherein stored data is associated with the identification from the identification reader.

Thus, data obtained at stages in the analysis can be associated with an identification of an inserted sample cartridge and recalled later, if required.

The identification reader may be a barcode reader.
The identification reader may be a RFID reader.
Preferably, the stored data may further include information on the analysis conditions as well as intermediate and final analysis results. For example, the stored data may include one or more of: information of the operator who operated the machine, information of the reagents used in the analysis process, fluorescence results obtained during any focusing stages, temperatures during processing of the sample, voltages during processing of the sample, and currents during processing of the sample. Including one or more of this additional information can improve the reliability of the data. It can also allow the use of a batch control system, avoiding the need to run a control sample every time analysis is carried out.

All aspects of the processing of a sample may be monitored and files may be created to store the one or more parameters of a sample analysis run. Data stored can also include user, time, the identification of the sample in test, readings from the PCR process that show the entire sequence beginning to end, the voltage and temperature settings for each step in the CE process, readings from the voltage, current, and four temperature sensors taken over the entire test, and all the raw data taken from the CE process with the CCD. This data is stored and available for review at the user's request. Data review may show charts of the entire PCR thermal cycling, the voltage, current, and temperature conditions at every second of the CE phase, and all the images captured by the CCD correlated to time.

It is desirable for the apparatus to receive a sample cartridge automatically. In order for this to succeed it is important that mechanical features of the apparatus are controlled to allow reliable insertion.

Accordingly, in another aspect of the invention, there is provided an apparatus defining an opening for receiving a sample cartridge and comprising at least one sensor for determining the physical position of at least one movable part that interfaces with the sample cartridge. This enables the status of the apparatus to be determined and controlled accurately when a sample cartridge is inserted into the opening. It can prolong the life of components because the at least one sensor can provide feedback when a movement has completed, rather relying on pre-programmed operation times without sensors. The position sensor may be a simple contact switch to determine when an element is in a particular position, or may be a more advanced sensor, for example sensors reporting a relative position throughout the movement, for example range detectors or position sensors.

Various mechanical aspects of the apparatus can be provided with a physical position sensor. For example, two arms may be provided which carry electrode contacts to apply high voltage to the CE chip as required. These arms may initially be in an open configuration to allow a CE chip to be inserted and moved to a closed position after a CE chip has been inserted. The closure operation is stopped when the sensor determined that the arms are closed.

The sample cartridge also needs clearance to allow it to be inserted into in the system, but must be pressed against the circuit board for use to allow valve and pump controls. Again a closure operation may be controlled using the output of a sensor.

The PCR chamber of the sample cartridge also needs to have the Peltiers tightly clamped on both sides to provide a good thermal interface.

In a related aspect a method for inserting a sample cartridge into the apparatus comprises monitoring movement of at least one moveable part from an open to a closed position with at least one sensor, and stopping movement of the at least one moveable part when the at least one sensor indicates that the at least one movable part is in the closed position.

In a more detailed example, when a sample cartridge (optionally including the CE chip) is inserted in to the apparatus and a door is closed, closure of the door is detected and servos are controlled to close in the proper sequence to (i) position the arms onto the CE chip, (ii) press the sample cartridge against the circuit board, and (iii) close the Peltiers onto the PCR chamber in the sample cartridge.

BRIEF DESCRIPTION OF THE DRAWINGS

Various embodiments of the present invention will now be described, by way of example only, and with reference to the accompanying drawings in which:

FIG. 4a is a perspective view of an embodiment of the instrument;

FIG. 4b is a front view of the instrument of FIG. 4a;

FIG. 4c is a side view of the instrument of FIG. 4a;

FIG. 11b is a table of dimensions and volumes for a cartridge according to the present invention, and components thereof;

FIG. 15b is a table of dimensions and volumes for the FIG. 15a cartridge;

FIG. 32 depicts a diagrammatic representation of the construction of a high voltage power supply.

DETAILED DESCRIPTION OF THE PREFERRED EMBODIMENT(S)

Figure 1:
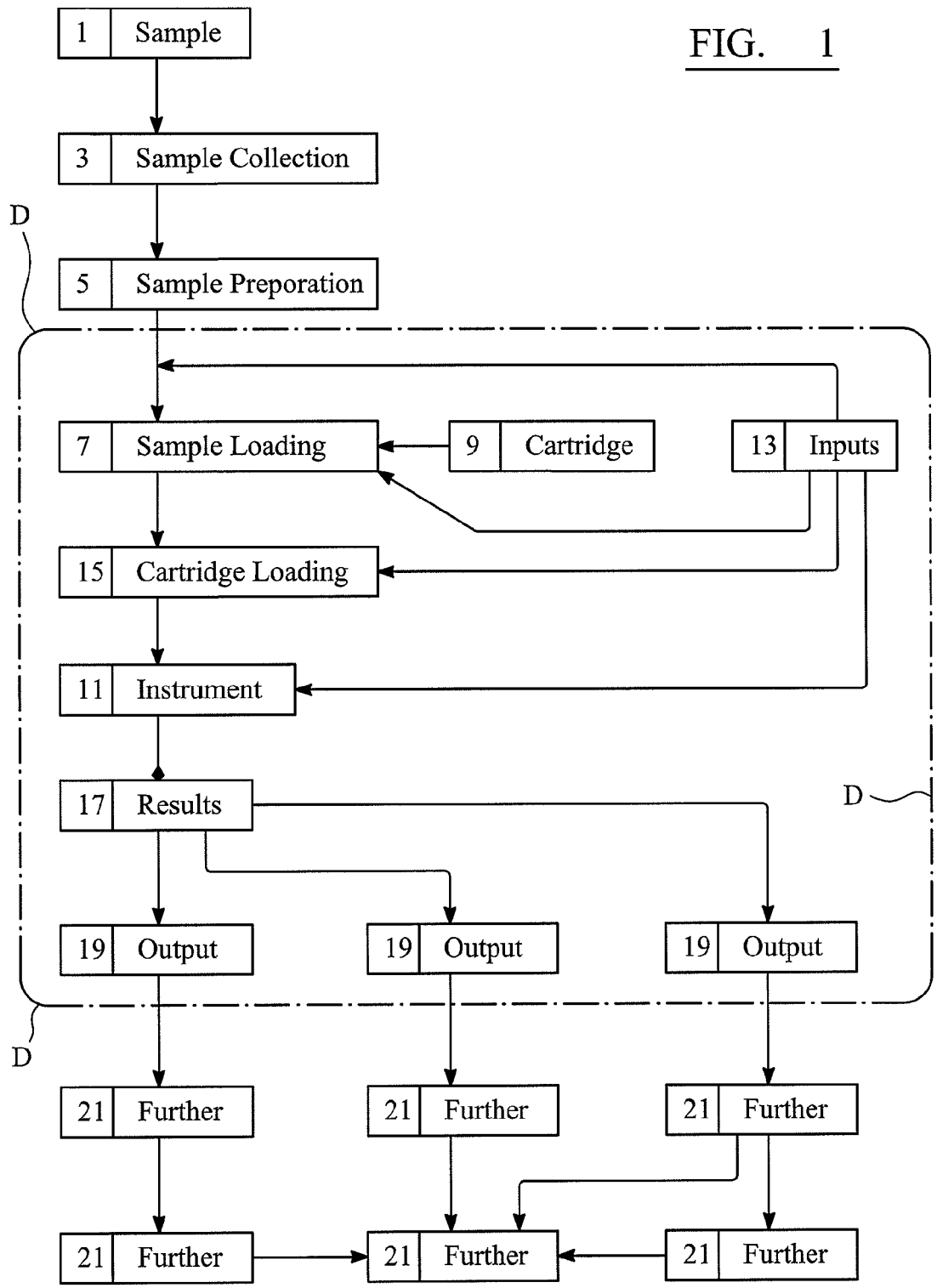
FIG. 1 is a schematic illustration of the stages involved in the consideration of a sample from collection to results and illustrates the positioning of the embodiments of the present invention in that context.

In a variety of cases it is desirable to be able to analyse a biological sample to obtain information on the sample and/or one or more components of the sample. Such cases include medical diagnostics, for instance to look for disease markers, and forensic science, for instance to establish a DNA profile.

At present, such analyses are conducted by highly trained scientists in a laboratory environment. This means that a significant amount of effort and experience goes into the handling of the samples, the use of the analysis equipment and the formulation of the conclusions reached. However, the need to convey the sample to a laboratory environment and then receive the results back from the laboratory environment introduces a potential time delay between obtaining the sample and obtaining the results thereon. The need to use a laboratory environment and highly trained scientists potentially adds to the time required, as the supply of such people and resources is limited. The need to use a laboratory environment and highly trained scientists potentially adds to the cost as there are capital and running costs associated with such facilities and the scientists.

If fewer laboratory style environments are to be used for the analysis or the staff used are less specialised, then there is the potential for problems with the analysis, unless a proper and reliable system is provided.

The present invention has amongst its potential aims to enable analysis of samples at a greater variety of locations and/or non-laboratory type locations. The present invention has amongst its potential aims to enable analysis by personnel having a lower level of training and/or experience. The present invention has amongst its potential aims to enable lower cost and/or faster analysis of samples. The present invention has amongst its potential aims to enable greater use and/or more successful use of analysis by law enforcement authorities.

Many of the concepts and issues to be addressed by the invention are best understood by way of the following examples. It should be noted, however, that these examples are by their very nature detailed and exhaustive, and that benefits from the present invention arise even when only small sections of the examples are implemented in other embodiments of the present invention.

The various embodiments and examples explain the invention initially in the context of a reference sample; that is a sample collected from a known individual under controlled conditions. An example of a reference sample would be a sample collected by a swab from the buccal cavity of a person who has been arrested, the sample being collected at a police station. The invention is also suited to casework samples; that is a sample collected from a location from an unknown individual under non-controlled conditions. An example would be a spot of blood collected by a swab from a crime scene, with the source of the blood unknown. Where the differences between reference samples and casework samples have an impact on the preferred forms of the instrument, cartridge and methods, the casework sample embodiments are separately described.

The substitution of one or more components by one or more different components or different arrangements of components is also envisaged where particular conditions or issues arise. Again, after the discussion of the reference sample and casework sample contexts for the instrument, these alternatives are described.

As a starting point, it is useful to establish the context of the instrument, cartridge and methods of use in the overall context in which they may be used, by way of example. Thus in FIG. 1 there is a schematic of the overall process into which the present invention fits. This overall process includes a sample 1 which is gathered in a sample collection stage 3. This is followed by a sample preparation stage 5. In the subsequent sample loading stage 7, a prepared cartridge 9 is loaded with the collected and prepared sample 1. The next stage is the cartridge installation stage 15 in which the cartridge 9 is introduced to the instrument 11. The instrument 11 also receives various inputs 13 at the sample loading stage 7 and/or at the cartridge installation stage 15 and/or subsequently.

The structure and processes performed within the instrument 11 and cartridge 9 are described further below in the context of FIG. 2.

Once the instrument 11 has completed these stages and achieved the analysis, the next stage is the results stage 17. This is followed by one or more output stages 19, and potential further stages 21 which integrate the analysis into the criminal justice system of that jurisdiction. A wide range of possible links between the various output stages 19 and further stages 21 may be possible, with some being linked to just one stage and others be the result of multiple such stages and/or combinations thereof.

An output stage 19 may include the transmission of the results from the instrument to a remote location for processing. The processing may be performed using complex software and/or hardware tools, before the final results are returned to the instrument 11 or to another computer. Processing the results at a remote location may be preferably in terms of the size, cost or complexity of the software/hardware needed to perform the processing thus only being provided at a limited number of locations, rather than a part of each instrument.

The following description of the operation of the instrument 11, in a generally sequential manner, provides full details of the key instrument stages and their interrelationship.

Figure 2:
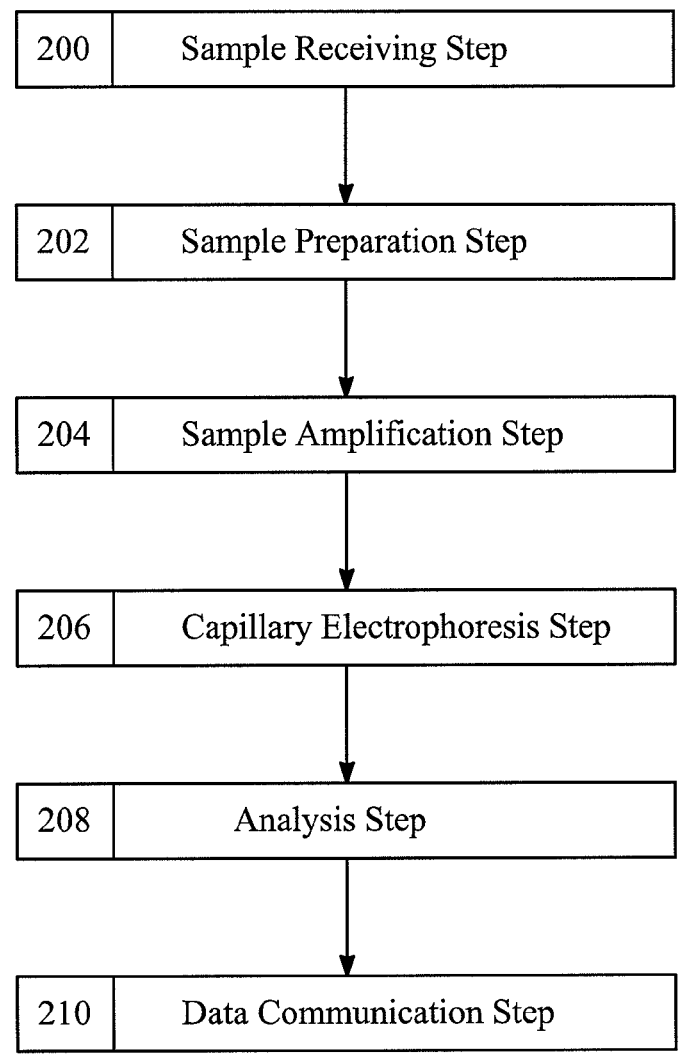
FIG. 2 is a schematic illustration of the key steps provided on or by an instrument embodying the present invention.

Referring to FIG. 2, the instrument has a sample receiving step 200, sample preparation step 202, sample amplification step 204, electrophoresis step 206 and analysis step 208 and data communication step 210.

In the sample receiving step 200, the sample 1 is transferred from a sample storage and/or processing stage 5, which is outside of the cartridge 9 and instrument 11, to a location on the cartridge 9.

The initial collection device is frequently a swab. The swab is used to pick up the sample 1 from an article or substrate.

In the sample preparation step 202, the key components within the sample are contacted with the reagents and/or components intended to prepare the sample for the subsequent steps. In this embodiment, the sample preparation step 202 contacts the sample with beads to retain the DNA and recover it, whilst the other components which are not to be recovered flow through and away. The sample preparation step 202 also includes contact with a wash agent to improve the separation of the DNA from the other components. The wash agent flows through the chamber holding the beads and retained DNA and flows to a further chamber, a waste chamber. The wash agent is followed by an elution agent to release the DNA from the beads for the subsequent steps.

In the sample amplification step 204, the DNA is contacted with amplification reagents and provided with the conditions necessary to achieve amplification through PCR.

In the electrophoresis step 206, the amplified DNA is conveyed to a start point for a mobility based separation within a capillary. An electric field is then used to separate the complex DNA amplicons into different size clusters.

In the analysis step 208, the channel is inspected to establish the relative position and hence size of elements detected in the capillary. This is achieved by an excitation light source, fluorescent markers associated with the elements to be detected and suitable optics to detect the fluorescent light resulting.

In the data communication step 210, the instrument compiles the necessary data packet for transmission and transmits it to a remote location for consideration. The data packet includes information on the electrophoresis results, sample identity and other information. The analysed results may be received by the instrument as part of the data communication step 210.

Some data processing may be performed on the instrument itself, for instance to deconvolute the analysis results to indicate the peaks indicative of alleles present.

The instrument can be provided in a format which considers a single sample at a time, or can be provided in a format which considers multiple samples at a time. The multiple samples may each be run on separate cartridges, but modified cartridges which handle multiple samples are possible. The handling of multiple cartridges is beneficial in allowing a single set of controllers, power supplies, optics and the like to consider multiple samples, with reduced capital costs.

Instrument Performance

The result of the above embodiment is the provision of an instrument, cartridge and operating method which provides quick, reliable sample analysis, whilst doing so at a wide variety of locations and when operated by a wide variety of people.

By way of abilities are performance, the invention provides a fully integrated instrument capable of performing extraction, PCR, electrophoresis and analysis, whilst requiring minimal training and/or intervention by the user. In its optimum form, a fully automated system from start to finish is provided, the user simply needing to load the cartridge into the instrument and start it.

The modular nature of the instrument allows for upgrading of one or more modules without impact on the other modules. The data output format has been carefully selected to allow the analysis of the data outputted by a variety of existing analysis software applications, such is $I^3$ of Forensic Science Service Limited, and future software applications.

The end result of the analysis may be a profile for the sample and/or an indication of a match between the sample and a database recorded sample and/or other interpretation based data.

The use of a single cartridge type to handle a wide variety of sample from a wide variety of sources is beneficial. The methodology is able to handle samples originating from buccal swabs, cotton and other soft swabs, aqueous samples, clothing samples, cigarette butts, chewing gum and the like.

The methodology is also able to separate the useful DNA from residual cellular material, PCR inhibitors (such as ethanol, indigo etc) and chemical inhibitors.

The instrument is fully portable and so can be used in a wide variety of locations. The fully sealed and protected nature of the cartridge means that contamination is not a risk, even where the instrument is used outside of laboratory standard conditions. The instrument operates off a standard mains power supply, 110-240V, 50 Hz, using a conventional electric plug.

With respect to the overall time, from the sample receiving step 202, to the transmission away from the instrument in the data communication step 210, the embodiment described provides this process in a time period of 141 minutes. That time period can be reduced, including by the options and variables set out in the following paragraphs.

With respect to the sample receiving step 2002, the embodiment described provides this step in a time period of 2 minutes. Time periods of between 20 seconds and 5 minutes are easily achievable, depending upon the loading methodology used and the number of reagents or samples that need to be loaded.

With respect to the sample preparation step 202, the embodiment described provides this step in a time period of 24 minutes. That time period can be reduced by shortening the residence in one or more of the chambers, for instance the incubation chamber 358, and/or by reducing the time separation between a valve being activated and reliance on the outcome of the activation and/or by reducing the washing and/or elution volumes used. Time periods of between 15 to 30 minutes are easily achievable.

With respect to the sample amplification step 204, the embodiment described provides this step in a time period of 80 minutes. That time period can be reduced by shortening the number of cycles used, the duration of one or more parts of a cycle and the time period after introduction to the chamber and before PCR starts and/or after PCR finishes and before the sample is removed to the next stage. Again, the time separation between a valve being activated and reliance on the outcome of the activation is of significance. Time periods of between 60 to 120 minutes are easily achievable.

With respect to the electrophoresis step 206, the embodiment described provides this step in a time period of 15 minutes. That time period can be reduced by the use of higher voltages and/or faster migration media in the capillary and/or reductions in the sample introduction time. Time periods of between 1 to 60 minutes are easily achievable.

This functionality is achieved in an instrument weighing less than 10 kg and occupying a footprint of less than 0.1 m$^2$.

Instrument Fields of Use

The structures and method discussed above and below are useful in the consideration of a wide variety of samples, over and above forensic samples. For instance, they can be used: the consideration of marker targets, diagnostic assays, disease markers, biobanking applications, STR based targets in transplants, identification of drug resistant microorganisms, blood testing, mutation detection, DNA sequencing and the like. Food analysis, pharmogenetics and pharmogenomics are also areas of use. A wide variety of uses in the medical and/or biotech field can make use of the invention.

The invention is also applicable in situations where familial relationships need to be determined from DNA, for instance paternity testing. Pedigree testing in animals is a further example.

The use of the invention in border control, security, customs situations and other governmental type uses is beneficial.

Instrument Configuration and Appearance

Figure 3:
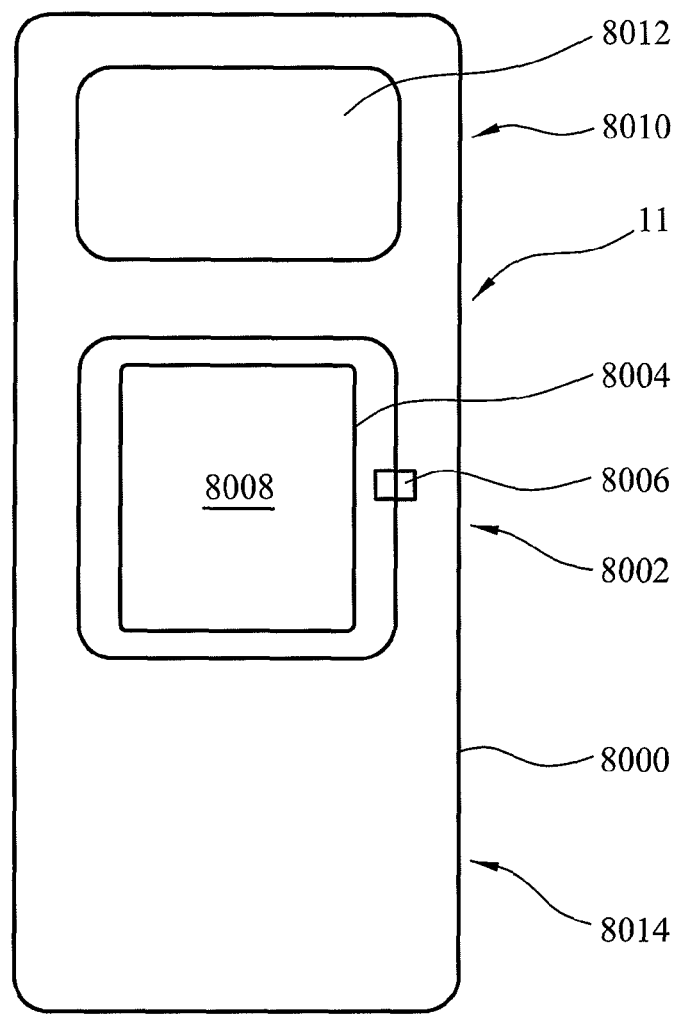
FIG. 3 is a schematic front view of one embodiment of the instrument.
Figure 6:
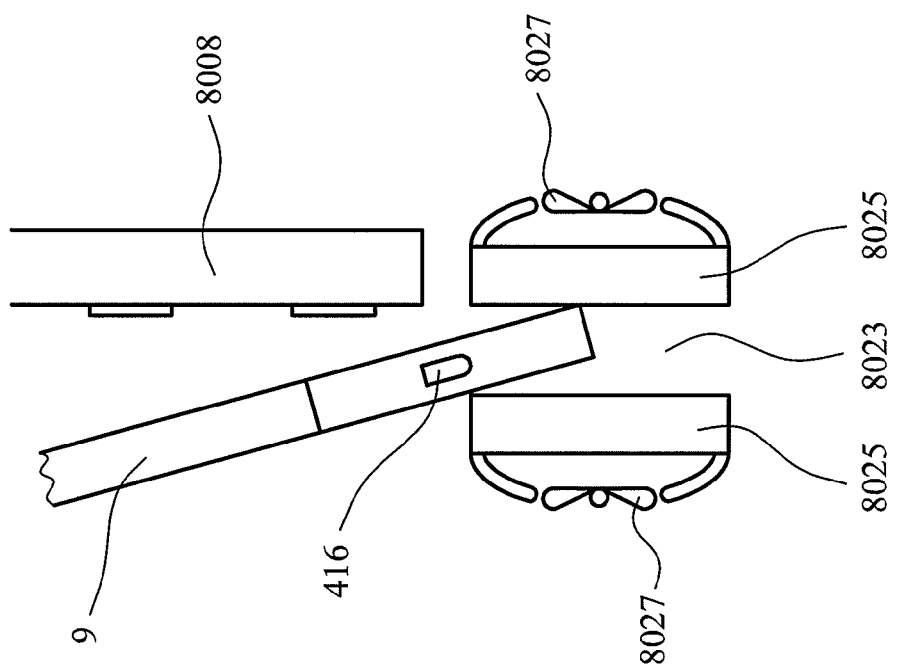
FIG. 6 is a side view showing the insertion of the cartridge into the instrument.

The instrument 11 is illustrated in FIG. 3 and is provided within a casing 8000. The mid section 8002 of the instrument 11 is provided with a door 8004 provided with a latch 8006. Behind the door 8004 is the location at which the cartridge, described in more detail below, is mounted in use. This location is a position in which the plane of the cartridge is parallel to the plane of a printed circuit board 8008; FIG. 6. At the location, the cartridge and components on the printed circuit board 8008 contact one another.

Behind the printed circuit board 8008 are the electronics for operating and controlling the components provided on the printed circuit board 8008. These include the power supplies, voltage controllers, temperature controllers and the like. These are described in more detail below.

The upper section 8010 of the instrument 11 provides the display 8012 by means of which the user inputs information into the instrument 11 and receives visual information from the instrument. The software and hardware for operation of the display 8012 are provided on a computer positioned behind the display screen 8012 in the upper section 8010.

The lower section 8014 of the instrument 11 contains the high voltage power supply and controller for the laser used in the inspection of the capillary electrophoresis. Also in this lower section 8014 are the charge couple device used to sensor the fluorescence and the optics for conveying the light to and from the capillary.

Figure 4C:
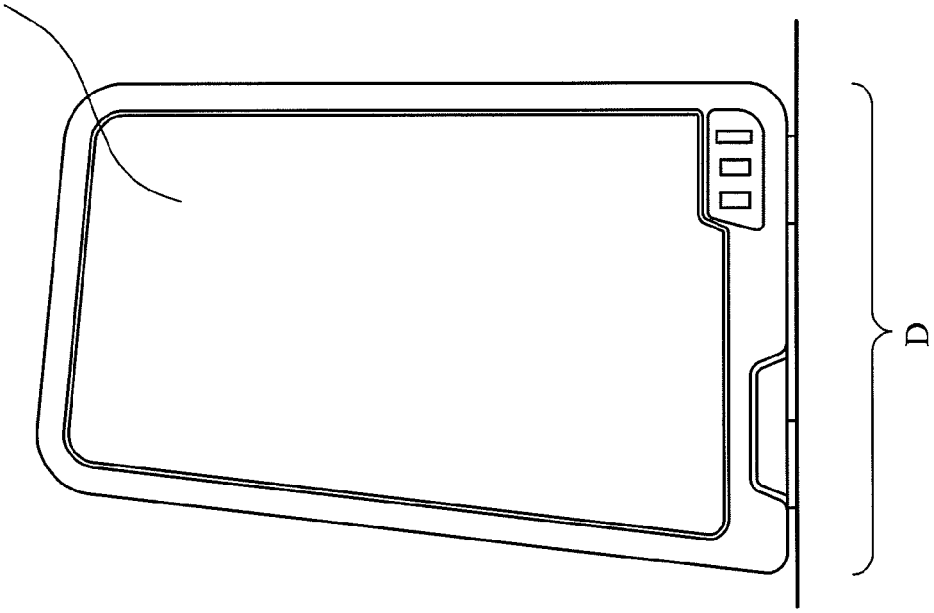

Another embodiment of the instrument is shown in FIGS. 4*a*, 4*b* and 4*c*. The instrument 29-11 is provided within a casing 29-8000. The upper section 29-8002 of the instrument 11 is provided with a door 29-8004. The door 29-8004 is a combination of a top section 29-8006 and front section 29-8008 of the casing 29-8000.

The lower section 29-8010 of the instrument 11 provides the display 29-8012 by means of which the user inputs information into the instrument 11 and receives visual information from the instrument 11.

The window 29-8014 allows for visual inspection of the cartridge used. A series of light bars 29-8016 are used to indicate the extent of progress through the steps involved; the more of the bar which is lit the greater the extent of the step performed.

A stylus 29-8018 is used by the operator to interact with the display 29-8012.

Various control buttons 29-8020 are provided below the screen 29-8012.

The overall dimensions of the instrument are width, W, 419 mm, overall height, OH, 621 mm, depth, D, 405 mm.

Figure 5:
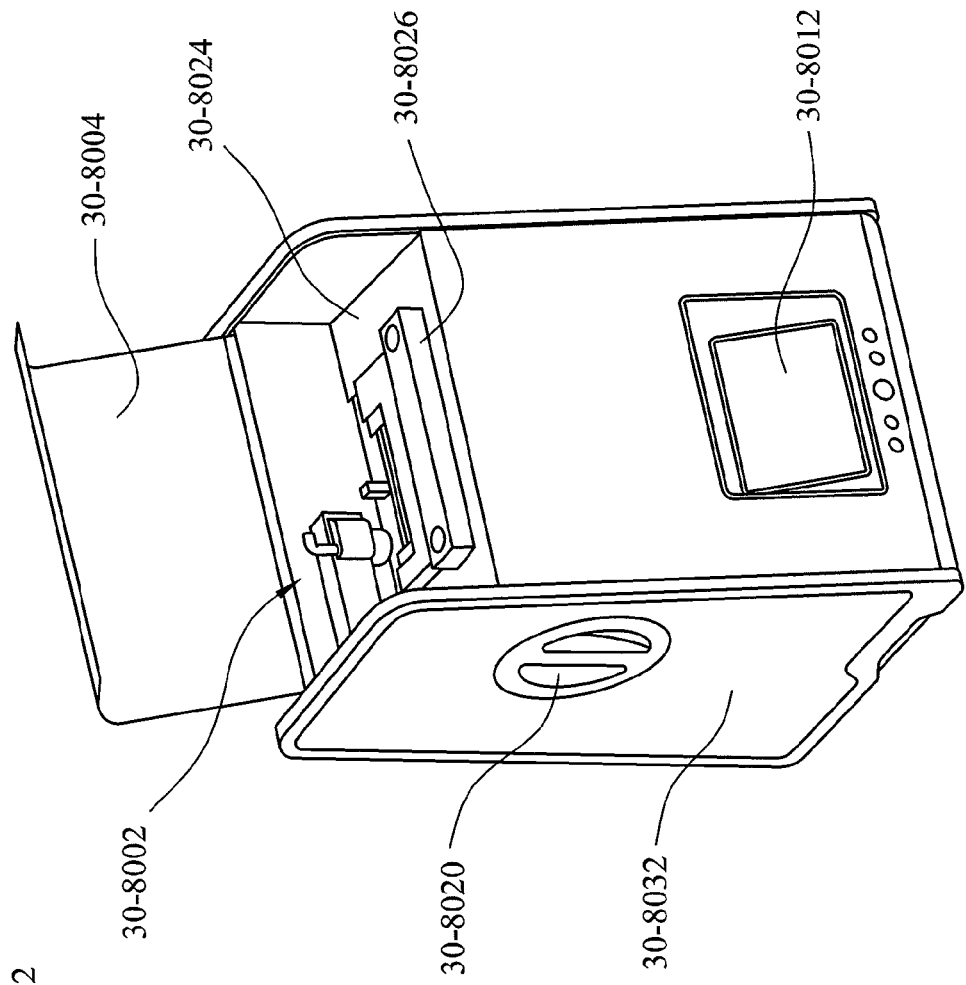
FIG. 5 is a perspective view of another instrument embodiment.

The side panel 29-8022 is removable for maintenance purposes. The embodiment of FIG. 5 shows the door 30-8004 structure more clearly, together with the workspace 30-8024 that is accessed through it. The workspace 30-8024 includes the slot into which the cartridge carrier 30-8026 is inserted. The cartridge carrier 30-8026 is as described elsewhere in this document. The workspace 30-8024 also includes the lane finding apparatus 30-8028.

The cover 30-8030 in the side panel 30-8032 is opened by rotation to allow access to the optics for maintenance purposes.

Cartridge to Instrument Interface

Once the cartridge is loaded with the sample, the cartridge is loaded into the instrument 11 for the processing to be conducted.

As a first step, the latch 8004 is released and the door 8002 is opened.

To insert the cartridge 9, FIG. 6, the section of the cartridge 9 which bears the PCR chamber 416 is inserted into a slot 8023 between the components which will control the PCR process. These components include the thermoelectric heaters/coolers, Peltier devices 8025, and fans 8027 there for. These components are free to travel to a limited extent to help with the locating of the cartridge 9 within the slot 8023, whilst being forcibly returned to the optimum position after insertion so as to give effective heating/cooling.

The cartridge 9 is provided with a series of recesses which cooperate with dowels extending through the printed circuit board 8008 to accurately register the cartridge 9 relative to the printed circuit board 8008. The dowel arrangement is such that the cartridge 9 cannot be fitted the wrong way round.

Once positioned, the cartridge 9 is provided in a plane which is parallel to the plane of the printed circuit board 8008. Both components have flat surfaces facing one another so as to assist with the good contact needed between them.

The closing of the door 8002 and operation of the latch 8004 applies a compressive force to the cartridge 9 by way of a series of spring loaded pins mounted on the inside surface of the door 8002. This helps hold the cartridge 9 in firm contact with the printed circuit board 8008.

The printed circuit board 8008 is important to the successful operation of the invention. It provides the energy sources for the various components to be driven on the cartridge 9. In effect, the drivers are all provided in the cartridge 9, but the energy sources are provided on the printed circuit board 8008. In this way, the precision operation needed is ensured by the expensive and bespoke electronics and arrangement of the printed circuit board 8008; a reusable component of the instrument. In this way, the cartridge 9 is simple and self-contained. This reduces the complexity of the interface between the two and also removes the risk of contamination of the contents of the cartridge 9. The only transfer between the printed circuit board 8008 and the cartridge 9 is conducted and radiated heat from the heaters and the magnetic field provided by the magnet.

The components provided on the printed circuit board include:

a) The electrical contacts which connect to the pins of the electrochemical pump electrodes on the cartridge 9. These provide the electrical power, when needed, to operate the electrochemical pumps.

b) The electrical heaters which are used to apply heat to the valves on the cartridge so as to open or close the valves depending upon their type. These are square areas of resistance heating material which is applied by printing a paste to the desired location. The heating effect is improved if the square block is rotated through 45° relative to the axis of the channel subject to the valve.

c) The magnet which is advanced into proximity with the cartridge 9 when it is desired to retain the beads and prevent them from moving. The magnet is retracted away from the cartridge 9 when it is desired to release the beads within the chamber.

d) The sensors are providing feed back and/or verification of the conditions induced by the heaters etc.

Alternatives for Cartridge to Instrument Interface

Figure 7:
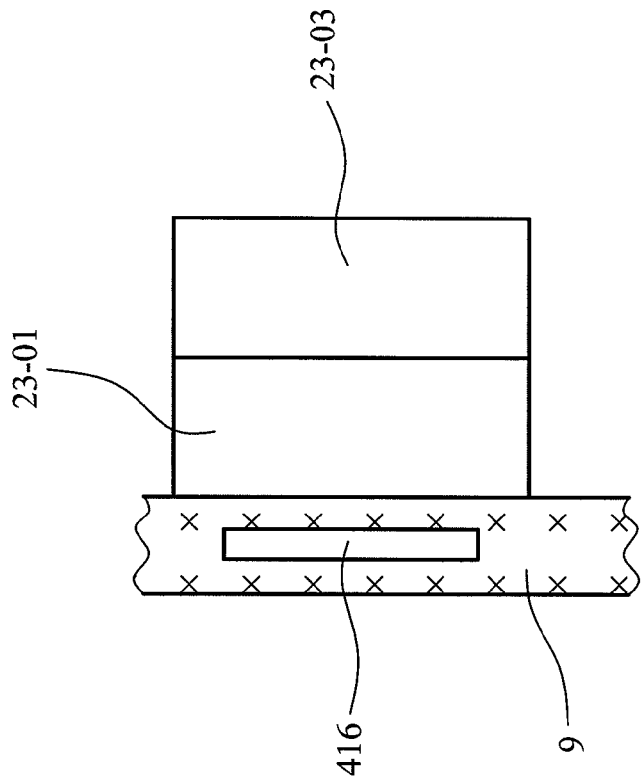
FIG. 7 is an illustration of the position of stacked Peltier effect devices.

If it is necessary to alter or improve the contact between the cartridge and the printed circuit board, there are various options for doing so, including the following:

a) The loading provided by the sprung pins mounted on the door 8002 can be increased. This applies a force to the cartridge 9 and pushes it against the printed circuit board 8008.

b) The cartridge 9 can be mechanically clipped to the printed circuit board 8008, with the clip(s) applying a compressive force.

c) The cartridge 9 can be provided with a compressible substrate mounted on the surface which is intended to contact the printed circuit board. In this way, when then cartridge 9 and printed circuit board 8008 are pushed together, the substrate will provide good all over contact. The substrate can be a solid material, paste or even a liquid. The materials of the substrate, or parts there of, are selected so as to provide maximum thermal conductivity, for instance. Particles, nanoparticles or other materials may be added to alter the properties. The substrate may be protected, prior to use, by a peelable backing.

d) As described above, the components (such as heaters etc) are provided in a fixed position on the printed circuit board 8008. This means they move with the printed circuit board 8008. It is possible to provide one or more, and even each of these components with a degree of independent movement. For instance, they may be provided with a sprung mounting on the printed circuit board. In this way, each is able to independently adjust its position, forward and backwards, relative to the cartridge.

e) As shown in FIG. 7, it is possible to provide the section of the cartridge 9 which bears the PCR chamber 416 in opposition to stacked components which will control the PCR process. In this example, the stack includes a first Peltier device 23-01 in contact with the cartridge 9 and in contact with and aligned with a second Peltier device 23-03. The stacking of the devices allows high temperatures, for instance greater than 150° C. to be obtained within the PCR chamber. Such temperatures are beneficial in terms of melting the high melting point wax seals described elsewhere within this document.

f) Alternative forms of heater may be used instead of Peltier effect device. For instance infra red heating devices may be used. The material around the PCR chamber, or a part of that material, may be capable of resistance heating to give the necessary heating for the chamber. Resistance heaters positioned against the cartridge may be used. Microwave heating may be used.

Alternative Cartridge to Instrument Interface

In the alternative embodiments of the instrument described above in relation to FIGS. 4a, b, c and FIG. 5, the cartridge is not loaded directly into the instrument. Instead, once loaded with the sample, the cartridge 31-01 is loaded into a cartridge carrier 31-03.

The use of the carrier 31-03 means that the cartridge 31-01 and the CE chip can be constructed separately. This allows different material and/or different production tolerances to be used for the different components; a beneficial effect on cost and/or performance and/or the balance between those can thus be provided.

The carrier 31-03 also allows for easy assembly of the required components and their insertion into the instrument in a unitary form. At the same time, the carrier is designed so as to allow separate alignment checking and adjustment for the cartridge and the CE chip so that both are in their correct, optimised position within the instrument.

If desired, the cartridge position can be checked and any alignment adjustment necessary can be made. Before CE starts, a separate check can be made on the alignment of the CE chip, within any adjustments it needs being made before CE starts.

Figure 8:
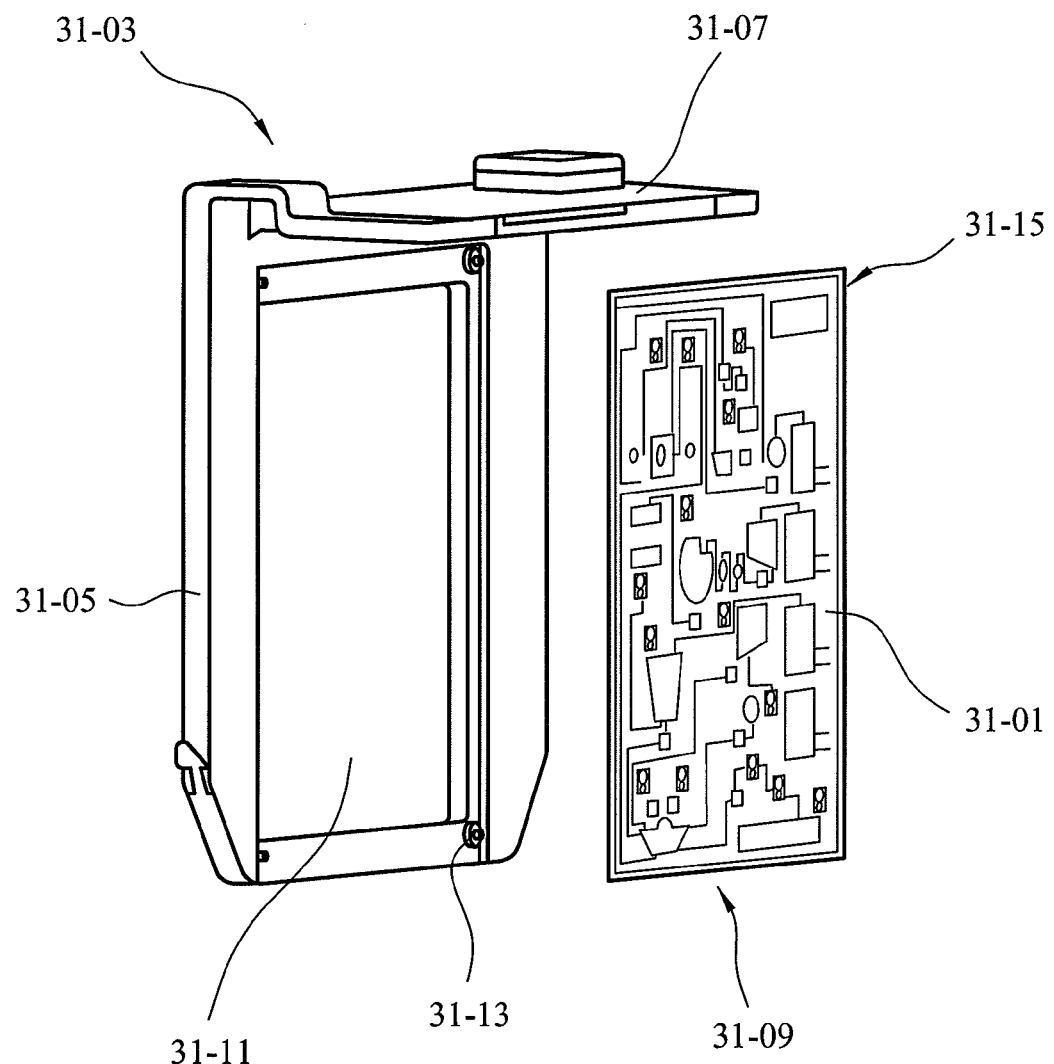
FIG. 8 is an illustration of a carrier, cartridge and CE chip embodiment.

The cartridge carrier 31-03 is illustrated in FIG. 8. The cartridge carrier 31-03 includes a first support 31-05 and a second support 31-07 which is perpendicular to the first support 31-05.

The first support 31-05 is used to carry the cartridge 31-01. The second support 31-07 is used to carry the capillary electrophoresis, CE, chip; this interaction is described further below.

The prepared cartridge 31-01 is presented with its face 31-09 to the face 31-11 defined by the first support 31-05. An externally threaded screw provided at each corner of the first support 31-05 is received into an opposing aperture provided at each corner of the cartridge 31-01. Rotation of the screws causes them to engage with and enter an internal screw thread provided in the apertures. Further tightening mounts the cartridge 31-01 on the first support 31-05 and hence the carrier 31-03 in a secure and known position.

Figure 9:
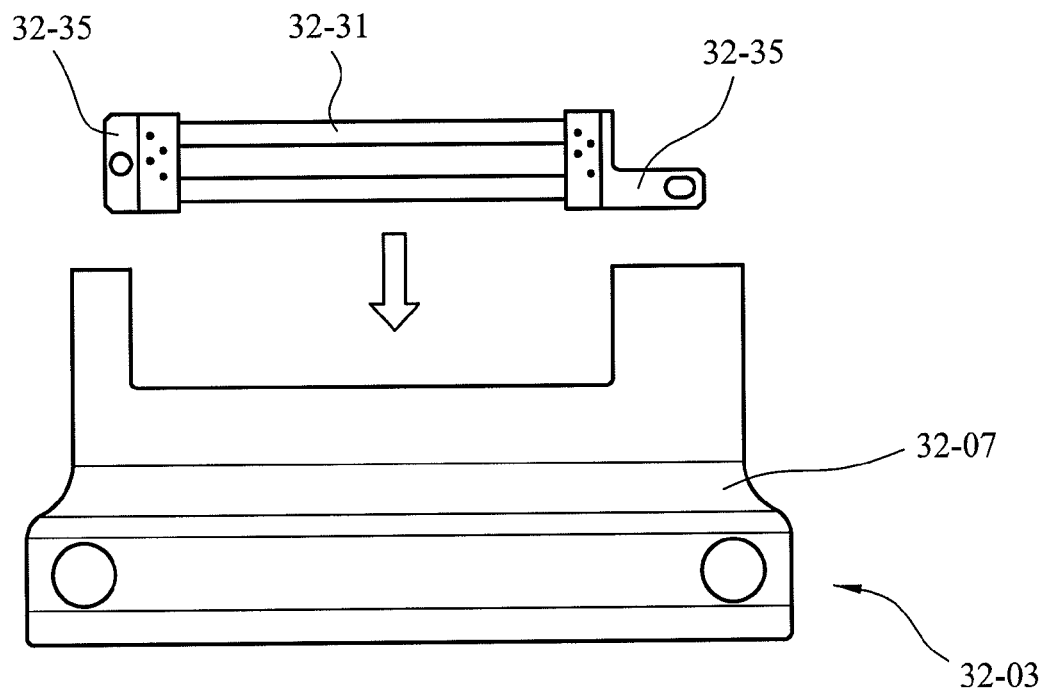
FIG. 9 is an illustration of a carrier to CE chip engagement.

The CE chip 32-31 is inserted into the carrier 32-03 as shown in FIG. 9a. The CE chip 32-31 is slid into a slot. As shown in FIG. 9b, the second support 32-07 provides such a slot 32-33 at either end for receiving the end portions 32-35 of the CE chip 32-31. An incline 32-37 on the lead edge 32-39 of the CE chip 32-31 engages with the end 32-41 of a spring loaded plunger 32-43 and causes it to displace outward, arrow A. Once the recess 32-43 is presented to the end 32-41 of the plunger 32-43, the plunger 32-43 returns, arrow B, and so prevents onward movement of the CE chip 32-31 past the desired position.

Once the cartridge 31-01 and the CE chip 32-31 are inserted into the carrier 31-03, 32-03, the fluid connection between the two is provided by a tube.

After insertion of the cartridge 31-01 and the CE chip 32-31 into the carrier 31-03, as described above, the carrier 31-03 is ready for insertion.

As a first step, the door 30-8004 is opened, to expose the workspace 30-8024. The work space 30-8024 includes the slot that the carrier is inserted into.

The carrier is inserted into the slot until the second support comes to rest on the surface of the workspace 30-8024. The cooperation of the carrier with the slot ensures the correct general positioning of the cartridge with respect to the instrument, both in terms of lateral and vertical positioning; FIG. 5.

Insertion in this way provides the section of the cartridge which bears the PCR chamber between the components which will control the PCR process; as described further below.

Once inserted, the door 30-8004 is closed. The closing of the door 30-8004 triggers various actions based upon contact between the closed door 30-8004 and casing. The clamping of the cartridge to the PCB, the positioning of the CE chip on the CE chip heater board, the introduction of the electrical contacts to the pins provided on the CE chip, the introduction of the electrical contacts to the pins providing the conduction path to the electrodes in the electrochemical pumps are all triggered in this way. The closure of the door 30-8004 is also used to turnoff the interlock for various safety systems within the instrument. The interlock prevents, for instance, the laser being active with the door or any other opening in the instrument's casing being open. A similar principle applies to the power supplies within the instrument.

As with other embodiments, it is important to provide effective and accurate contact between the cartridge and the instrument interface.

The face to face contact between the cartridge and the PCB provides the majority of the interactions between the cartridge and the instrument, for instance, heating for valve control, sensor etc. The contact between the PCR chamber and its temperature cyclers are provided through further components, however; see FIG. 36a, b, c and d.

Figure 10A:
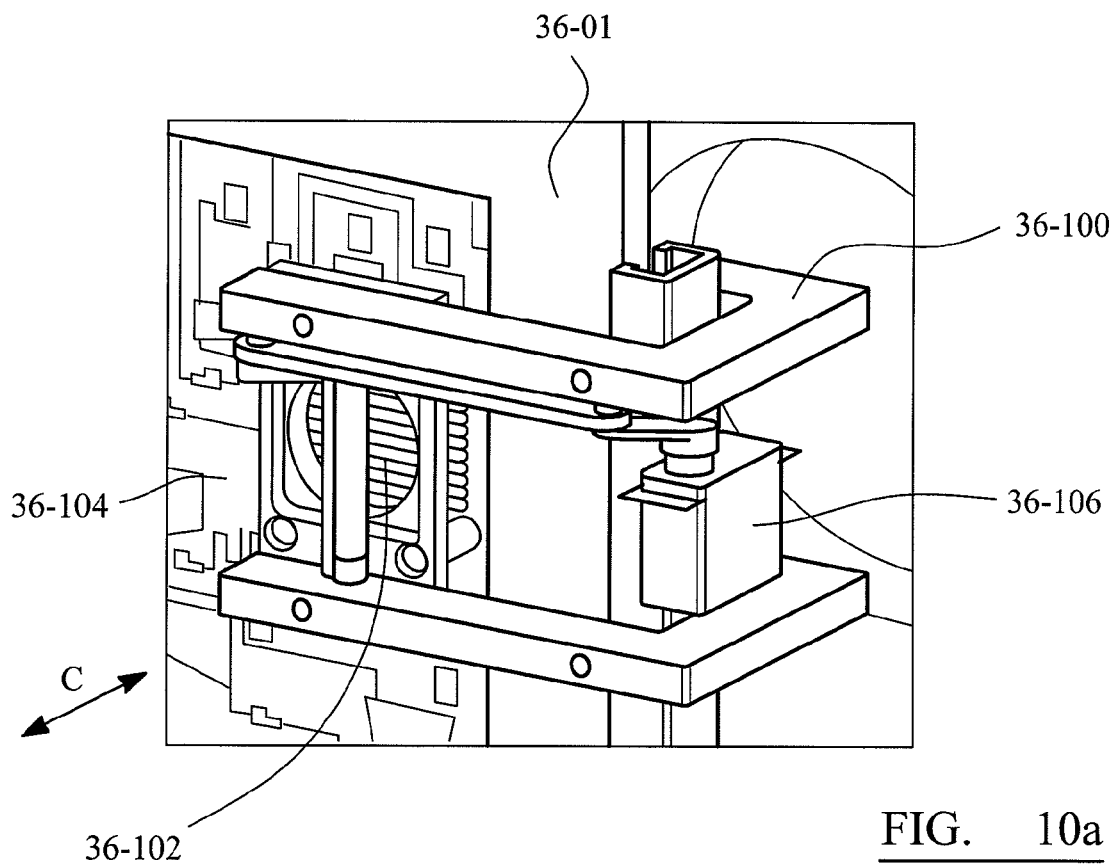
FIG. 10a is a perspective view of the position of the pair of calipers.

In FIG. 10a, the cartridge 36-01 is shown inserted into the slot provided in the instrument. Once inserted, the section of the cartridge 36-01 bearing the PCR chamber is positioned between a pair of calipers 36-100. The PCB is cut away at this location so as to not be in the way of the Peltier effect devices 36-102, 36-108 and pair of calipers 36-100. The calipers 36-100 are floating such that they do no interfere with the contact sought between the cartridge 36-01 and the PCB during the movement from the insertion position to the use position.

The front caliper 36-100a is provided with a Peltier effect device 36-102 mounted on a support 36-104 which is capable of reciprocating movement, arrow C, under the control of actuator 36-106. The actuator 36-106 is also mounted on the pair of calipers 36-100.

The back caliper 36-100b is provided with a second Peltier effect device 36-108 mounted fixedly on the caliper 36-100b. The second Peltier effect device 36-108 is provided in opposition to the Peltier effect device 36-102.

Figure 10B:
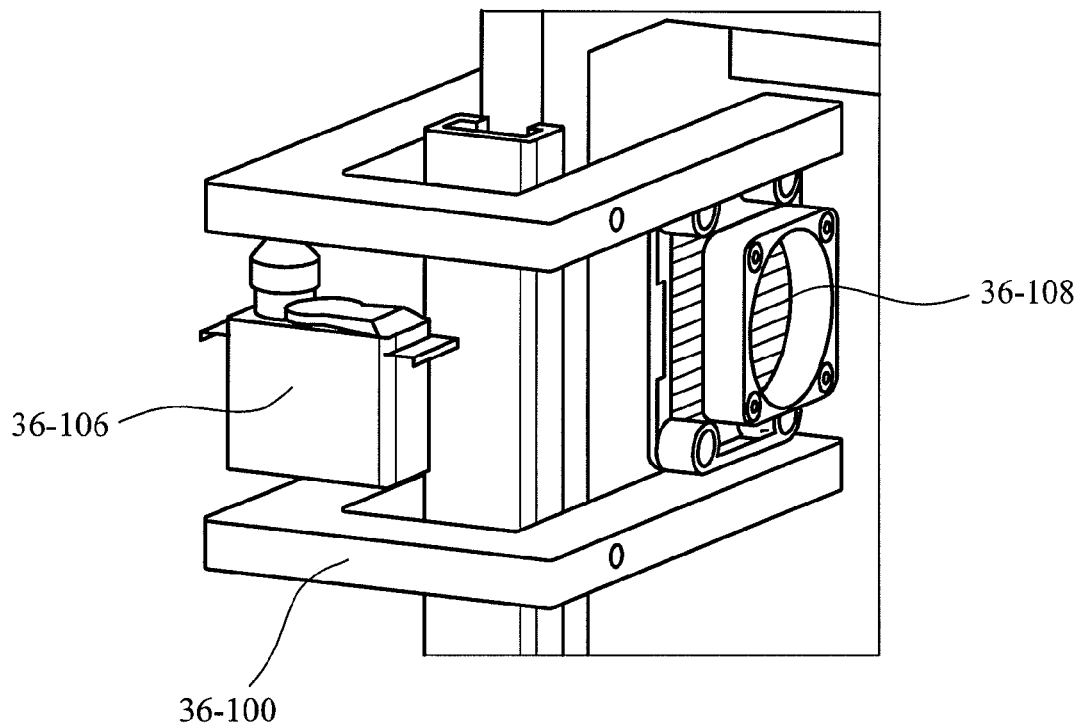
FIG. 10b is a perspective view of the back of the pair of calipers.
Figure 10C:
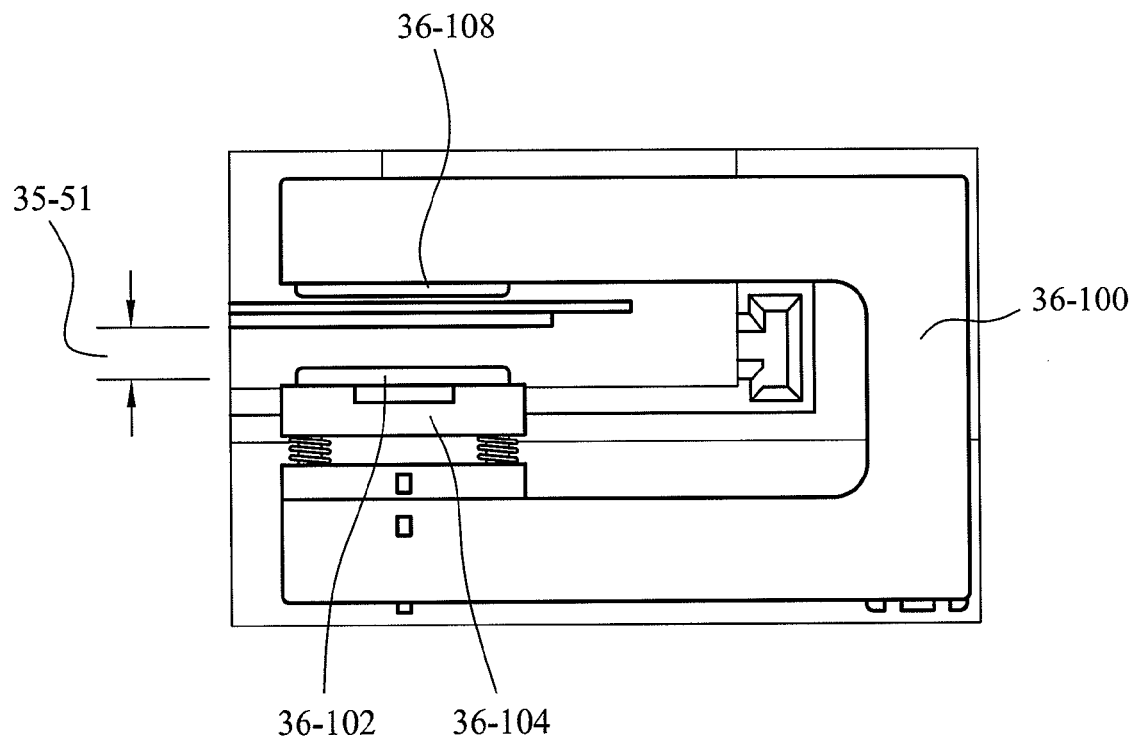
FIG. 10c is a plan view of the caliper structure in the open form.

In the open position shown in FIG. 10c, such as is provided with the cartridge in the insertion position, the distance between the opposing faces 36-110, 36-112 of the Peltier effect device 36-102 and the second Peltier effect device 36-108 is more than the thickness of that section of the cartridge 36-01 and more than the thickness of the carrier 36-03 which passes between the pair of calipers 36-100 during insertion of the carrier 36-03.

Figure 10D:
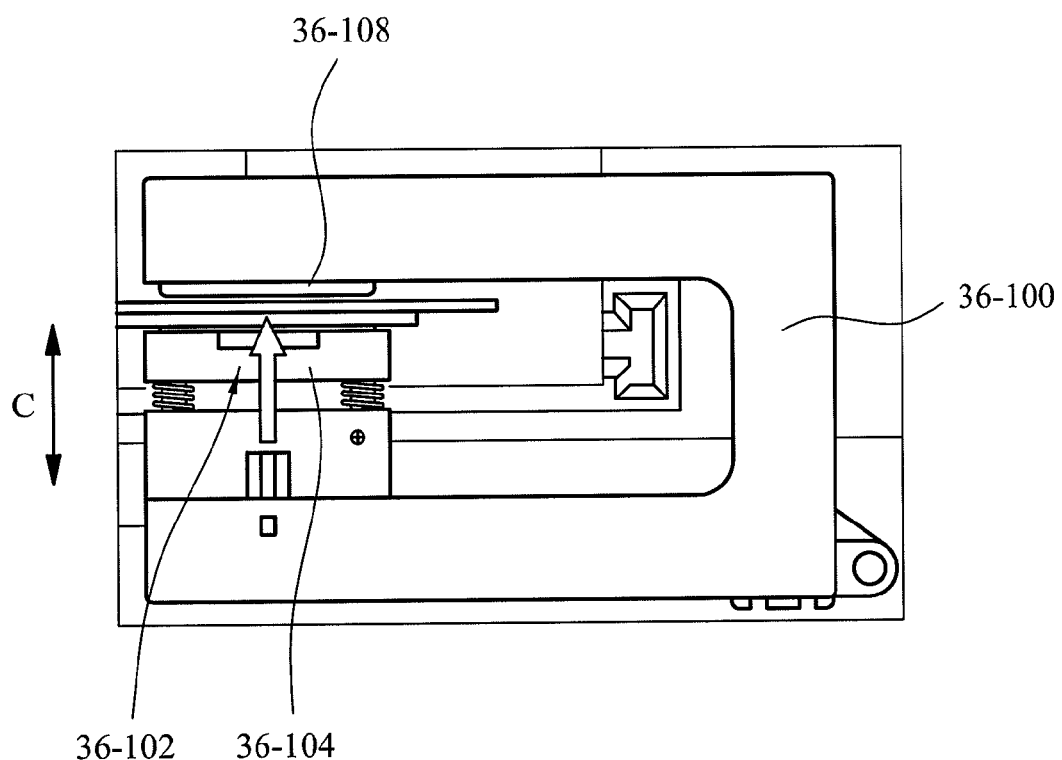
FIG. 10d is a plan view of the caliper structure in the closed form.

In the closed position shown in FIG. 10d, such as is provided during the amplification step, the distance is reduced. This is achieved by the actuator 36-106 moving the Peltier effect device 36-102 on the front caliper 36-100a towards the cartridge 36-01 and towards the opposing second Peltier effect device 36-100b. This actuation, combined with the floating nature of the pair of calipers 36-100 brings both of the Peltier effect devices into firm contact with the cartridge 36-01 on opposing sides thereof. They are now in position to provide the necessary heating and/or cooling for the PCR step.

Thermocouples to sense the temperatures applied, and potentially to be used to control the temperatures applied, are provided in close proximity with the Peltier effect devices, embedded in copper shims, bonded to the Peltier effect devices.

Before the carrier 36-03 is removed, the actuator 36-106 returns the Peltier effect devices 36-100 to the open position.

Cartridge

Key to the operation of the instrument is a disposable, single use cartridge 9. This cartridge 9 is intended to only process and provide the results for analysis on a single occasion. The disposable nature of the cartridge 9 places a number of constraints on the cartridge 9 in terms of the materials which can be used, because of the need to keep manufacturing, assembly or purchase costs low.

The detailed layout of the cartridge 9 is now described. Later, a description of the sequence of operation of the elements which make up the cartridge is provided.

Figure 11A:
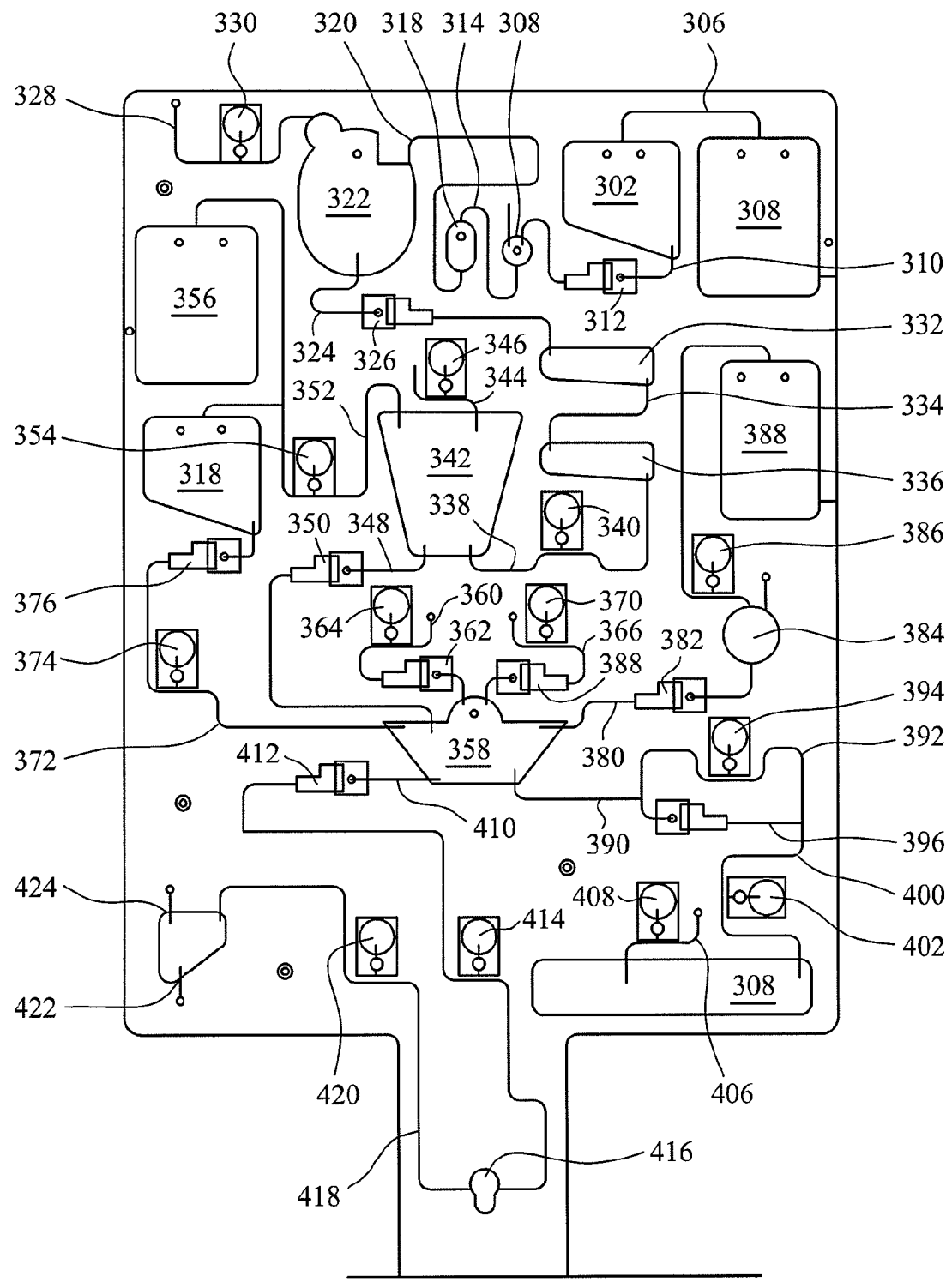
FIG. 11a is a front face view of part of a cartridge embodying the present invention.

FIG. 11a is an illustration of that part of the sample receiving step 200 provided on the cartridge 9, the whole sample preparation step 202 and the whole sample amplification step 204. The subsequent steps and their respective pasts of the cartridge 9 are illustrated separately.

FIG. 11b provides details of the volumes of the various chambers used, the depths (into the page in effect) for the various components and the overall dimensions of this part of the cartridge 9.

The cartridge 9 is provided with a sample introduction chamber 302 connected to a channel 304 leading to the outside of the cartridge 300. This forms those parts of the sample receiving step 200 provided on the cartridge 9.

The sample preparation step 204 follows. To provide this, the sample introduction chamber 302 is connected to a pumping fluid channel 306 and hence to a first electrochemical pump 308. The sample introduction chamber 302 has an outlet channel 310 which passes valve 312 and provides an inlet to purification buffer chamber 314. Valve 312 is initially open.

Purification buffer chamber 314 is connected via channel 316 to bead storage chamber 318. The bead storage chamber 318 is connected via channel 320 to initial mixing chamber 322. The outlet channel 324 from initial mixing chamber 322 is blocked by closed valve 326, but a vent channel 328 is open because valve 330 is open initially.

The outlet channel 324 leads past valve 326 to a first further mixing chamber 332 and then through channel 334 to second further mixing chamber 336. The outlet 338 from the second further mixing chamber 336 leads past valve 340 to incubation chamber 342, where bubble mixing assists the DNA to bead binding process.

The incubation chamber 342 has a vent channel 344 provided with valve 346 and an outlet channel 348 which is initially closed by valve 350. The incubation chamber 342 is also provided with a pumping fluid inlet channel 352 which passes valve 354 and is connected to second electrochemical pump 356.

The outlet channel 348 from the incubation chamber 342 leads to capture chamber 358 where the beads and hence bound DNA are collected. The capture chamber 358 is provided with a first vent channel 360 which passes first valve 362 and second valve 364. The capture chamber 358 is also provided with a second vent channel 366 which passes first valve 368 and second valve 370.

Also connected to capture chamber 358 is wash buffer channel 372. The wash buffer channel is connected to first valve 374 and second valve 376 and leads from second electrochemical pump 356 through wash buffer chamber 378 to the capture chamber 358.

Also connected to capture chamber 358 is an elution liquid channel 380. The elution liquid channel 380 is connected to first valve 382, elution liquid storage chamber 384, second valve 386 and back to third electrochemical pump 388.

The capture chamber 358 has a wash outlet channel 390 which splits into a first wash outlet channel section 392 which passes valve 394, and into a second wash outlet channel section 396 which passes valve 398. After passing their respective valves 394, 398, the first wash outlet channel section 392 and second wash outlet channel section 396 rejoin one another to form further wash channel 400. The further wash channel 400 leads past valve 402 into waste chamber 404. The waste chamber 404 is vented along vent channel 406 past valve 408. These elements provide the sample preparation step 202.

To provide the sample amplification step 204, capture chamber 358 is also provided with elution outlet channel 410 which leads past valve 412 and past valve 414 and into PCR chamber 416. The outlet channel 418 from the PCR chamber 416 leads past valve 420 into archive chamber 422. The archive chamber 422 is vented through vent channel 424. The role of the archive chamber 422 is described further below.

Provided within the PCR chamber 416 is a bead loaded with the reagents, a multimix, needed for the PCR process. The reagents/multimix include primers dNTPs and PCR reaction mix, including Tris buffer, $MgCl_2$, NaCl and BSA. These reagents are released into the sample once it contacts the bead in the PCR chamber 416 and the temperature is raised above ambient temperature.

The above circuit overall, is sufficient to receive, retain, wash, elute and perform PCR on the sample, as well as storing the waste from the process and an archive of the PCR product.

Subsequently, the arrangement shown in FIG. 12 can be used to transfer the now amplified DNA from the PCR chamber 416 into the electrophoresis step 206.

Figure 12:
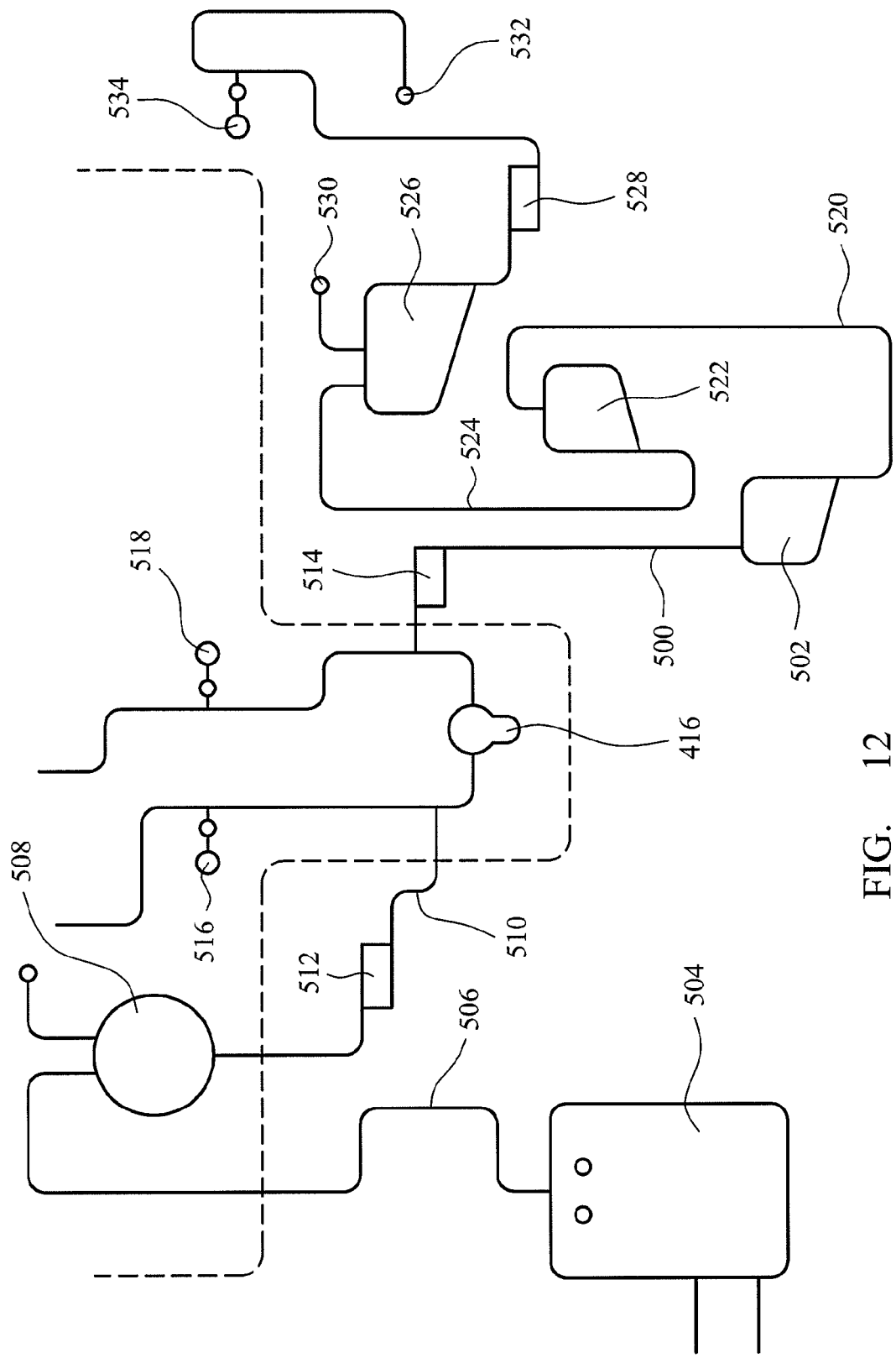
FIG. 12 is a front face view of a further part of the cartridge of FIG. 11a and embodying further features of the present invention.

In FIG. 12, the PCR chamber 416 is the same PCR chamber 416 which was illustrated in FIG. 11a and described above. Other features were omitted from FIG. 11a to improve the clarity of that Figure.

Leading from the PCR chamber 416 is a denaturing feed channel 500 which is connected to an amplified material mixing chamber 502. The amplified material is pumped from PCR chamber 416 by the action of fourth electrochemical pump 504 which is connected to channel 506, hence to denaturing reagent storage chamber 508 and through channel 510 to the PCR chamber 416. Formamide is provided in the denaturing reagent storage chamber in the preferred form.

These components are isolated from the PCR chamber 416 during the sample amplification step 204 by closed valve 512 and closed valve 514. Both valve 512 and 514 are opened and valves 516 and 518 are closed to convey the amplified material away from the PCR chamber 416.

From the denaturing feed channel 500, the amplified material and denaturing reagents enter the first amplified material mixing chamber 502, pass through channel 520, into second amplified material mixing chamber 522, through channel 524 and into third amplified material mixing chamber 526. Whilst the third amplified material mixing chamber 526 fills, valve 528 is shut and vent 530 is open. An overall volume of 45:1 is provided, 5:1 from the PCR chamber and 40:1 from the denaturing reagent storage chamber 508.

The amplified material is held in the third mixing chamber 526 for the necessary time and at the necessary temperature to complete the denaturing process. Once this has been achieved, the valve 528 is opened and further pumping by the fourth electrochemical pump 504 pumps the denatured material to the electrophoresis step inlet 532. At the inlet 532, the denatured material passes out of the plane of the cartridge 9 and to the electrophoresis cartridge section behind. Once past through the inlet 532, valve 534 is shut to isolate the cartridge 9 from the electrophoresis cartridge section 600.

The overall result of this structure is the pumping of the amplified DNA to a start point for the electrophoresis step 206.

The transfer from PCR to CE steps is provided in a way which allows easy integration of the steps, does not impact upon the temperature and pressure stability required in PCR and achieves minimal sample loss during transfer. Automated mixing of the sample and size standards during transfer and possibilities for pre-concentrating the sample before CE are also rendered possible.

Figure 13A:
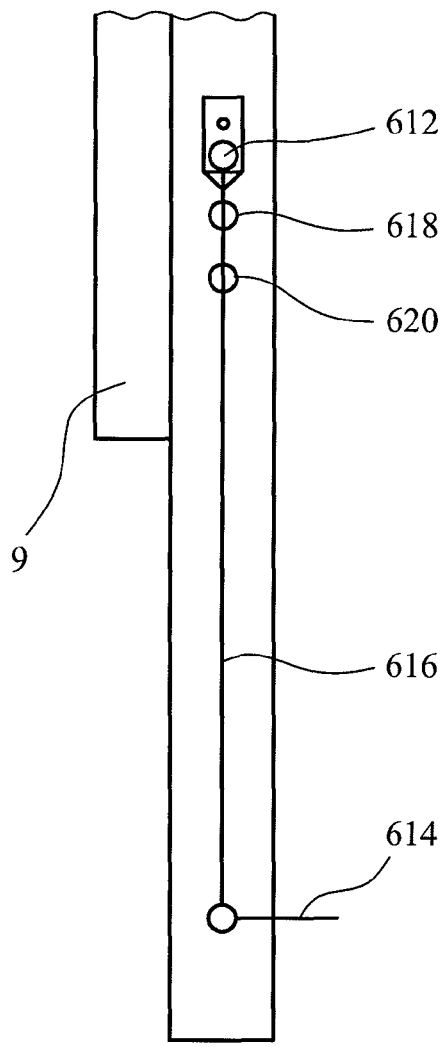
FIG. 13a is a side view of the section of the cartridge of FIGS. 11a and 12 where in joins the electrophoresis cartridge section.
Figure 13B:
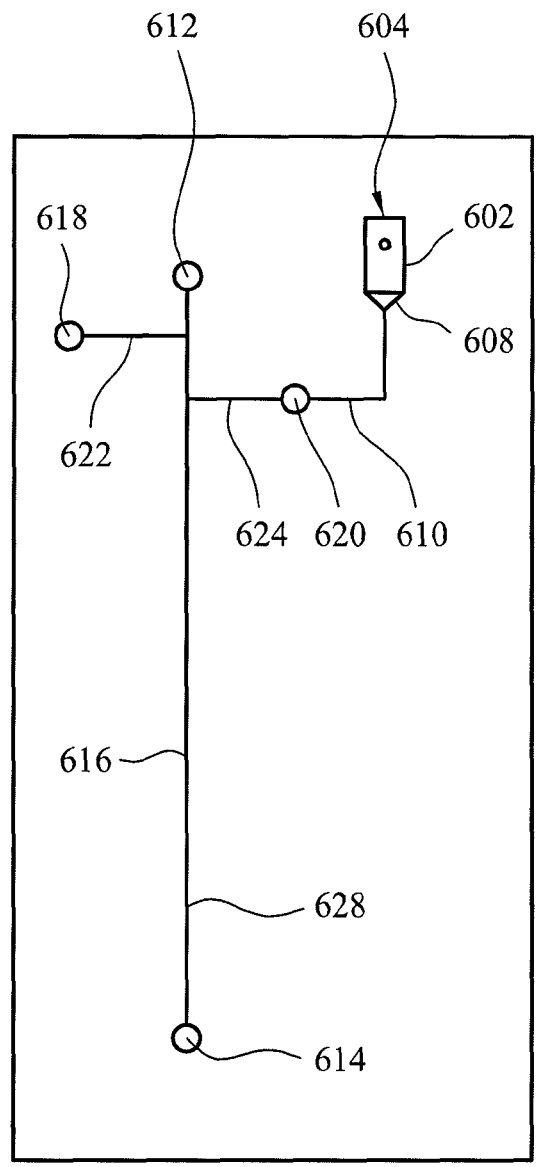
FIG. 13b is a front view of the electrophoresis cartridge section shown in FIG. 13a, with the section of the cartridge omitted.

The overall configuration of the electrophoresis step 206 can be seen in the side view of FIG. 13a and front view of FIG. 13b.

The inlet 532 leads from the plane of the cartridge 9, through into the plane of the electrophoresis cartridge section 600. Here, the inlet 532 leads into the top section 602 of an electrophoresis feed reservoir 604. The top section 602 is empty, but the lower section 606 is provided with the gel 608 which also fills the capillary 610. The sample is pumped into the electrophoresis feed reservoir 604 by a fourth electrochemical pump, not shown.

Sample flow from the reservoir 604 into the correct position within the capillary 610 is achieved using electrophoresis as the transport mechanism.

In this embodiment, the injector structure provided within the capillary cartridge section 600 is a double T injector. This includes a first electrode location 612, second electrode location 614 provided at the other end of the long capillary 616 in which the size based separation is achieved. A third electrode location 618 and fourth electrode location 620 are provided in side arms 622 and 624 respectively. The side arms are offset relative to one another, with side arm 624 further towards the second electrode location 614, than the side arm 622.

Initially, sample is drawn from the liquid phase in the reservoir 604 through the interface with the gel provided in the reservoir 604 and hence into the gel by a voltage applied to the electrode present at the third electrode location 618. Once the sample has been drawn past the fourth electrode location 620, a voltage is also applied to the electrode at the fourth electrode location. Generally, the electrode at the third electrode location may be at a voltage of 600V and the electrode at the fourth electrode location may be at a voltage of 200V. The voltage may be floating for the electrodes at the first 612 and second 614 electrode locations.

This situation results in sample being drawn along side arm 624, along the section 626 and into side arm 622, such that sample is present in the two side arms 622 and 624 and the section 626 of the capillary 616.

This gives the plug of sample upon which the electrophoresis's to act in the section 626.

To reduce the cost of the electrodes used, consistent with the cartridge being single use, platinum coated, gold coated, carbon, nickel and other lower cost electrodes may be used.

Once positioned, the separation voltages are applied: 1500V at the electrode at the second electrode location 614; 0V at the electrode at the first electrode location 612; and 200V at the electrodes present at the third electrode position 618 and fourth electrode positions 620.

The capillary 616 is filled with a gel matrix which preferentially retards the speed of progress of elements within the DNA as their size increases. The result is a size based separation of the elements, with the faster elements reaching the detection location 626 first and the slowest reaching the detection location 628 last. The different times at which the signals are generated and form the electropherogram indicate the size of the element behind that signal.

It is possible to assist in the interpretation of the unknown element sizes by using a size standard within the capillary. This is provided with a different dye colour or otherwise rendered distinct. The method set out in U.S. patent application No. 61/096424, the contents of which are hereby incorporated by reference, offers approaches for determining the sizes of the unknowns from the size standard.

The setup and operation of the light source, optics and detector is described in detail below.

Other embodiments of the cartridge have also been developed.

Figure 14:
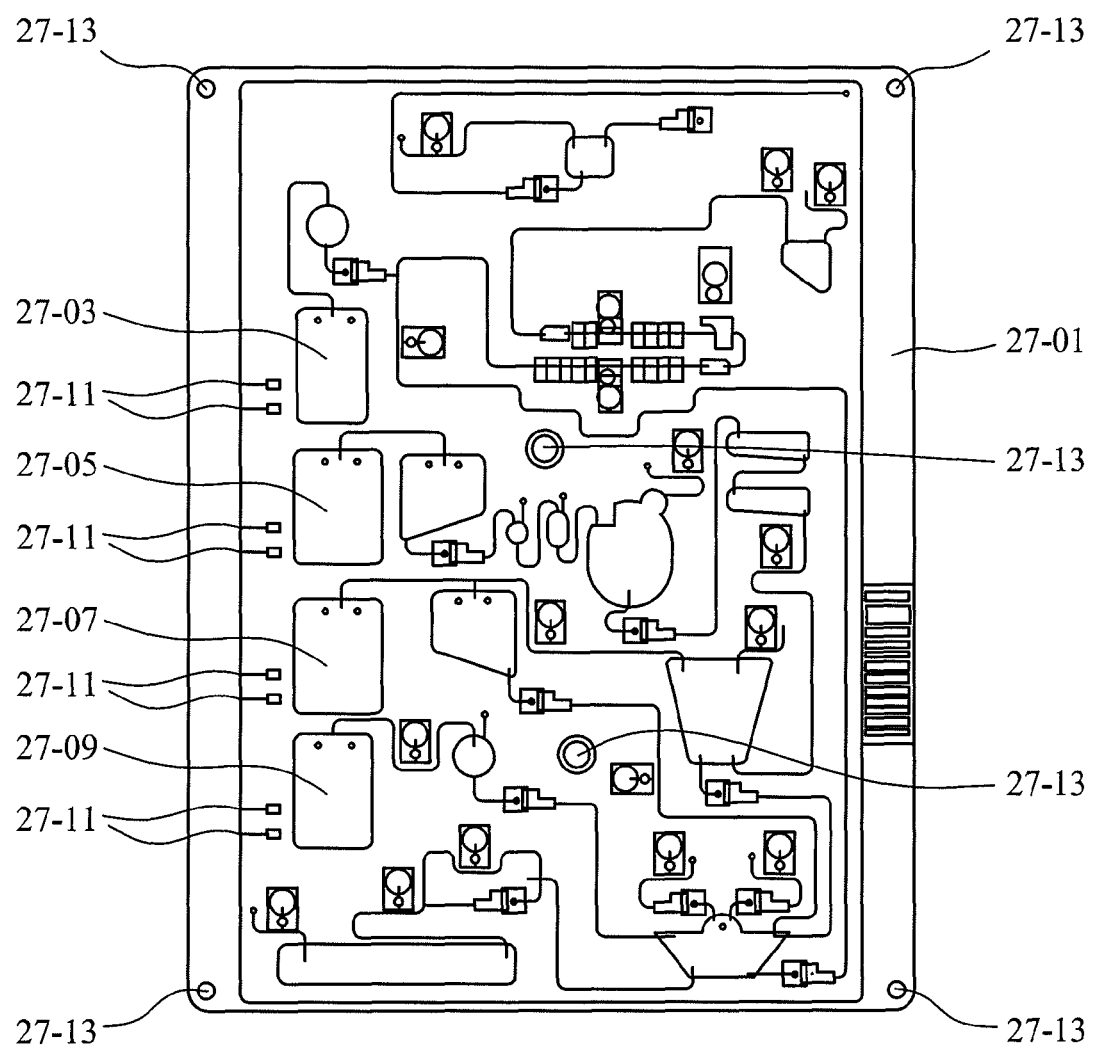
FIG. 14 is a front face view of a cartridge according to an embodiment.

As shown in FIG. 14, the cartridge 27-01 has been modified by providing the electrochemical pumps 27-03, 27-05, 27-07, 27-09 with connections between the wires leading to the electrodes in the pumps and the power source not shown of the Pogo™ pin type. The pins 27-11 are spring loaded in the recesses of the cartridge 27-01 and in use contact similar spring loaded pins (not shown) on the other side of the cartridge to instrument interface. A reliable electrical contact is thus provided and the cartridge is more robust against damage during storage, installation and use than designs in which the wires for the electrochemical pumps protruded from the side of the cartridge.

The form shown in FIG. 14 also features guide holes 27-13 which are used in the alignment of the cartridge and instrument, as described in more detail below.

Figure 15A:
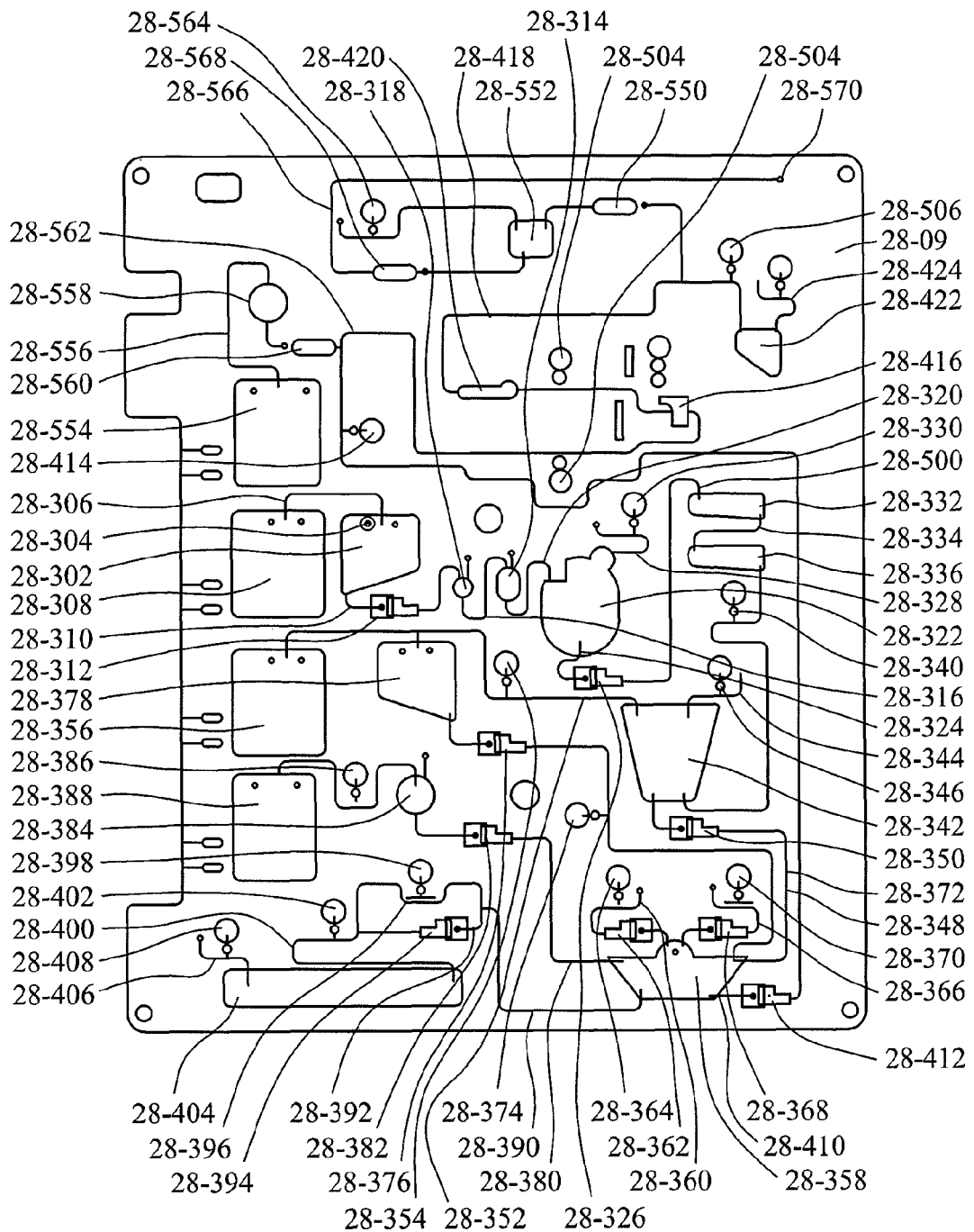
FIG. 15a is a front face view of a cartridge according to a different embodiment.

A preferred embodiment of the cartridge is shown in FIG. 15a. This is an illustration of that part of the sample receiving step 200 provided on the cartridge 28-09, the whole sample preparation step 202, the whole sample amplification step 204, the whole sample denaturation step and the feed to the capillary electrophoresis step 206.

FIG. 15b provides details of the volumes of the various chambers used, the depths (into the page in effect) for the various components and the overall dimensions of this part of the cartridge 28-09.

The cartridge 28-09 is provided with a sample introduction chamber 28-302 connected to a channel 28-304 leading to the outside of the cartridge 28-09. This forms those parts of the sample receiving step 200 provided on the cartridge 28-09.

The sample preparation step 204 follows. To provide this, the sample introduction chamber 28-302 is connected to a pumping fluid channel 28-306 and hence to a first electrochemical pump 28-308. The sample introduction chamber 28-302 has an outlet channel 28-310 which passes valve 28-312 and provides an inlet to bead storage chamber 28-318. Valve 28-312 is initially open.

The bead storage chamber 28-318 has an outlet channel 28-316 leading to binding buffer storage chamber 28-314. This sequence of chambers is reversed compared with the FIG. 3a embodiment. The binding buffer storage chamber 28-314 has an outlet channel 28-320 which leads to mixing/purification chamber 28-322.

Mixing/purification chamber 28-322 is connected via channel 28-324 through valve 28-326 and via channel 28-500 to first further mixing chamber 28-332. The outlet channel 28-324 from mixing/purification chamber 28-322 is blocked by closed valve 28-326, but a vent channel 28-328 is open because valve 28-330 is open initially.

The outlet channel 28-324 leads past valve 28-326 to a first further mixing chamber 28-332 and then through channel 28-334 to second further mixing chamber 28-336. The outlet 28-338 from the second further mixing chamber 28-336 leads past valve 28-340 to incubation chamber 28-342, where bubble mixing assists the DNA to bead binding process. The incubation chamber 28-342 may be actively heated or may simply provide the necessary dwell time and/or other binding conditions needed.

The incubation chamber 28-342 has a vent channel 28-344 provided with valve 28-346 and an outlet channel 28-348 which is initially closed by valve 28-350. The incubation chamber 28-342 is also provided with a pumping fluid inlet channel 28-352 which passes valve 28-354 and is connected to second electrochemical pump 28-356.

The outlet channel 28-348 from the incubation chamber 28-342 leads to capture chamber 28-358 where the beads and hence bound DNA are collected. The capture chamber 28-358 is provided with a first vent channel 28-360 which passes first valve 28-362 and second valve 28-364. The capture chamber 28-358 is also provided with a second vent channel 28-366 which passes first valve 28-368 and second valve 28-370.

Also connected to capture chamber 28-358 is wash buffer channel 28-372. The wash buffer channel is connected to first valve 28-374 and second valve 28-376 and leads from second electrochemical pump 28-356 through wash buffer chamber 28-378 to the capture chamber 28-358.

Also connected to capture chamber 28-358 is an elution liquid channel 28-380. The elution liquid channel 28-380 is connected to first valve 28-382, elution liquid storage chamber 28-384, second valve 28-386 and back to third electrochemical pump 28-388.

The capture chamber 28-358 has a wash outlet channel 28-390 which splits into a first wash outlet channel section 28-392 which passes valve 28-394, and into a second wash outlet channel section 28-396 which passes valve 28-398. After passing their respective valves 28-394, 28-398, the first wash outlet channel section 28-392 and second wash outlet channel section 28-396 rejoin one another to form further wash channel 28-400. The further wash channel 28-400 leads past valve 28-402 into waste chamber 28-404. The waste chamber 28-404 is vented along vent channel 28-406 past valve 28-408. These elements provide the sample preparation step 202.

To provide the sample amplification step 204, capture chamber 28-358 is also provided with elution outlet channel 28-410 which leads past valve 28-412 and past valve 28-414 and past valve 28-502 and into PCR chamber 28-416. The outlet channel 28-418 from the PCR chamber 28-416 leads past valve 28-420 and past valve 28-504 and past valve 28-506 into archive chamber 28-422. The archive chamber 28-422 is vented through vent channel 28-424. The role of the archive chamber 28-422 is as described further above.

Provided within the PCR chamber 28-416 is a bead loaded with the reagents, a multimix, needed for the PCR process. The reagents/multimix include primers dNTPs and PCR reaction mix, including Tris buffer, $MgCl_2$, NaCl and BSA. These reagents are released into the sample once it contacts the bead in the PCR chamber 28-416 and the temperature is raised above ambient temperature.

The above circuit overall, is sufficient to receive, retain, wash, elute and perform PCR on the sample, as well as storing the waste from the process and an archive of the PCR product.

The PCR part of the circuit has been moved to the upper section of the cartridge compared with the previous embodiments so as to present it physically closer to the CE chip.

Subsequently, the further arrangement shown in FIG. 15a can be used to prepare, denaturation step, and transfer the now amplified DNA from the PCR chamber 28-416 into the electrophoresis step 206.

Leading from the PCR chamber 28-416 is outlet channel 28-418. This splits after valves 28-420 and 28-504 into a denaturing feed channel 28-550 and the channel leading to the archive chamber 28-422. The denaturing feed channel 28-550 is connected to a denaturation chamber 28-552. The amplified material is pumped from PCR chamber 28-416 by the action of fourth electrochemical pump 28-554 which is connected to channel 28-556, hence to denaturing reagent storage chamber 28-558 and through valve 28-560 and channel 28-562 to the PCR chamber 28-416. Formamide is provided in the denaturing reagent storage chamber 28-558 in combination with the size standards to be used in the capillary electrophoresis step.

These components are isolated from the PCR chamber 28-416 during the sample amplification step 204 by closed valve 28-502 and closed valve 28-420. Both valve 28-502 and 28-420 are opened and valves 28-414 and 28-506 are closed to convey the amplified material away from the PCR chamber 28-416 to the denaturation chamber 28-552. This is vented through valve 28-564, with exit channel 28-566 closed by valve 28-568.

The amplified material is held in the denaturation chamber 28-552 for the necessary time and at the necessary temperature to complete the denaturing process. Once this has been achieved, the valve 28-568 is opened and further pumping by the fourth electrochemical pump 28-554 pumps the denatured material to the electrophoresis step inlet 28-570.

At the inlet 28-570, the denatured material passes out of the plane of the cartridge 9 and through a tube to the electrophoresis cartridge section behind. The overall result of this structure is the pumping of the amplified DNA to a start point for the electrophoresis step 206.

Details of the connection of the inlet 28-570 to the CE chip are provided above.

Throughout the operations described above and in the sections that follow, various checks are made on operating conditions, component performance and successful operation so as to ensure the processing is correctly provided from start to finish. Errors or problems are indicated to the operator.

Cartridge Components

Within the cartridge are a significant number of components, with each being optimised with respect to its role and its role in combination with the other components.

1) Valves

Figure 16A:
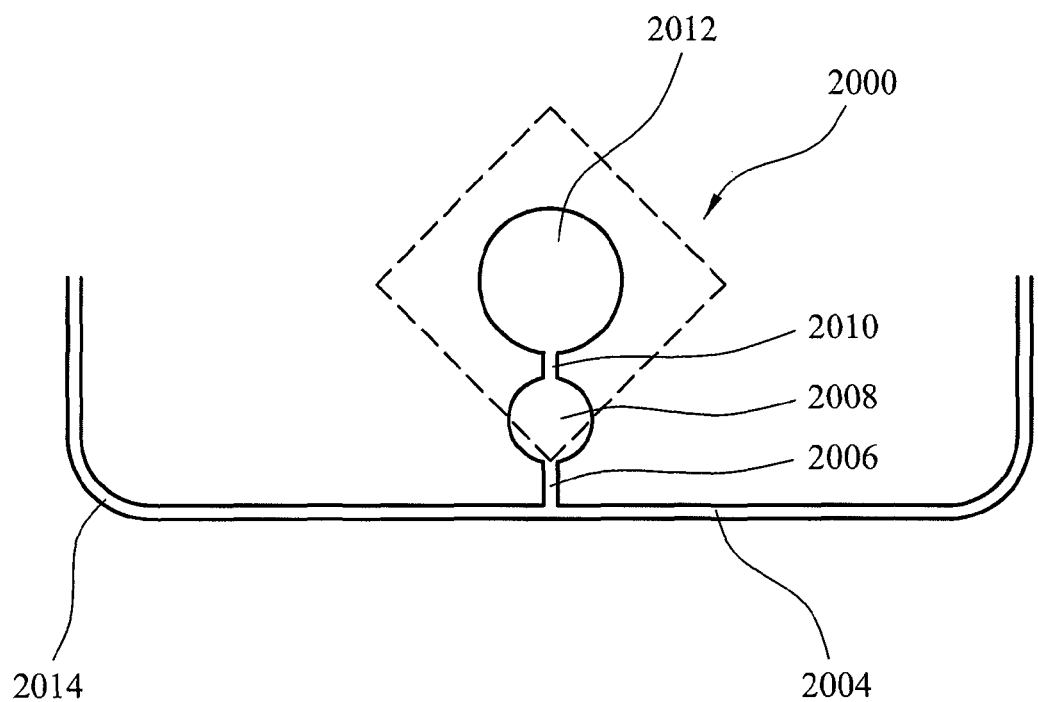
FIG. 16a is an illustration of a closing valve used in the present invention.
Figure 16B:
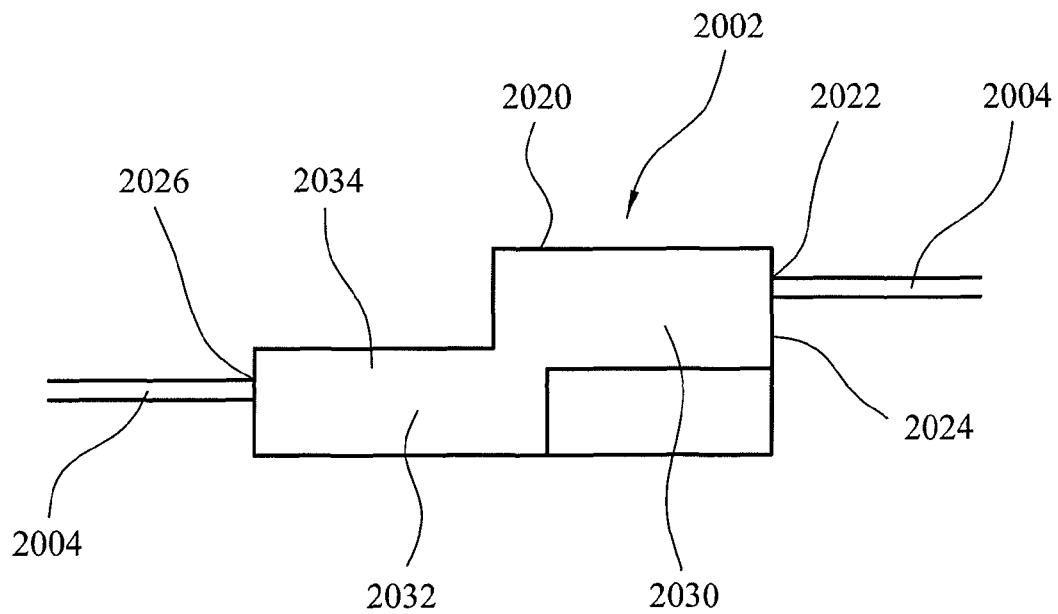
FIG. 16b is an illustration of an opening valve used in the present invention.

To minimise manufacturing costs and give consistent operation, all of the valves in the cartridge are one of two types. The two types are a closing valve 2000; FIGS. 16a; and an opening valve 2002; FIGS. 16b.

The closing valve 2000 is shown schematically in FIG. 16a. The closing valve 2000 is positioned above, relative to the direction of gravity, the channel 2004 to be closed. The closing valve 2000 is formed by a conduit 2006 which is in fluid communication with the channel 2004 and is in fluid communication with the bottom of a valve reservoir 2008. The valve reservoir 2008 is filled with paraffin wax and is 3 mm in diameter and is provided with the conduit 2006. On the top of the valve reservoir 2008, a gas passage 2010 provides fluid communication with a valve gas reservoir 2012. The valve gas reservoir 2012 is full of air.

The dotted line in FIG. 16a shows that part of the location of the closing valve 2000 which is in contact with a heater element, not shown, provided on the adjoining printed circuit board of the instrument.

When the closing valve 2000 is to be activated, the heater element is caused to heat up. This both melts the paraffin wax in the valve reservoir 2008 and causes the air in the valve gas reservoir 2012 to expand. The expansion of the air provides the driving force to displace the melted paraffin wax from the valve reservoir 2008 into the conduit 2006 and then into the channel 2004.

The volume of paraffin wax displaced is controlled by the temperature to which the valve gas reservoir 2012 is heated (variation in pressure) and the duration of the heating applied (as the paraffin wax soon solidified once the heating is switched off).

Continued displacement of the paraffin wax into the channel 2004 causes the paraffin wax to expand in each direction along the channel 2004.

In some cases, the fluid in the channel will not compress or move in one direction (or is limited in the extent possible) and so the flow of the paraffin wax within the channel 2004 occurs preferentially in the other direction. Normally, the paraffin wax is displaced into the channel 2004 until a 2 mm to 10 mm length of the channel 2004 is filled. With the heat removed, the paraffin wax sets in this new position and the channel 2004 is reliably sealed.

The section where the channel 2004 is to be shut, is deliberately chosen to be horizontal, relative to the direction of gravity, as this assists the retention of the paraffin wax at the location to be sealed.

To assist further in the formation of the seal, it is beneficial to arrange the closing valve so that it is between one or two upward, relative to the direction of gravity, bends. As shown in FIG. 16a the bend 2014 provides assistance in the accurate formation of the seal within the channel 2004.

The opening valve 2002 is shown schematically in FIG. 16b. The opening valve 2002 is positioned as a part of the channel 2004 the fluid flows through. The opening valve 2004 is formed by a valve chamber 2020 which has an inlet 2022 from the channel 2004 in a first side wall 2024 and an outlet 2026 leading to the continuation of the channel 2004 in the opposing side wall 2028.

The paraffin wax is positioned in the initial section 2030 of the valve chamber 2020. Downstream of this initial section 2030, is a trap section 2032. The dotted line in FIG. 10b shows that part of the opening valve 2002 which is in contact with a heater element, not shown, provided on the adjoining printed circuit board of the instrument.

When the opening valve 2002 is to be activated, the heater element is caused to heat up. This melts the paraffin wax in the initial section 2030. By the time the paraffin is melted, or shortly thereafter, an electrochemical pump upstream of the opening valve 2002 has been activated for sufficient time to cause a pressure build up, upstream of the opening valve 2002. This pressure causes the driving force to displace the melted paraffin wax from the initial section 2030 and downstream into the trap section 2032. Once in the trap section 2032, the passage 2034 above the paraffin wax is clear allowing fluid communication through the opening valve.

With the heat removed, the paraffin wax sets in this new position and the channel 2004 and passageway 2034 is reliably opened.

The section where the channel 2004 is to be opened is deliberately chosen to be horizontal, relative to the direction of gravity, as this assists the retention of the paraffin wax in the trap section 2032.

In some applications, particularly those close to the high temperatures used in the PCR chamber, the valves benefit from using a high melting point wax. This melts at greater than 95° C. and so does not melt under PCR conditions. In some cases, the valve performance can be improved further by using a high melting point and lower melting point mixture; with the lower melting point wax tending to fill any cracks which form in the higher melting point wax.

2) Electrochemical Pumps

To simplify the construction and costs of the cartridge, a common approach is used to providing the motive power to the various operations on the cartridge; gas fluidic driving devices, which use gas to provide motive power, for example electrochemical pumps. Each of the electrochemical pumps consists of a pair of electrodes immersed in the electrolyte. The flow of a current results in off gassing. The off gas collects in the top of the electrochemical pump, increases in pressure and leaves the pump via the outlet in the top of the pump. This off gas pushes ahead of itself other fluids encountered in the channels and chambers. The off gas contributes to bubble mixing in some of the stages.

To give a desired extent of pumping, the volume of the electrochemical pump can be varied. The extent of pumping can be delivered in one, two or more goes, as turning off the current stops the pumping action.

The rate of pumping and/or pressure delivered can be varied by varying the molarity of the electrolyte. Sodium chloride is the preferred electrolyte; used at 1M; and used in conjunction with aluminium electrodes.

Electrophoresis Components

1) Optics

In the electrophoresis step 206, at the detection location 628, light from a laser 800 is focussed to be incident upon the fluorescent dye associated with a DNA element to make it detectable.

A different dye is used for each different DNA element type; a type is generally associated with a given locus.

Figure 17:
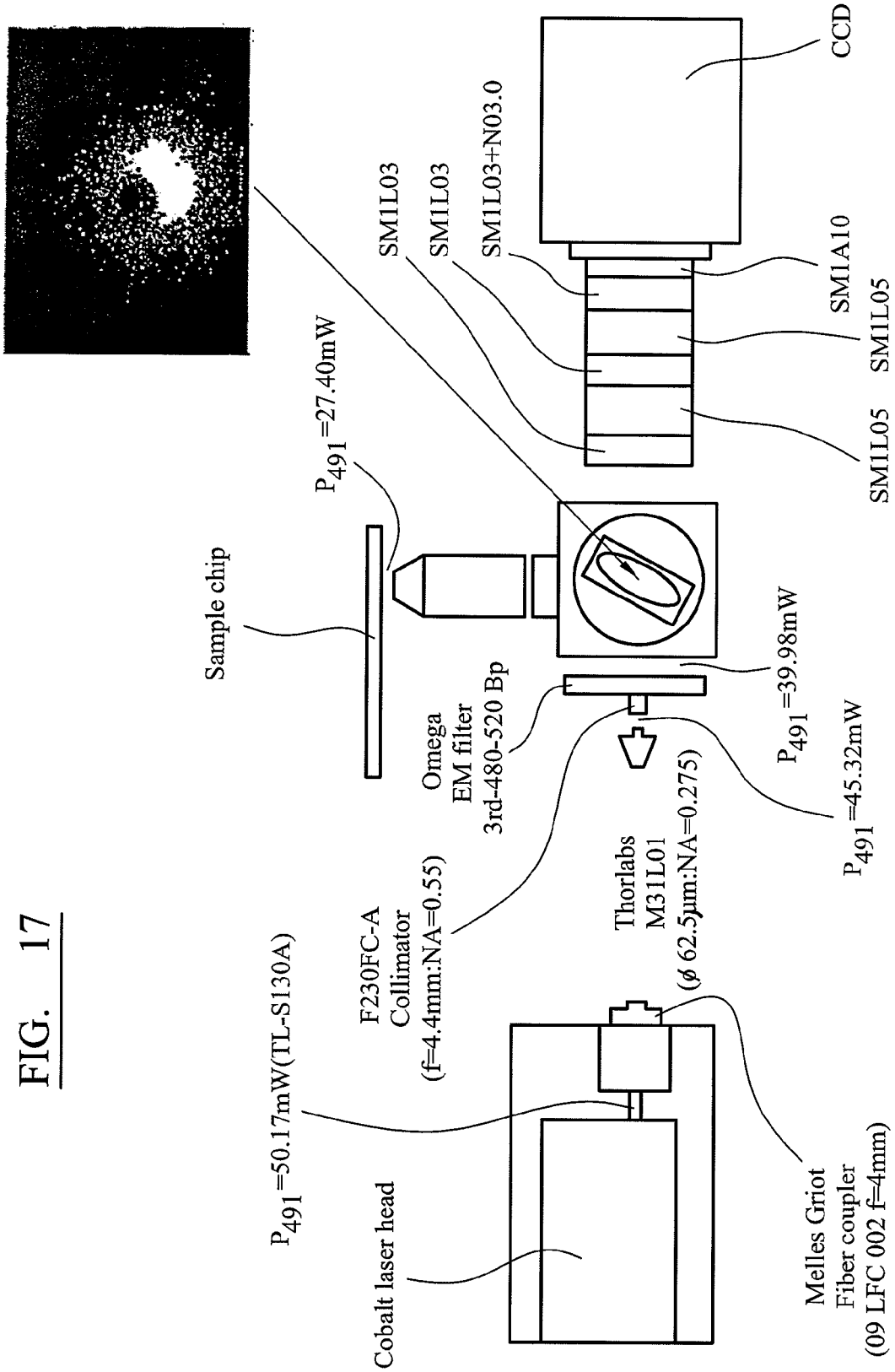
FIG. 17 is a schematic of the light source, optics and detector setup for the electrophoresis section of the instrument.

To get good sensitivity, it is important for the incident light to be of sufficient intensity for the detectors to receive sufficient light to be sensitive to the emitted fluorescent light, but for the intensity not to be so high as to give rise to photobleaching of the dyes. To provide for this, the following arrangement is used; FIG. 17.

The light source is a compact laser 900 which is mounted on a heat sink 902. The laser 900 is a Cobolt Calypso laser (from Cobolt AB, Kraftriken 8, SE-104 05, Stockholm, Sweden) and emits at 491 nm with a maximum power of 50 mW. The light emitted by the laser 900 is fed to a fibre coupler 904 (09 LFC 001, f=3.5 mm from Melles Griot, 2051 Palomar Airport Road, 200, Carlsbad, Calif. 92011, USA) and hence into an patch cable assembly (M31L01, from Thorlabs, 435 Route 206 North, Newton, N.J., 07860, USA) and optical fibre 906 (GIF625, dia 62.5:m, NA=0.275 from Thorlabs, 435 Route 206 North, Newton, N.J., 07860, USA).

The use of the optical fibre 906 is beneficial as it safely controls the laser light direction, enables the laser light to be easily conveyed to the position of use and enables mechanical stability to be provided within the overall system. At the end of the optical fibre 906 a power of up to 45.32 mW is still observed.

The laser light then passes through a collimator 908 (F230FC-A, F=4.5 mm, NA=0.55, from Thorlabs) and a log-pass filter with a sharp cut-off wavelength, EM filter (Omega Optical XF3093, T50=515 nm) before reaching the spot mirror 910.

The spot mirror 910 is used to both direct the laser light to the detection location 628 of the capillary and to transmit, anisotropically and without filtering, the fluorescent light received there from to the detector unit. It is angled at 45° to the beam of laser light. To do this, the reflector 910 consists of a 25 mm round glass disc which transmits all light from <80 above 380 nm. An ellipse, 2 mm long by 1 mm wide, is provided at the centre of the reflector 910 (so as to present an effective 1 mm circular mirror), formed of a highly reflective mirror layer deposited there (reflectivity of 99.99%).

Before reaching the detection location 628, the laser light passes through a focussing lens 912. This can be a microscope optic or other such adjustable focussing lens. Such optics are useful as they introduce no optical aberrations to the light, shape the beam for application to the detection location 628 and don't give any selective loss of light colours. The power reaching the detection location 628 is over 27.40 mW.

The fluorescent light is effectively scattered from the dye in the capillary 616 in all directions. For the fluorescence light to reach the detector unit, that light needs to hit the spot mirror 910 at a location outside of the glass spot. If it does so, the light is transmitted into the detector unit 914.

The detector unit 914 includes a slit in front of a spectrometer to obtain diffraction-limited incident light, the spectrometer provided with a diffraction grating and a lens 918 (LA1608A plano convex, f=50 mm, D=25 mm, with anti-reflective coating within 350-650 nm, made of BK7 glass, Thorlabs Inc), to direct the light to the charge coupled device 916. The CCD 916 has spectroscopic abilities.

In an alternative approach, certain problems with the stability of the fibre optics can be avoided by providing an open beam approach to delivering the light from the laser to the channel.

Figure 18:
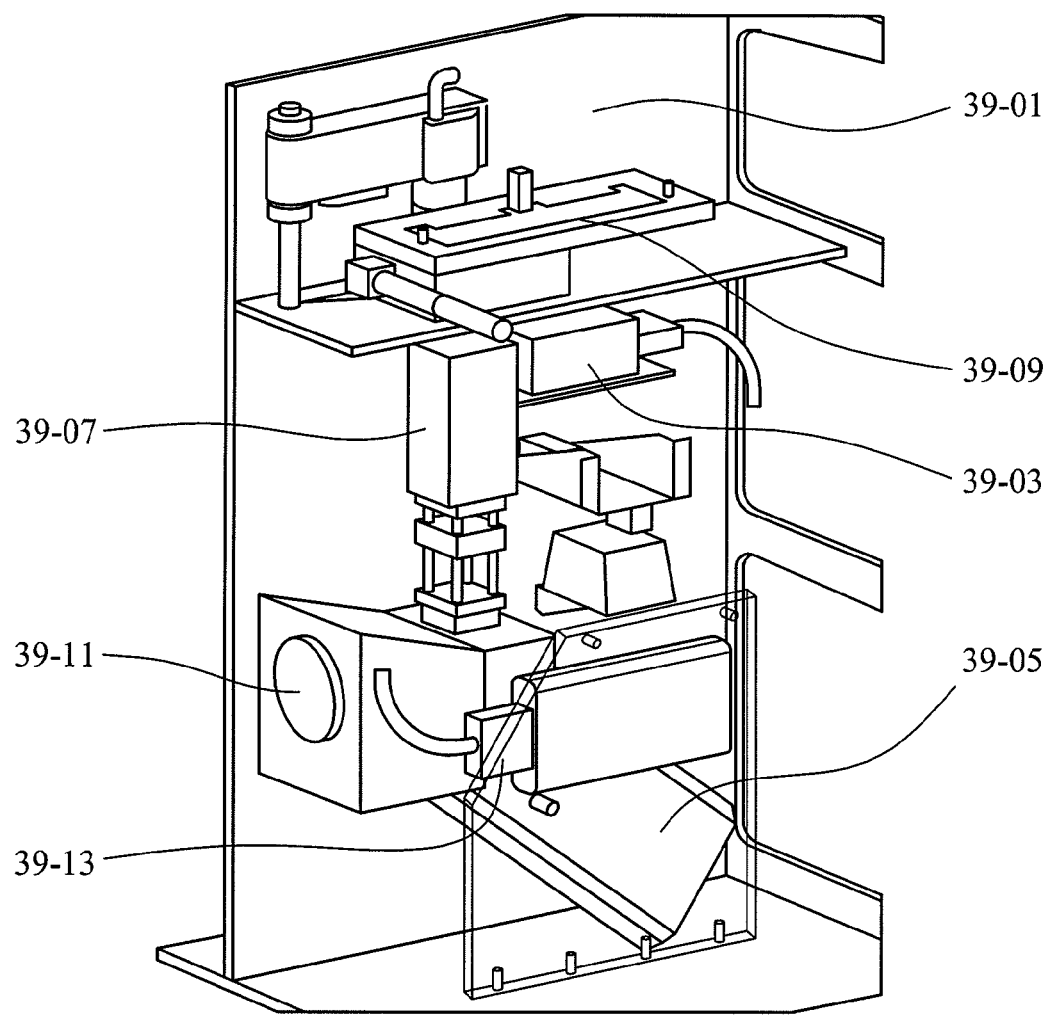
FIG. 18 is a perspective view of an embodiment of the optics.

An alternative embodiment of the optics is shown in the cut away perspective view of FIG. 18. The instrument casing 39-01 provides various mounts for the optics. The light is generated by the laser head 39-03 operated under control by the laser controller 39-05. The light enters the optics 39-07 and is directed at the channel in the CE chip, not shown, mounted in the CE chip heater board 39-09.

The return light enters the optics 39-07 and is directed back to the spectrometer 39-11 and CCD camera 39-13. Above the CE chip heater board 39-09 is the chip alignment structure 39-15 which is described further below.

Figure 30A:
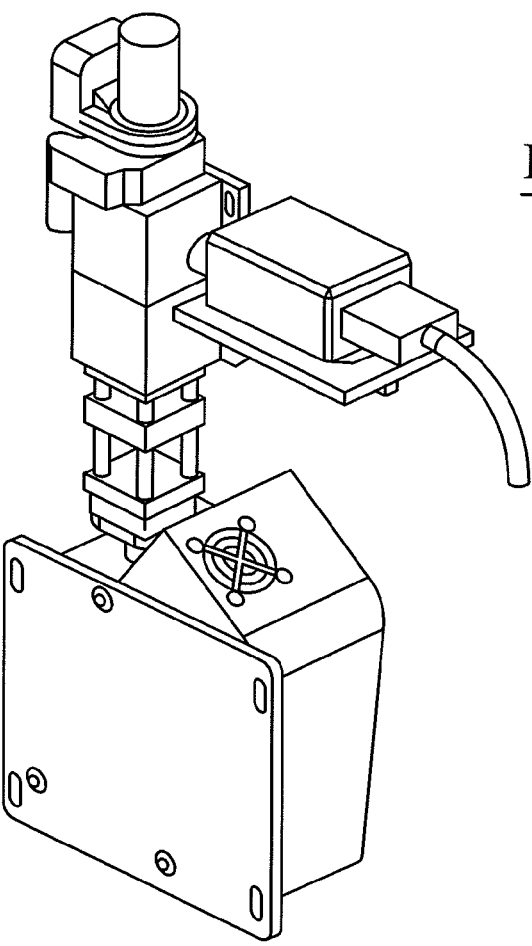
FIGS. 30A and 30B depict perspective and exploded views, respectively, of an optics system assembly for use in an embodiment of the invention.
Figure 30B:
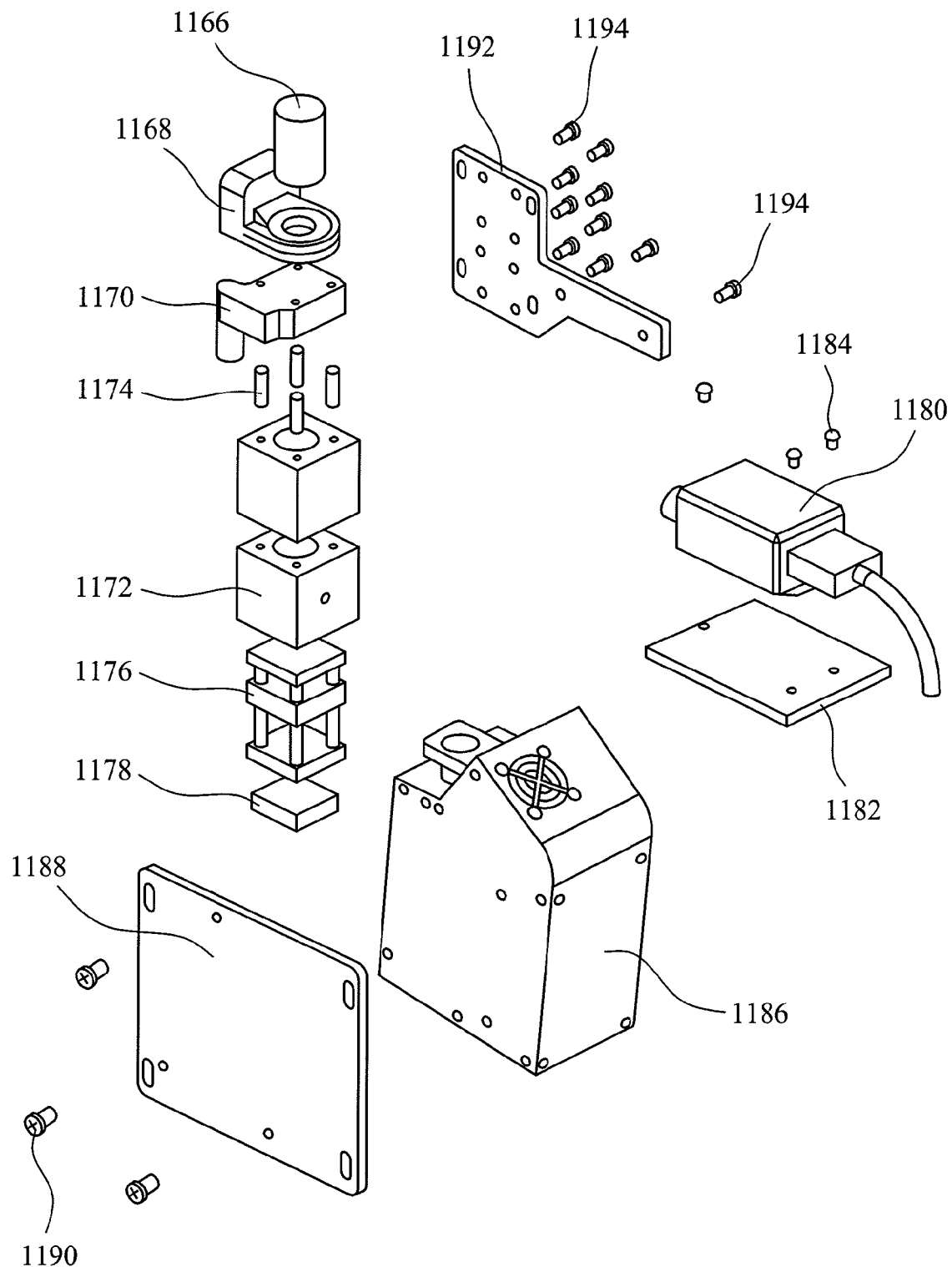

An alternative embodiment of the optics assembly is depicted in perspective view in FIG. 30A and in exploded view in FIG. 30B. The optics stack comprises an objective lens 1166 provided above a focussing stage 1168. Focussing stage 1168 is mounted on Z translator 1170 for adjustment about the z axis. Z translator 1170 is mounted on optics cube 1172 via rods 1174. Optics cube 1172 is in turn mounted on x-y alignment 1176 for adjustment about the x and y axes. A slit housing 1178 is provided at the bottom of the optics stack.

A laser head assembly 1180, which includes the laser source is mounted on the optics stack by bracket 1182 and screws 1184. A CCD spectrometer assembly 1186 is mounted under the optics stack. A CCD mounting bracket 1188 is affixed the to CCD spectrometer assembly by screws 1190. An optics mounting bracket 1192 is also provided and secured by screws 1194.

The focussing stage 1168 includes piezo-electric actuators. In use, the piezo electric actuators are adjusted to focus the laser.

2) Electrophoresis Environment Control

For the necessary resolution to be obtained in the electrophoresis step 206, the temperature of the capillary 616 and its contents need to be carefully controlled at the optimum temperature. In the present embodiment, the electrophoresis cartridge section is in contact with a thermally conductive block, with a series of resistance heaters provided on the opposing side of the block. These are provided with controllers and are capable of maintaining the temperature of the electrophoresis cartridge section at the optimum temperature +/−0.3° C.

In addition, the cavity that the electrophoresis cartridge section is provided in is thermostatically controlled at the optimum temperature. This reduces still further temperature variation before, during and after use.

The use of a CE chip heating bed, and raised surface around it, is beneficial in controlling the temperature within the CE chip. The nest so formed ensures consistent positioning and good contact.

Magnet Stage Mechanical Construction

As discussed above, some embodiments include a mechanical mechanism to move a magnet relative to a sample cartridge to allow control of a magnetic field experienced by a portion of the sample cartridge. This field is used in conjunction with magnetic beads provided in the sample cartridge.

Figure 31A:
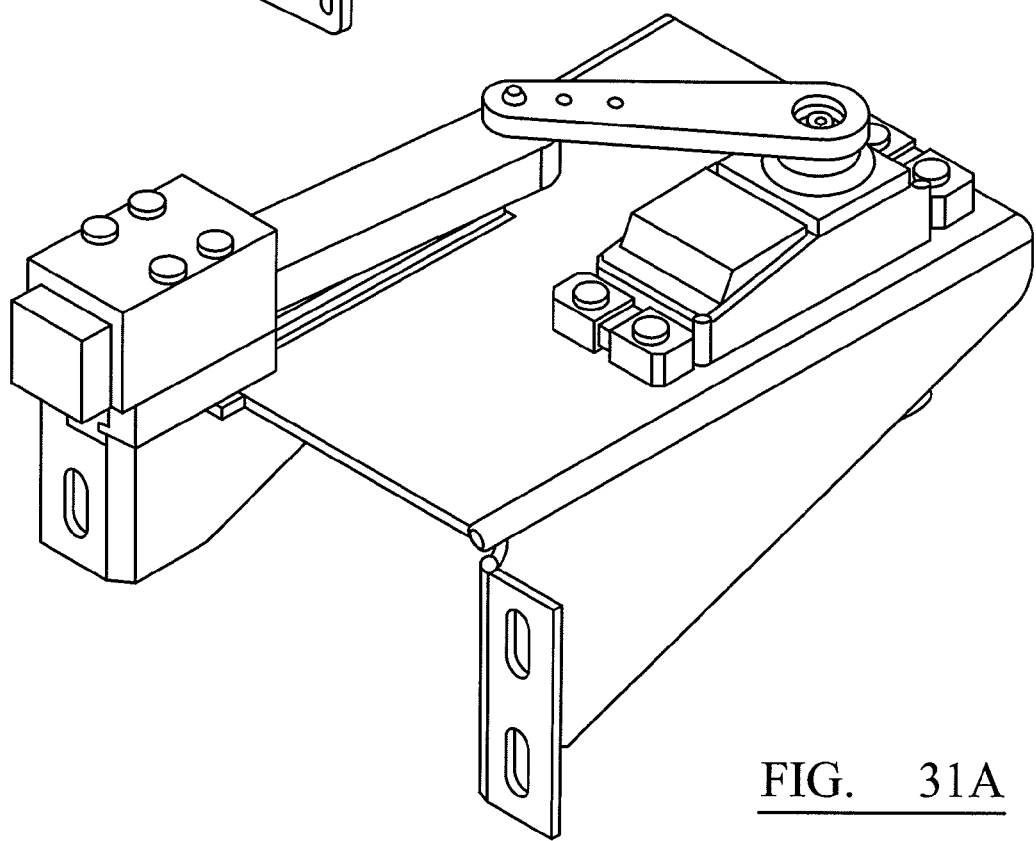
FIGS. 31A and 31B depict perspective and exploded views, respectively, of a magnet assembly for use in an embodiment of the invention.
Figure 31B:
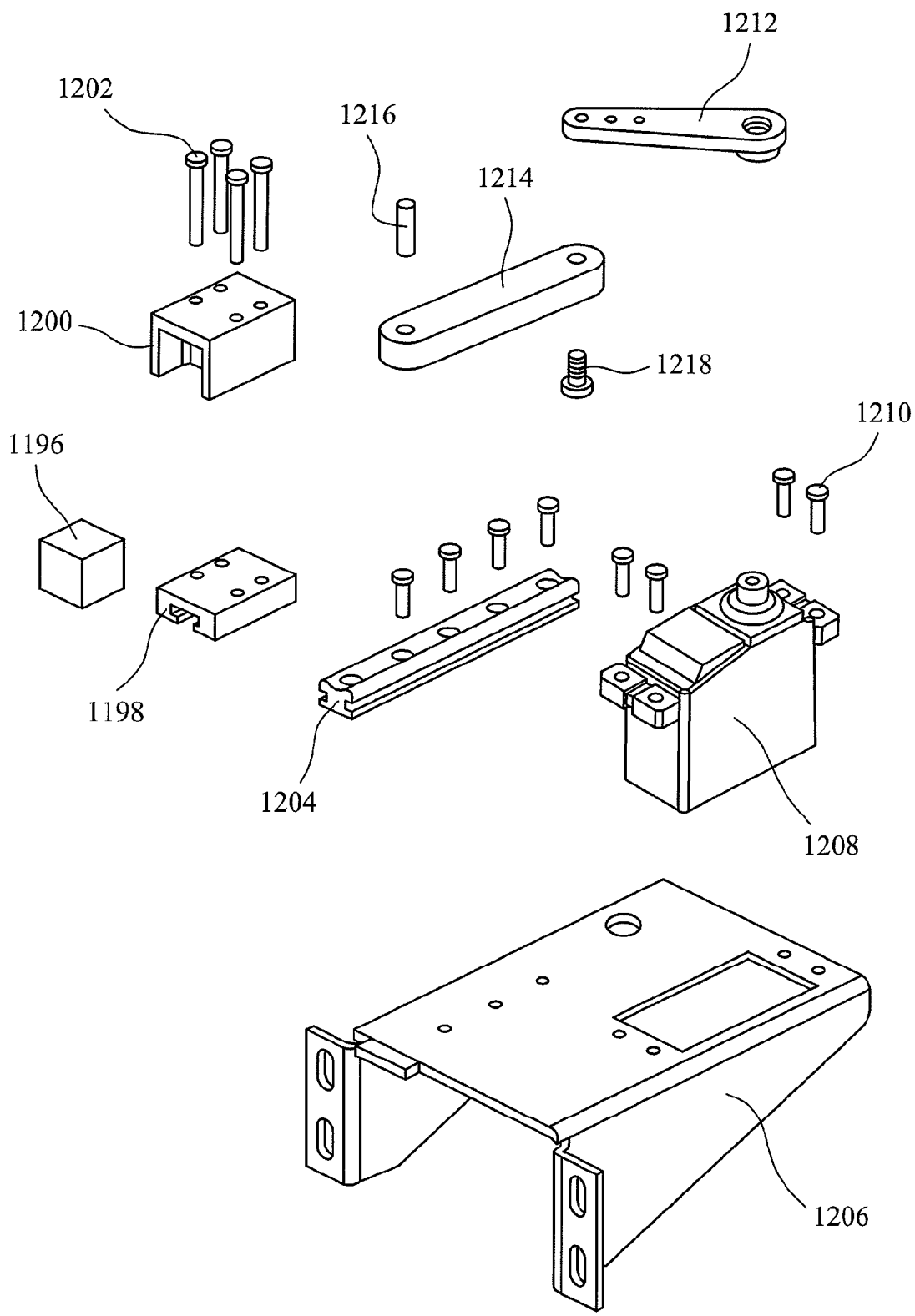

FIG. 31A depicts a perspective view of an example magnet stage used in one embodiment of the invention, FIG. 31B is an exploded view.

A rare earth magnet 1196 has the shape of a cube with sides of approximately 13 mm (0.5 inch). This is clamped to a carriage 1198 by clamp 1200 and screws 1202. The carriage 1198 comprises a longitudinal recess on its lower side which engages a track 1204 to limit movement of the carriage 1198 (and hence magnet 1196) to a single direction. The track 1204 is provided on a mounting bracket 1206.

To move the rare earth magnet, a high torque servo 1208 is affixed to the mounting bracket by screws 1210. The high torque actuator provides rotational movement to a servo arm 1212. The rotational motion of the servo arm is converted to linear motion of the magnet 1196 by constraining action of the track 1204 through link member 1214 and pin connectors 1216 and 1218.

In use, high torque servo 1208 is controlled to alter the position of the magnet in the z direction (along the line of the track 1204). Adjustment in the x and y directions perpendicular to the direction of the track is achieved during initial manufacture and assembly by mechanical adjustment.

Electronics System Overview

Figure 19:
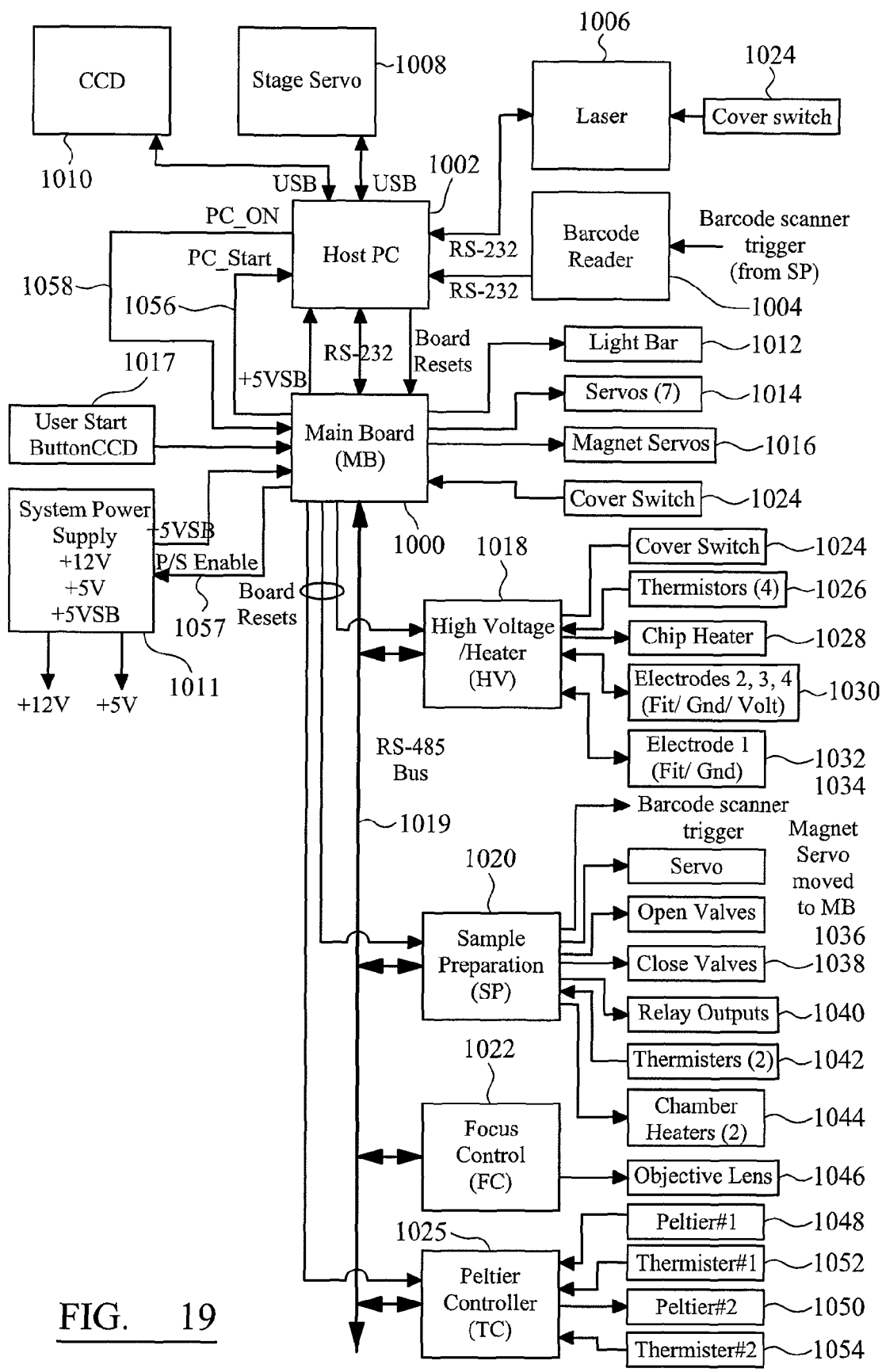
FIG. 19 is a diagrammatic representation of a system diagram depicting the electrical and electronic components used in the present invention.

FIG. 19 depicts a diagrammatic representation of the various electrical and electronic subsystems used in the present invention and the connections between them. A main board 1000 acts as a communication hub between Host PC 1002 and some of the various subsystems described below. Host PC 1002 assumes overall control of the operation of the apparatus to carry out analysis of a sample in a sample cartridge as discussed above. It interfaces with the Main Board 1000, a Barcode reader 1004 and a laser 1006 via respective RS-232 serial interfaces and with a stage servo 1008 and a CCD 1010 via respective USB serial interfaces. Alternative data interfaces may also be used. The barcode reader 1004 may be replaced or supplemented by an RFID reader (not shown).

Main Board (MB) 1000 is connected directly to a light bar 1012, servos 1014 for loading a sample cartridge, a magnet servo 1016 for controlling the position of a magnet and a user start button 1017. An RS-485 bus 1019 relays commands and data between the main board 1000 and a High Voltage power supply and heater control (HV) board 1018, a sample preparation (SP) board 1020, a focus control (FC) board 1022 and a peltier controller (TC) 1025.

A cover switch 1024 provides direct input for both the main board 1000, high voltage power supply and heater control board 1018 and Laser 1006 to detect when the cover of the apparatus is open and operate safety interlocks. Alternatively, separate cover switches may be provided.

The high voltage power supply and heater control board 1018 provides the high voltages required for the CE stage of analysis as well as controlling the resistive heater used during the CE stage. To provide this function it is connected to four thermistors 1026 for monitoring of temperature of a CE heater 1028, to which it is also connected. For providing the required high voltages at various points at the CE chip, electrode outputs 1030 (depicted as one element in FIG. 19) provide three outputs, each of which can be independently set to floating, ground or a specified voltage. A fourth electrode output 1032 is also provided, which is always connected to ground.

The sample preparation board 1020 controls all aspects of the sample preparation stage of the analysis of a sample, as discussed above. For this purpose it contains a signal line 1034 for triggering reading of a Barcode (or RFID or other identifier in alternative embodiments) by the barcode reader 1004. It includes a plurality of open valve 1036 and close valve 1038 heaters for opening and closing valves to move the sample between various stages of the sample preparation in the sample cartridge. A relay output 1040 is also provided. To control temperature during PCR, thermistor input 1042 monitors temperature and Chamber heater 1044 is controlled to achieve a desired temperature.

Focus control board 1022 controls focussing of the Laser 1006 used in the CE stage of analysis. It is connected to an objective lens 1046 of the optical system to adjust focussing.

Peltier control board 1025 controls the operation of peltiers 1048, 1050 based on temperatures measured by thermistors 1052, 1054.

In this overview discussion, although thermistors have been referred to, any suitable temperature sensor may be used alternative embodiments. Likewise the host PC may be any suitable computer system with any suitable operating system. Although the various components are separated into subsystems, there subsystems may integrated into fewer subsystems or split into greater subsystems in alternative embodiments.

The operation of each of these components, and novel aspects of their construction will now be described.

Main Board

This section describes the operation and functional features of the Main Board (MB) 1000. The MB 1000 monitors the User Start button 1017. When a button press of the User Start button 1017 has been detected, the MB 1000 starts the system power supply 1011 via link 1057 and after a short delay, asserts the start button input to the host PC 1002 by applying a voltage to link 1056, then releasing it. After a predetermined delay, for example 5 seconds, the _PC_ON signal on line 1058 is checked. If the _PC_ON output 1058 from the host PC 1002 is not active, the MB 1000 asserts the PC Start signal on link 1056 again. When the _PC_ON signal 1058 is active, the MB 1000 releases the P/S ENABLE signal it generates on link 1057. This is because the Host PC is then asserting the P/S Enable signal (not shown), keeping the power supply 1011 turned on.

If another User Start Button 1017 press is detected by the MB 1000, this is relayed to the host PC 1012 so it may begin its shut-down. When the shut-down is complete, The Host PC 1002 releases the P/S Enable signal, allowing the system power supply 1011 to shut down. In this state, only the +5VSB supply is still powering the MB 1000 and parts of the Host PC 1002.

The Host PC 1002 asserts four board reset signals to reset the MB 1000, HV 1018, SP 1020, and TC 1025 boards, then releases them all, allowing the boards to start. (These signal lines are not shown in FIG. 19.

When the Cover switch 1024 is detected open, the left and right CE chip servos open, and Peltier clamp open together, then the pressure platen opens. These servos move to their open positions, previously stored to the MB 1000 in flash memory. When the cover closes, the MB 1000 closes the pressure Platen, then the Peltiers and CE Chip servos together. The close positions are also stored in the MB 1002 flash memory. No action by the Host PC 1002 is required, although it may query the state of the servos and command them to any position via the MB 1000. All these actions are carried out using the servos output 1014.

When the servos are commanded to move by the MB 1000, they receive control pulses for one second. This allows sufficient time for them to reach their target positions. After that time, control pulses are disabled, and the servo powers down, preventing damage to the servo. The servos can be physically pushed to a different position during this time.

The Magnet servo 1016 is now controlled by the MB 1000. As with the other servos, it has predetermined open and close positions, stored on the MB 1000 in flash memory. As with other servos, the host PC 1002 can query and command the magnet servo.

The lightbar 1012 is a three segment "bargraph" visible to a user on the front of the apparatus to indicate the progress through analysis. Each segment may be lit up in blue or white, steady or flashing. An "alternate" mode is also available where the segment toggles between blue and white. A single red segment is available to indicate the state of the laser, and may be on, off, or flashing. Each of these light bar states is commanded by the Host PC via the MB 1000.

The MB 1000 is also responsible for relaying commands and data between the Host PC 1002 and the other boards on the RS-485 bus 1019. Commands from the Host PC 1002 over RS-232 to any of the boards connected to the RS-485 Bus 1019 are prefixed with the boards two letter code ("MB", "SP", "HV", "TC", or "FC"). When the MB 1000 receives a command/query for a board on the bus, the original prefix (two letters and a space) is replaced by a single byte board address, and the packet is transmitted over the RS-485 bus 1019. Commands directed to the MB 1000 are processed locally rather than transmitted.

Responses returning over the RS-485 bus 1019 are received by the MB 1000, with the responding board's single byte address. The address byte is replaced with the appropriate prefix and a space, then relayed to the Host PC 1002 over the RS-232 connection.

In normal operation, only the MB 1000 may spontaneously transmit over the RS-485 bus 1019. All other transmissions are responses from the selected board.

The MB 1000 is designed so that new devices may be added to the system easily. Minor changes to the MB are required to add the new board address and prefix, and the new device is attached to the RS-485 bus 1019. The FC board 1022 is such an example.

Bus communications on the RS-485 bus 1019 may be monitored by attaching a second MB to the bus to log communications on another computer system for debugging purposes (not shown).

Sample Preparation Board

Figure 20:
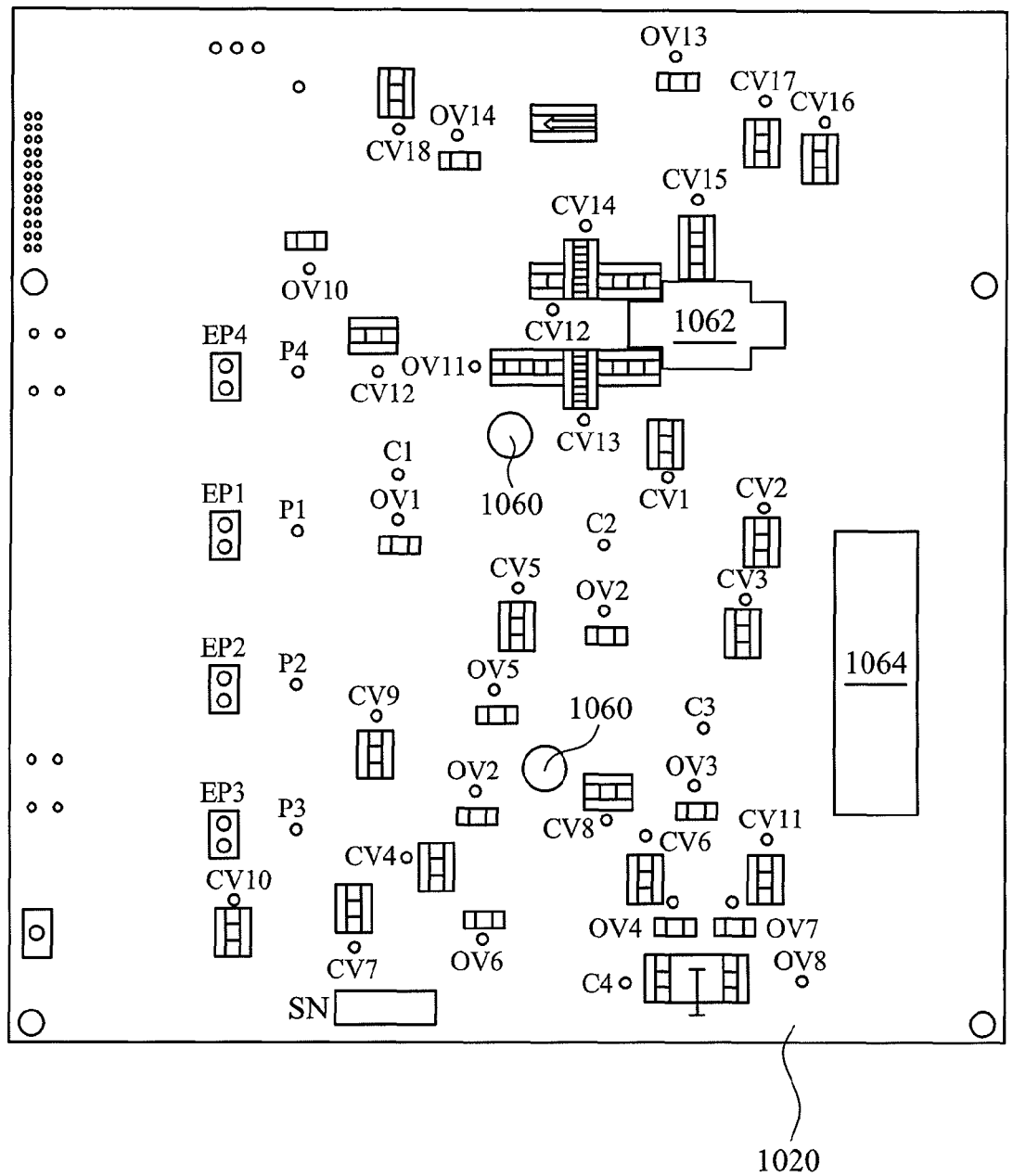
FIG. 20 is an illustration of the physical PCB layout for use in Sample Preparation stages.

FIG. 20 depicts the physical arrangement of the Sample Preparation (SP) Board 1020. This board controls the sample preparation and PCR stages of analysis. The physical design of the SP board 1020 is important because features on the board interface with features on the sample preparation cartridge. The features on the SP Board 1020 are aligned with the design of the sample cartridge. The SP board 1020 delimits two round openings 1060 which engage projections formed on the sample cartridge to align the cartridge accurately with the PCB to ensure proper interface of valves and pumps provided in the sample cartridge with the SP board 1020. The SP Board 1020 also delimits a generally cross-shaped opening 1062. Opening 1062 corresponds to the PCR chamber on the sample cartridge and is provided to allow the Peltier assemblies to contact chamber. A rectangular opening 1064 is also delimited by the SP board 1020. This is to allow for a barcodes on the sample cartridges to be read by the barcode reader 1004.

As shown in overview on FIG. 19, the SP board 1020 includes Open Valves outputs 1036. The physical arrangement of these open valve outputs are indicated on FIG. 20 with the prefix OV (OV1-OV14). The SP board 1020 also includes Close Valves outputs shown in FIG. 19 in overview as 1038. The physical arrangement of these close valves outputs are indicated in FIG. 20 with the prefix CV (CV1-CV18). The Open and Close Valves outputs on the SP Board operate temperature controlled valves, which are provided on the sample cartridge. As depicted in FIG. 20, Open and Close Valve outputs OV1-OV14, CV1-CV18 are implemented by standard, commercially available 2512 surface mount resistors. These are rated up to 155° C. 2152 surface mount resistors are preferred because they present a flat surface to give good contact with the cartridge. They also provide very repeatable temperature results.

The open and close valves outputs OV1-OV14, CV1-CV14 have a configuration chosen dependent on the corresponding valve in the sample cartridge. For example, as can be seen in FIG. 20, opening valves OV1-OV14 generally require a smaller heated area than the closing valves CV1-CV14 so the open valve outputs OV1-OV14 occupy a smaller area on the SP board 1020 than the close valve outputs CV1-CV18. For example, Open Valves outputs comprise one resistor. Typical Close Valves outputs comprise three resistors.

In use, a predetermined voltage/current may be supplied for a predetermined time which is known to heat the surface mounted resistors to a required temperature for the wax in the valve to melt and operate the valve, for example to 120° C. The temperature is determined by test which will provide a suitable resistor value using a suitable heater voltage to provide a set temperature response in the resistor elements. Optionally, a temperature switch may also be used behind each resistor heater. Temperature switches are commercially available and have temperature sensing built in. A temperature switch may be set for any suitable temperature, for example 120° C., and, when activated, will control the resistor heaters to 120° C.

Additional outputs from the SP board 1020 include electrodes for supplying electrical power to Electrochemical Pumps, shown with prefix EP in FIG. 20 (EP1-EP4). Electrochemical pumps are controlled by a microcontroller within the SP board 1020. The microcontroller turns on transistors, preferably FETs, on the SP board to apply the necessary voltage to activate the pumps on the cartridge. The electrodes EP1-EP4 are preferably pogo pins to provide a good electrical connection.

Two temperature-controlled chamber heater outputs 1044 are provided (C4 and denature in FIG. 20). These are implemented with surface mount resistors as with the open valves outputs OV1-OV14 and close valve outputs CV1-CV18. However, because these heat sample chambers in the sample cartridge, more accurate temperature control is required.

Figure 21:
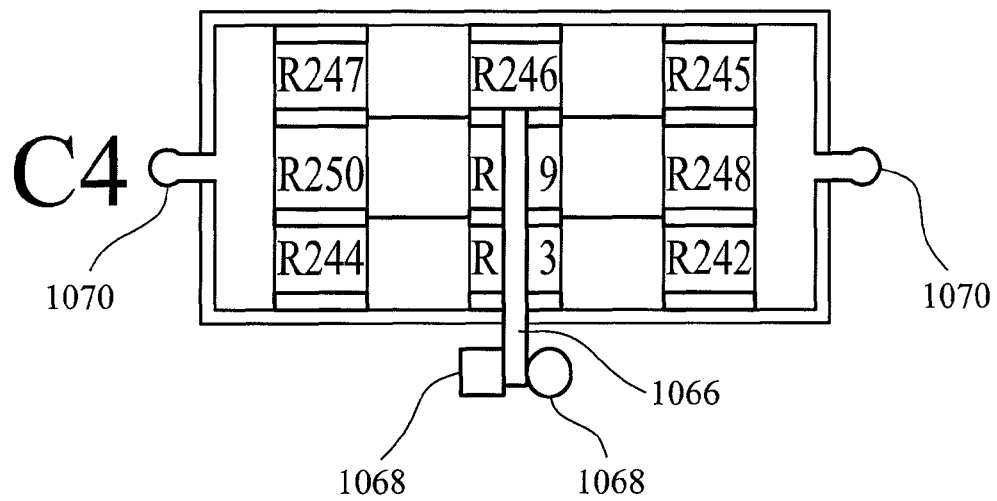
FIG. 21 is an illustration of the physical layout of an example resistive heater using surface mount resistors for use with the present invention.

FIG. 21 is an enlarged diagrammatic representation of the construction of Heater C4 in FIG. 20. Heater C4 comprises an array of nine surface mount resistors R242-R250. A groove 1066 is formed the material of the printed circuit board in the same location as the Heater C4. Groove 1066 is preferably about 1 mm deep and about 10 mm long. A thermistor is laid in the groove 1066 and soldered to the two pads 1068 at the bottom. The thermistor provides the feedback necessary for control. The nine resistors R242-R250 are soldered into their locations with silver solder, they are electrically isolated from the thermistor in the groove 1066. Silver solder is preferred because it has a higher melting point than other solders. The resistors are preferably soldered as close together as possible to reduce any gaps between them, which will not be heated. Terminals 1070 on the right and left side provide voltage and ground paths to supply power to the resistors and control the temperature of the heater.

Figure 22:
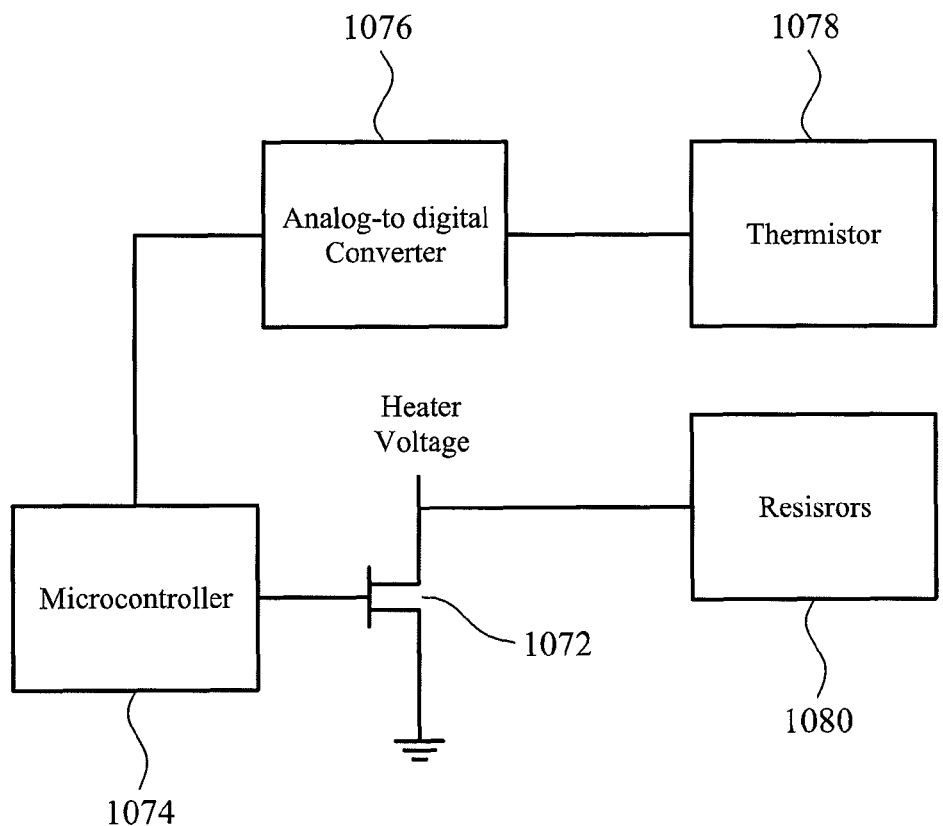
FIG. 22 is a block diagram depicting the control circuit for the heater of FIG. 21.

FIG. 22 depicts a high level block diagram of a controller for the heater C4 of FIG. 21. This arrangement can be used in any situation where feedback control of temperature is required. The chamber temperature is controlled by applying a pulse-width modulated signal to the between the terminals 1070 by transistor 1072. The transistor 1072 is driven by a controller 1074 which has an input from an ADC 1076 reading the value of the thermistor 1078.

In use, the temperature from the thermistor (which is a measurement of the temperature of the resistors 1080) is fed back to the controller 1074 which compares this value with the desired temperature. The microcontroller uses PID control to control the temperature. To increase temperature, the pulses of the PWM are widened and the duty cycle increase. To decrease temperature, the pulses are narrowed and the duty cycle decreased.

Peltier Controller Board

The Peltier Controller (TC) Board 1025 is essentially a self-contained controller for the Peltier assemblies. It manages both assemblies at once. Commercially available controllers control only one Peltier, and are approximately the same size (for one Peltier control) as this board. The TC Board 1025 is powered by a 12V input from the system power supply 1011, but the required power supply to drive the Peltiers (which require 2.3V at 8 A each) is provided separately on the TC board 1025 itself Given losses in control circuitry and the high current requirements, this power supply provides a 3.2V output with an available 30 Amps.

Peltiers are used because they can act as both a heater and a cooler, dependent upon the polarity of their input. As such the TC Board 1025 needs the ability to switch polarity of the voltage outputs to the peltiers. This is accomplished using respective H-Bridge circuits, as are known in the art. These devices, under the control of a controller provided on the TC Board 1025 can switch the high and low outputs as required.

With the exception of the H-Bridge circuitry, the temperature at each Peltier is controlled in the same basic way as described above with reference to FIG. 22. Four high-power transistors (preferably FETs) are used per channel (two for each direction) to supply the pulsed PWM power output to the Peltiers. A thermistor embedded in a copper heat spreader on top of each Peltier is connected for feedback to close the control loop.

High Voltage Power Supply and Heater Control Board

The High Voltage Power Supply and Heater Control (HV) board 1018 attaches to the RS-485 bus 1019 for communications, and accepts a reset signal directly from the Host PC 1002.

The HV board 1018 supports four thermistors 1026 for monitoring the temperature of the CE Chip heater 1028. Other embodiments may support fewer or more thermistors. The CE Chip heater 1028 is controlled by modulating power input using Pulse Width Modulation (PWM). The HV board 1018 also includes outputs 1030 for generating voltages of up to 5 kV on three terminals (4 kV in some embodiments), or grounding any/all of the three terminals, or allowing any/all of the three terminals to float (be disconnected from all electrical circuits). For operator safety, a cover switch 1024 provides an interlock which disables all high voltage sources and floats all output terminals 1030 when the cover is opened.

Four thermistors 1024 are used to monitor CE chip temperature at various points along the heater surface. To simplify control, only one thermistor is actually used as an input to the temperature control functions (discussed in more detail below). All four thermistor inputs 1024 are measured and logged. The current temperatures may be requested by the Host PC 1002 at any time.

Measurement of temperature requires 80 ms to complete the conversion before the result can be read out. Temperature measurement is described in more detail below. Accurate control can be achieved by measuring the temperature preferably about once a second, although the temperature can be measured more frequently if required.

As mentioned above, the current temperature of one thermistor 1024 is used to as an input to the temperature controller. The temperature controller (not shown) is provided on the HV board 1018. It determines the duty cycle (% ON time) to be used in a PWM signal. Preferably, the temperature controller determines the duty cycle once a second and it remains constant until it is next updated, this is described in more detail below.

Electrode 1032 is either grounded by a relay, or allowed to float (high voltage relay is open). Electrodes 1030 may also be grounded or be allowed to float, but they can also output voltages up to 5 kV with a current of up to 104 A, preferably up to 4 kV at currents of 50 μA.

The HV board 1018 includes a 3V 16 A power supply to provide the necessary voltage and power for its operation. Three high voltage power supply boards are installed on the board to provide the voltages required at electrodes 1030 for use during the CE stage of analysis. These power supplies can each provide up to 4000V at 50 μA to electrodes 1030. The HV board manages these three power supplies including voltage and current monitoring. It also controls the temperature of the CE Chip Heater 1028.

Onboard RAM is provided on the HV board 1018 to store on demand the voltage and current values of the three electrodes 1030 as well as up to four temperature measurements from the CE Chip Heater via thermistors 1026.

The three HV power supplies use commercially available power converters from EMCO (preferably EMCO Q Series (Q40-5), although other power converters can also be used) that take a 0-5V input and convert it to 0 to 4000V. The control, output, and feedback circuitry, under firmware control, produce a linear output to drive the CE process. Voltage and current monitoring circuitry are provided on the HV board 1018. The firmware is calibrated for each of the individual HVPS modules to provide the highest possible output and feedback properties.

The construction of the HV power supplies and their connection to the CE Chip is depicted in diagrammatic form in FIG. 32. FIG. 32 depicts three HV power supplies 1220a, 1220b, 1220c. (The construction of the first HV power supply 1220a is shown in more detail in FIG. 32 than the second and third HV power supplies 1220b, 1220c. The construction of the second and third HV power supplies 1220b, 1220c is the same as the first HV power supply 1220a.) The output of the three HV power supplies, 1220a, 1220b, 1220c is connected to the CE chip 1222. Within the CE chip each HV power supply 1220a, 1220b, 1220c is tied together and connected to a common ground 1224. The rating of each of the HV power supplies is preferably the same, for example 4000V or 3000V, to ensure that there is no danger of damage to a lower rated HV power supply.

Each HV power supply has a respective control input $V_{controla}$, $V_{controlb}$, $V_{controlc}$, which is generated by a respective 12-bit DAC 1226a, 1226b, 1226c. All the 12-bit DACs 1226a, 1226b, 1226c are fed the same precision voltage reference 1228 through buffer 1230 for consistency. The precision voltage reference 1228 generates a 4.096V reference, although other values may also be used.

As depicted for the first HV power supply 1220a, each power supply includes a High Voltage source 1232. This source is controlled by the desired voltage $V_{controla}$ and feedback of the voltage output via the voltage divider formed by resistors 1106 and 1108.

Resistors 1106 and 1108 form a voltage divider to measure the voltage. Resistor 1234 enables measurement of the current. The operation of these to measure the current and voltage is described below with reference to FIG. 25. These enable low voltage parts to be used in a high voltage environment, protected by the voltage divider formed by resistors 1106, 1108 and current sense resistor 1234.

The construction of the HV power supply 1220a, 1220b, 1220c as depicted in FIG. 32 enables them to be more compact then the prior art, for example 50×27×18 mm. Reverse protection diodes are also not required, unlike the prior art.

CE Heater Physical Construction

Unlike the other heater components, which are formed from surface mount resistors, the CE heater 1028 is manufactured from a multilayer PCB, with a trace on the PCB providing the heating. CE heater must provide as uniform a temperature as possible over a relatively large area, it has been found that this can be provided by a heater formed from a PCB. The physical layout of the heating layer of the PCB is depicted in FIG. 23.

Figure 23:
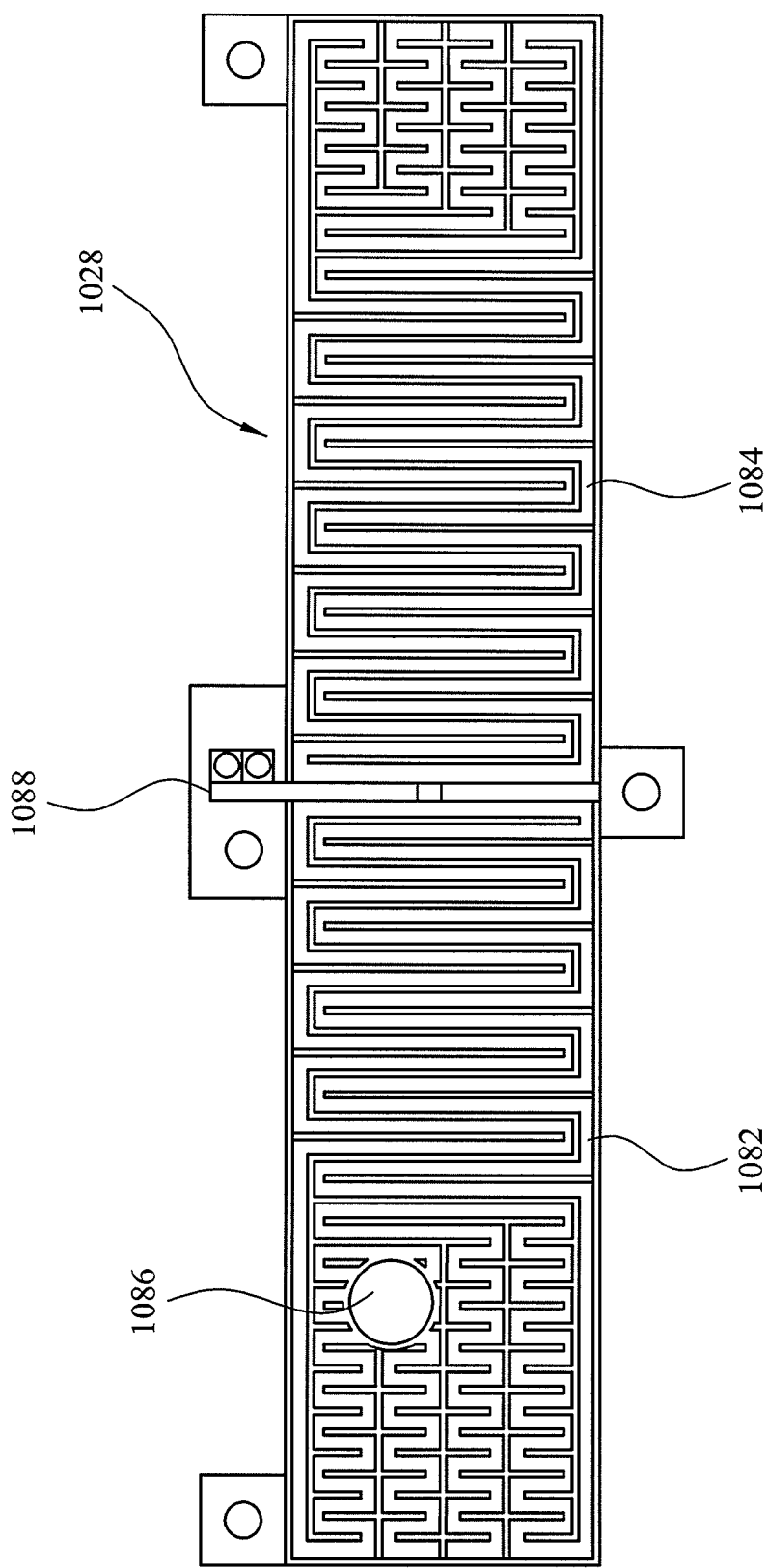
FIG. 23 is an illustration of one layer of a PCB depicting a trace for use as heater.

The inner layer of PCB is depicted in FIG. 23. It contains traces 1082, 1084 configured to provide uniform heating from end to end. This is achieved by undulating the traces over the surface area. As can be seen in FIG. 23 in a central portion of the PCB the traces are configured with an undulating path such that peaks and troughs of the undulations are nested within one another. In outer portions of the PCB the traces are configured in undulations where peaks and trough of adjacent undulations are opposed to each other, so that a peak is adjacent a trough and vice versa. This configuration has been determined to give near uniform heating. Other configurations are possible in alternative embodiments.

Above the inner layer depicted in FIG. 23, a solid copper layer is formed to act as a heat spreader. The top layer of the PCB is empty of conductive elements, providing protection for users.

The CE heater 1028 delimits an opening 1086. Opening 1086 is the detection area, allowing the laser 1006 to illuminate the chip capillary and the result to be detected by the CCD 1010.

At the middle of the board, a groove 1088 is cut into the top layer. A thermistor is placed in this groove and connected to the temperature controller for feedback. The control circuit may be the same as that discussed with reference to FIG. 22 above, or as will be discussed below in more detail.

Overview of Control Methodology and Operation

During analysis, the instrument controls the various protocols to process and analyse the sample in the sample cartridge and produce the required result. Valving, pumping, temperature cycling, laser, CCD, and capillary electrophoresis are all controlled by the instrument.

The system is run by the Host PC 1002 that interfaces directly with the Main Board 1000 via serial communication. The Main board 1000 then distributes the commands and responses to the rest of the system circuit boards and feeds them back to the Host PC 1002 for control and analysis. The Host PC 1002 also controls the laser 1006 to turn it on and off and monitor its conditions as required, and the CCD 1010 to gather data as required.

In the sample preparation process, it is necessary to suspend magnetic beads in a solution and to keep them from being washed away during various cycles. This is achieved using a rare-earth magnet. The magnet is controlled by a magnet servo 1016 under direct control of the firmware at the command of the Host PC 1002. The magnet location can be controlled to produce the necessary strong magnetic field to hold the beads when necessary and then removed automatically to release the beads at the proper time.

Although mechanical features generally align the CE chip with the laser and optical system, the small diameter of the laser beam means some adjustment to align and focus the laser on CE chip capillary is preferable. An automated process is provided that locates the CE chip capillary over the CCD detector 1010 and focuses the optics. The CE chip sits on a stage that is controlled in the Y direction with a fine servo linked to the computer. The optic stack includes a piezo-controlled mechanism that will adjust the focus of the optics. Using the output of the CCD, these two adjustments are tuned for a peak output on the CCD for lane finding and focus without user intervention.

Another automatic function is the control of the various moving mechanisms built into the system. There are two arms with electrode contacts to apply high voltage to the CE chip as required (powered from electrodes 1032 from the HV board 1018). To insert the chip into the system, these arms need to be out of the way. Additionally, the cartridge needs clearance when the arrangement is installed in the system, but must be pressed against the Sample Preparation Board when it runs to get the proper heat transfer for valve control and good electrode contact for pump control. The PCR chamber also needs to have the Peltiers tightly clamped on both sides to provide a good thermal interface. All of these movements are controlled by the instrument automatically. When the cartridge (including the CE chip) is inserted into the unit and the door is closed, servos are controlled to close in the proper sequence to position the arms onto the chip, press the cartridge against the Sample Preparation Board, and close the Peltiers onto the PCR chamber.

Software running on the Host PC 1002 controls user access. It can be run in "expect" and "standard" modes depending on the skill level of the user. "Expert" users may access individual components for maintenance and troubleshooting if needed. A "Standard" user has access to the standard processes which can be run individually or with a "one-button" approach to automatically run the entire analysis sequence.

In automatic running of the entire analysis sequence, the system will run from start to finish. The user is informed of progress by a display on the monitor of the Host PC 1002 and via LED indicators (such as Light bar 1012) to show progress or alert the user if attention is needed. All required data is stored automatically for later evaluation and associated with the identification number of the sample cartridge, read by the barcode reader 1004 or other means such as RFID.

The host PC 1002 gathers a host of data during each analysis run. All aspects of the process are monitored and files are created to store the parameters of the run. Data stored includes the user and time as well as the identification of the sample in test, readings from the PCR process that show the entire sequence beginning to end, the voltage and temperature settings for each step in the CE process, readings from the voltage, current, and four temperature sensors taken over the entire test, and all the raw data taken from the CE process with the CCD. This data is stored and available for review at the user's request. Data review can show charts of the entire PCR thermal cycling, the voltage, current, and temperature conditions at every second of the CE phase, and all the images captured by the CCD correlated to time.

Voltage Control for CE Process

The HV Board 1018 controls the output of the three HV power supplies via electrodes 1030 so that they all reach the desired value at substantially the same time. This method will now be described with reference to the flow chart of FIG. 24; the same method is used for each electrode. The voltage is altered over a predetermined time; the use of the same predetermined time for each electrode means that they all reach the new value at substantially the same time.

Figure 24:
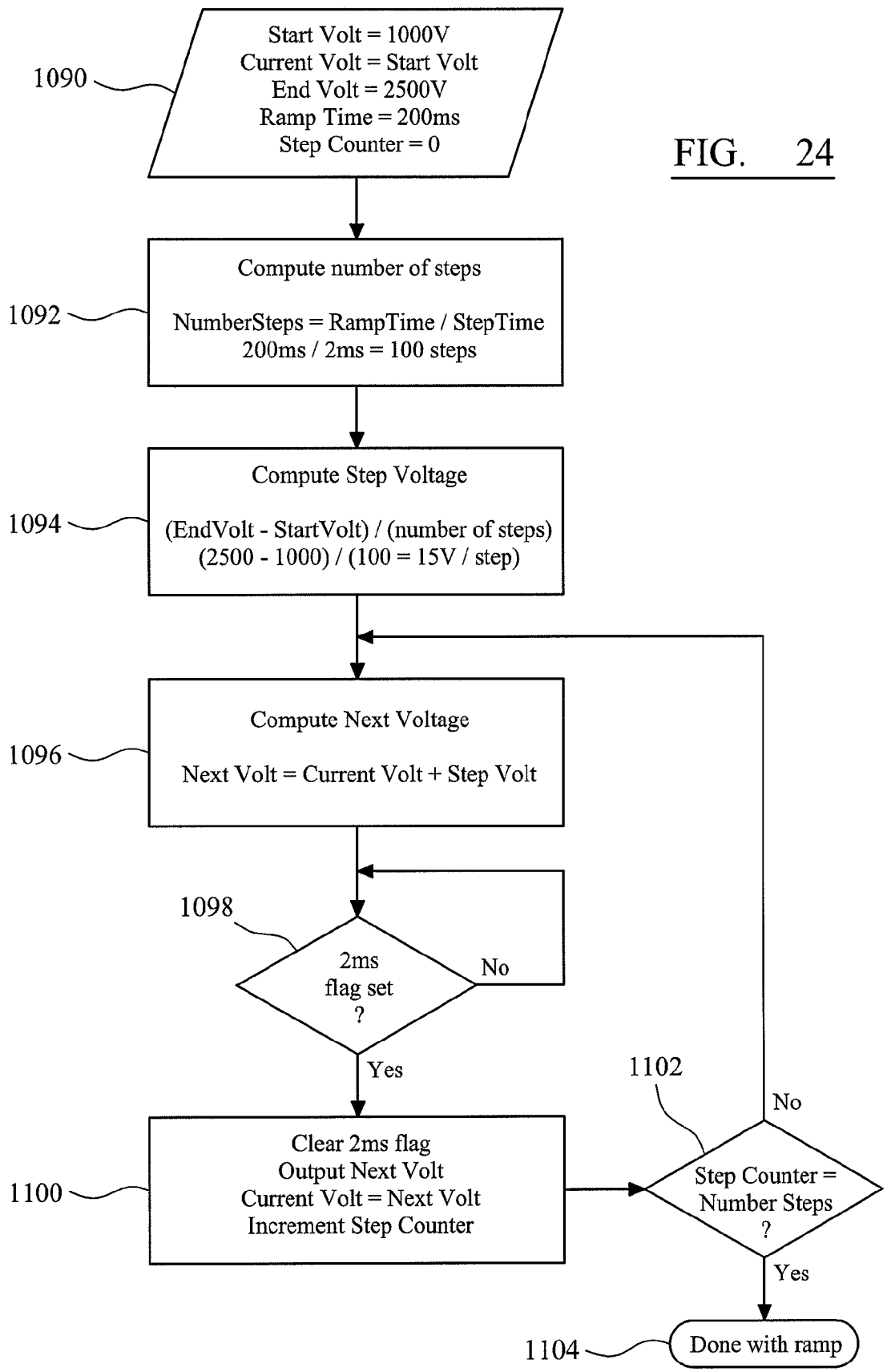
FIG. 24 is flow chart of the control method for output voltage used in the present invention.

The method begins at 1090, where the parameters for a change in voltage output on one of the electrodes are set. As illustrated in FIG. 24, a change from a start value of 1000V to an end value of 2500V is required over a ramp time 200 ms. A current voltage value is initialised to the start value and a step count is initialized to zero.

Execution proceeds to 1092 where the number of steps to reach the end value are calculate by dividing the ramp time by the step time. The step time is preferably 2 ms, giving 100 steps for the transition. The number of steps taken depends on the user configured ramp time set in 1090, and may range from 20 ms to 5000 ms, defaulting to 200 ms.

Next, in 1094, the Step Voltage is determined by the difference between the starting and ending voltage, and the number of steps calculated in 1092. In this example, the Step Voltage is 15V. The Step Voltage for each channel is converted to binary data for supply to a DAC in the HV power supply. The DAC in turn outputs an analog voltage for controlling the high voltage converter. The conversion is simply applying $y = mx + b$ where m is the conversion gain and b is the conversion offset. Both m and b are determined when the board is calibrated at the point of manufacture.

For each step, the Next Voltage is calculated by adding the Step Voltage to the Current Voltage in 1096.

Execution then pauses at 1098 to wait for a 2 ms flag to become set. When it becomes set, execution continues to 1100 and the 2 ms flag is then cleared. The Next Voltage is output to the hardware, the current Voltage is set to the Next Voltage and the step counter is increments.

At 1102, a check is made whether a step counter is equal to the number of steps required from 1092, if it is execution terminates at 1104. If it is not, execution returns to 1096, a new Step voltage is then computed, and the loop repeats. When all the ramp steps have been completed, the output will be at the commanded voltage and the ramp is complete.

This method allows an arbitrary number of HV power supplies to be controlled so that all reach a desired voltage at the substantially the same time.

Voltage and Current Measurement for CE Process

The HV board 1018 is also capable of measuring the voltage and current at each of the high voltage electrodes 1030 (electrode 1032 is not monitored). This can verify that they at the required voltages for the CE process.

Figure 25:
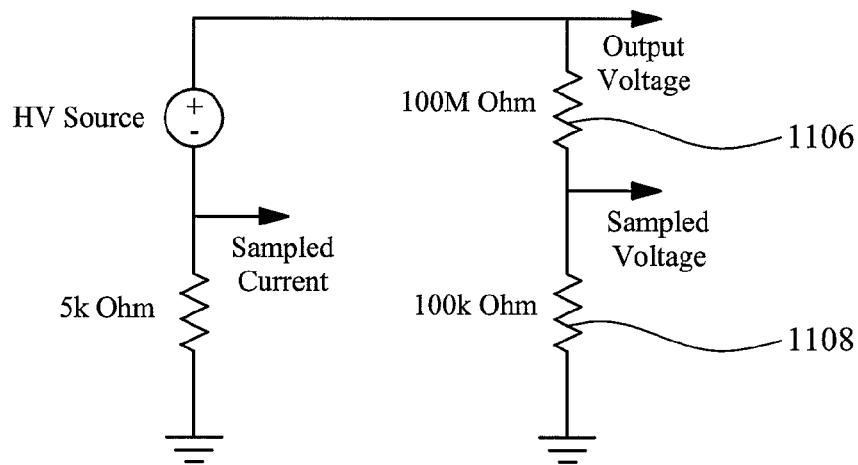
FIG. 25 is a schematic diagram depicting current and voltage measurement points in a high voltage power supply according to the present invention.

The circuit in FIG. 25 is used to sample the voltage and current in each channel. The voltage and current samples are filtered, and some offset and gain are applied before the signals are presented to an ADC for conversion. The buffering provided by the resistors in FIG. 25 is required to reduce the high source impedance of the signals to a low impedance required for the ADC, and to keep the signals within the ADC's conversion range.

Measuring current also requires knowledge of the load voltage, so voltage and current measurements are always performed together. It is preferred, voltage and current measurements for all three channels are performed at the same time.

The voltage is measured by a resistive divider from the output to ground formed by resistors 1106 and 1106. The sampled voltage is filtered and then applied to the ADC for conversion.

As with setting the output voltage, measuring the output voltage is converted from ADC results to a voltage using a formula y=mx+b. The gain (m) and offset (b) are determined during board calibration by comparing the output voltage as measured by an external meter to what the board reports. For example, this data may be gathered at various voltages and plotted. A linear trend line with its equation is determined from the plot. The gain and offset from the equation of the trend line are used as the calibration constants m and b.

Determining the load current is somewhat more difficult, as the current to be measured is a significant portion of the HV source maximum current and can be exceeded in magnitude by the current flowing in the resistive voltage divider.

The HV power supply is preferably capable of outputting up to 100 μA at 5000V. At 5000V, the resistive voltage divider with values of 100 MOhm and 100 kOhm draws 50 μA just to measure voltage. Fortunately, in normal operation the current to be measured is generally less than 20 μA.

Measuring the channel current is performed by measuring the total current in the HV Source return leg, then subtracting the current flowing in the voltage divider. The current that remains is the load current.

Being able to measure the load current also requires knowledge of the load voltage, so a voltage measurement always precedes a current measurement.

After performing a voltage measurement, the total channel current is measured. An offset is subtracted from the conversion result to remove the offset introduced in the circuit. The measured voltage is multiplied by a constant M1 and subtracted from the conversion result. This removes the voltage divider current. The remaining measurement is multiplied by M2, and is reported as the load current.

Temperature Measurement

As discussed above, temperature measurement is required for the control of heaters in several stages of sample analysis and processing. In various configurations described above, a thermistor is used to measure temperature.

Although the resistance of the thermistor can be measured using conventional techniques to give an indication of temperature, it is desirable to access more accurate temperature measurement.

The construction of an example temperature measurement circuit is depicted in 26. This construction can be applied to one or more of the temperature measure on the CE chip heater 1028 (up to four separate measurements in different positions), the Peltier controller (up to two separate measurements via thermistor inputs 1052 and 1054) and the SP Board (up to two separate measurements via thermistors input 1042 for heaters controlled using feedback control).

Figure 26:
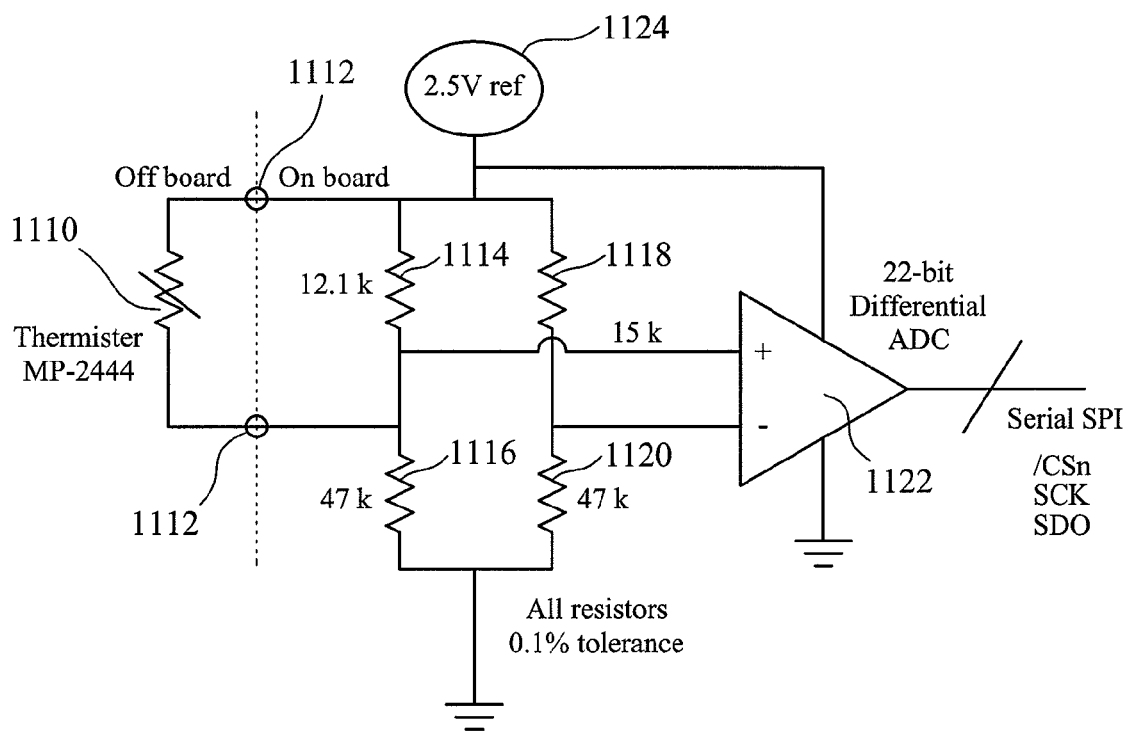
FIG. 26 is a schematic diagram depicting a temperature measurement circuit used in the present invention.

As shown in FIG. 26, an MP-2444 thermistor 1110 is used as a temperature sensor. The MP-2444 is preferred for its small size, and consistency between parts. It has been found that an MP-2444 thermistor can be replaced by another without significant effect on the measurement results. Alternative thermistors may also be used.

The thermistor 1110 is connected across terminals 1112 provided on the PCB (indicated in FIG. 19 as 1026, 1042, 1052 and 1054). The remaining parts of the circuit are provided on the PCB. Terminals 1112 connect the thermistor in parallel with a first resistor 1114 in one arm of a bridge circuit. A second resistor 1116, third resistor 1118 and fourth resistor 1120 form the remaining components of the bridge. The first and second resistors 1114, 1116 are connected in series to form a first arm of the bridge and the third and fourth resistors 1118, 1120 are connected in series to form a second arm of the bridge, connected in parallel with the first arm of the bridge. The first resistor 1114 has a value 12.1 KOhm, second and fourth resistors have values of 47 kOhm and the third resistor has a value of 15 kOhm. The use of 0.1% tolerance resistors is preferred so that there is no need to calibrate each individual bridge due to resistor manufacturing variation.

A differential ADC 1122 is connected across the bridge. The ADC is a 22-bit delta-sigma differential converter, for example the commercially available Microchip part MCP3551 Single-Channel 22-bit delta-sigma converter. A delta sigma converter is preferred because it has a high immunity to electrical noise. The differential input is required because the measurement is across a bridge.

A voltage source 1124 provides power to the bridge and also serves as the ADC conversion reference for ratiometric measurements. Preferably, a precision 2.5V reference is used, for example the commercially available Microchip part MCP1525 2.5V voltage reference, but any low noise voltage reference could be used in alternatives.

The choice of 2.5V voltage source 1124 and components in the bridge were selected to keep the power dissipation within the thermistor to a low enough level so as to not affect temperature measurement results. Preferably, the power dissipation in the thermistor is less than 7 μW.

Firmware

In use, when a temperature measurement is required, a controller on the relevant PCB triggers the start of a conversion by pulsing a signal line (/CSn) low. A signal line is provided for each individual temperature sensor circuit. Approximately 80 ms later, the conversion is complete and the result is ready to be read out. The controller then lowers the signal line, and clocks out 32 bits of data from the ADC 1122. From this, the 14 most significant bits are extracted containing the required data.

Figure 27:
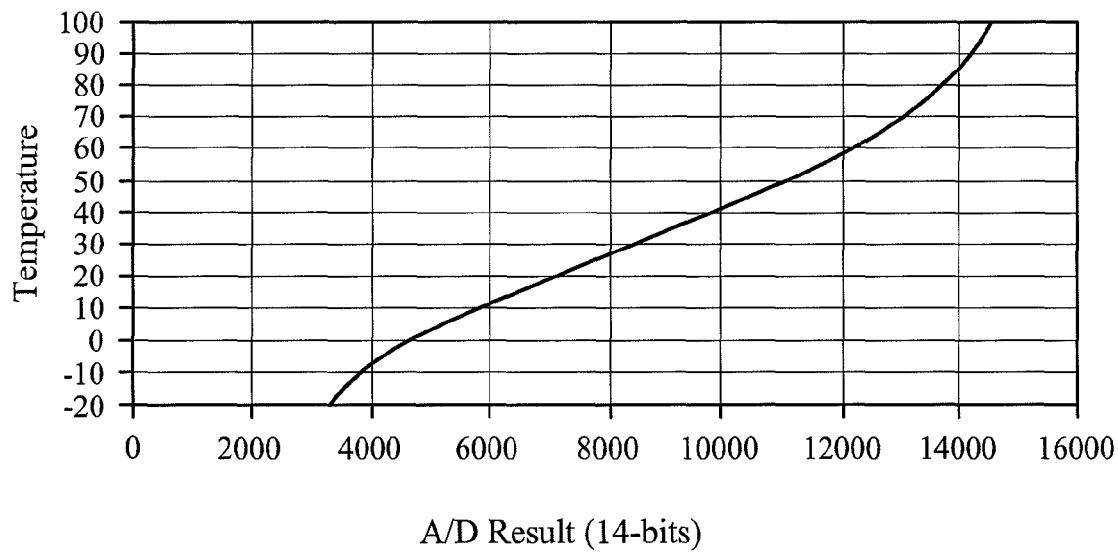
FIG. 27 is a graph depicting the output of the ADC in the circuit of FIG. 25 against the measured temperature.
Figure 28:
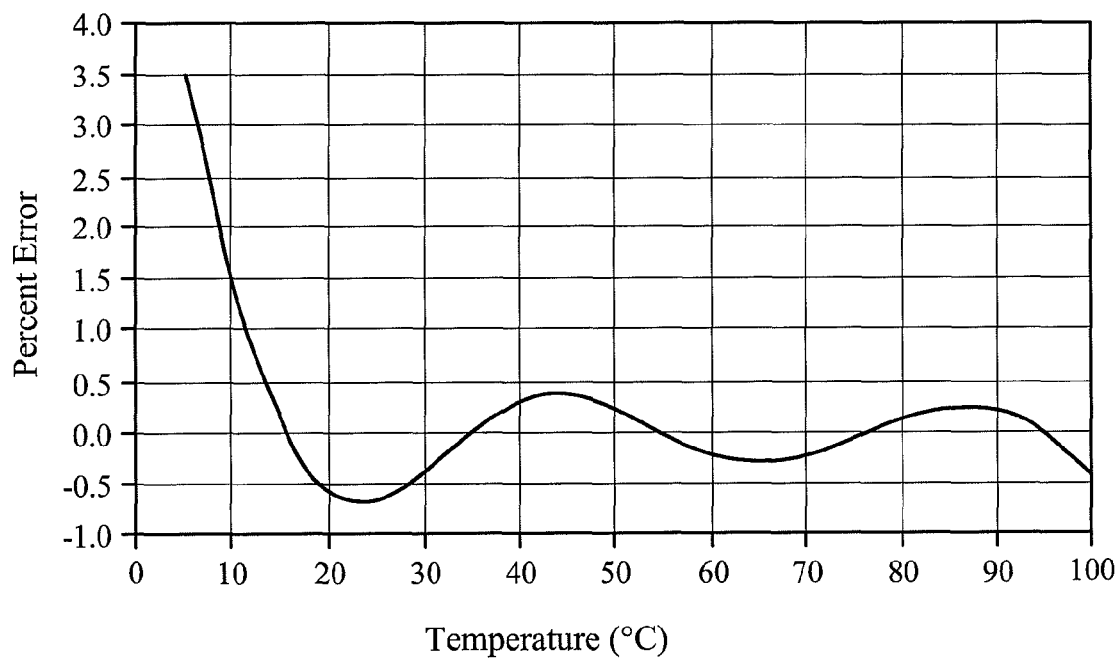
FIG. 28 is a graph depicting the error in the temperature measurement of FIG. 26.

The 14 bits of data are then processed by the controller to convert the raw number into a temperature. The conversion is determined from experimental data and a 6th order Polynomial has been found to be appropriate, although higher or lower order polynomials may also be used. For the components in FIG. 26, the polynomial has been determined to be:

$$y=7.0007732E-23x^6-1.0757374E-18x^5-3.5630874E-14x^4+1.1479772E-09x^3-1.2597522E-05x^2+6.9533980E-02x-1.4784255E+02$$

where x is the 14-bit data, and y is the temperature in degrees Celsius. The results of the conversion are shown in FIG. 27. This allows a temperature resolution of 0.02° C. (minimum) across the −20° C. to +100° C. range, and can return usable results beyond 110° C. For temperatures above 30° C., the measurement error is less than ±0.5% (Measurement error against temperature is depicted in FIG. 28).

Temperature Control Method

A feedback control method is used to control temperature of heaters at various stages in sample preparation and analysis. The temperature can be measured using a temperature sensor circuit described above. The actual temperature is measured once a second. This is fed back into the control loop and used to calculate an updated PWM (Pulse Width Modulation) value. This PWM value is then used until the next temperature measurement. As mentioned above, the actual temperature measurement requires approximately 80 ms. The control loop described below may then be executed in less than 1 ms. PWM controls the power applied to the heating element (which may be a Peltier or a resistive heater) in effectively a linear output by altering the duty cycle (the period for which the output is on to apply power to the heating element. A PWM switching frequency of around 2.4 kHz has been found to be preferable, although other switching frequencies may also be used.

Figure 29:
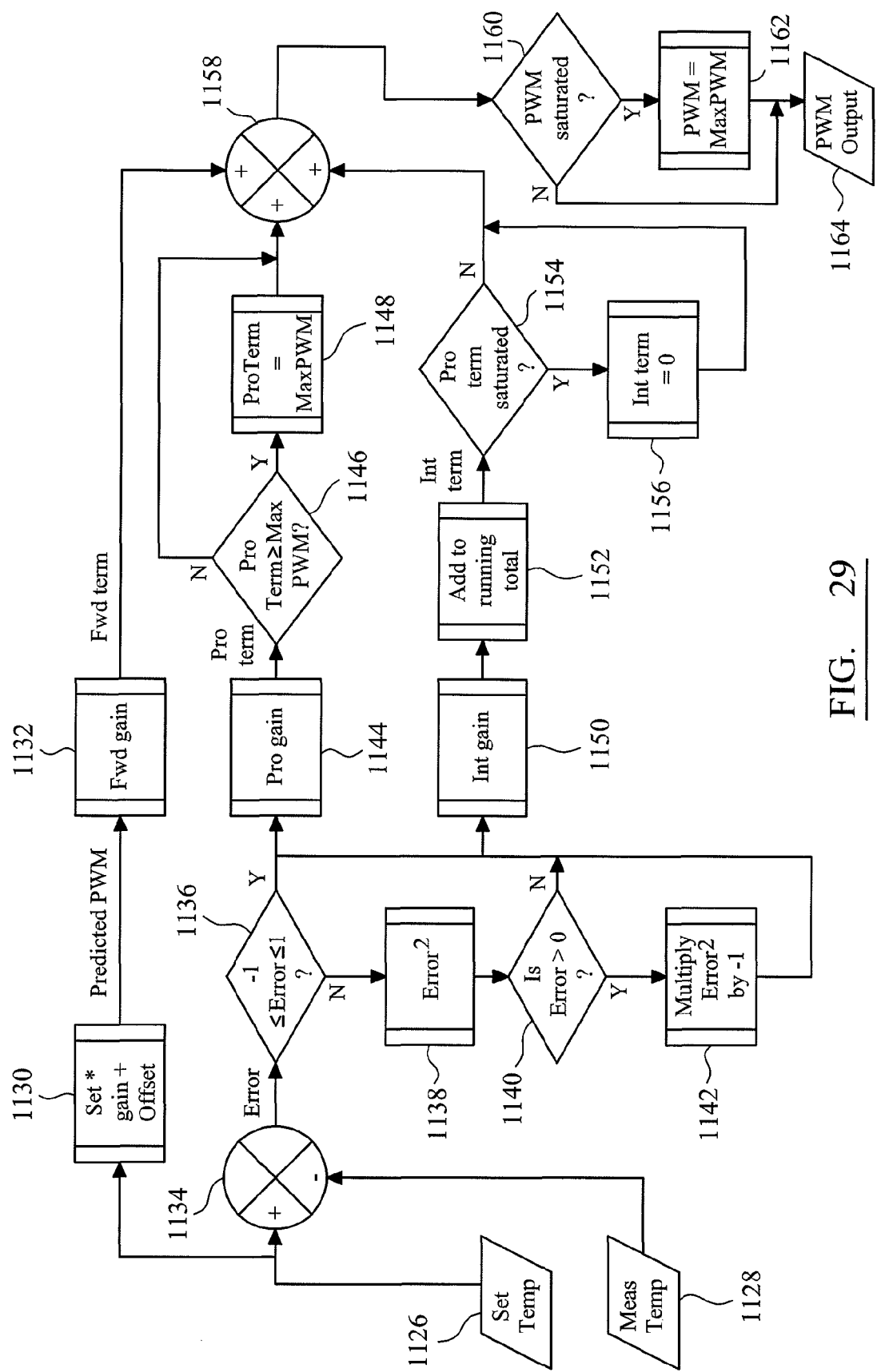
FIG. 29 is a flow chart for temperature of a heater used in the present invention.

The control loop will now be described with reference to FIG. 29. The control loop is provided with inputs of the desired temperature 1126 and the measured temperature 1128 from the temperature sensor. The desired temperature 1126 used in step 1130 to determine the expected steady state PWM value to maintain the desired temperature. The conversion between the desired temperature and the steady state PWM is predetermined based on experimental measurements. The experimental measurements are taken by setting the system to some temperature and allowing it to settle to a steady state. The actual temperature vs. PWM value are captured. This is repeated at several points throughout the operating temperature range. A linear trend line and equation may then be determined for use in step 1130. The equation constants (gain and offset) of this trend line are used in step 1130 to predict what the final PWM will be for any set temperature.

Forward gain is then applied to the predicted final PWM from step 1130 in step 1132. This preferably adjusts the predicted PWM to about 90% of the final PWM result, for example by multiplied by 0.9. Feedback is not required for this term, it helps to ensure that the loop response is immediate and stable.

The control loop also includes proportional and integral terms. Errors between the desired temperature and actual temperature are immediately absorbed by the proportional term for large errors, and transferred over time to the integral term.

The proportional and integral terms are based on the error between the desired temperature 1126 and the measured temperature 1128. The error is calculated by subtracting the measured temperature from the desired temperature in step 1134.

For large errors, it is desired to drive the PWM output to saturation (100% duty cycle) to maximize the temperature slew rate for large temperature changes while maintaining a moderate slew rate for small temperature differences. To achieved this the error is checked whether is it is in the range −1 to 1 in step 1136. If the temperature is outside the range −1 to 1, it is adjusted to maximise slew rate. In that case the error is squared in step 1138. Steps 1140 and 1142 then operate to assign the same sign to the squared result from step 1138 as the original error. Step 1140 determines if the error is less than 0, and if so, step 1142 multiplies the squared error by −1 to restore the negative value. This works to drive the output PWM into saturation for all but small errors, the use of squaring means larger errors have a greater effect. If the absolute value of the error is less than 1, squaring the error works against allowing the integral term to accumulate errors over time, in these cases, the check in step 1136 ensures that the original error is used in the proportional and integral terms.

The proportional term is calculated by applying a gain in step 1144. A check is then made in step 1146 whether the result is greater than a maximum value. The maximum value is the value at which the PWM is saturated. If the result is greater than the maximum value the proportional term is set to the maximum value in step 1148.

The integral tem is calculated by applying a gain in step 1150, this is then added to the running total in step 1152. A check is then made in step 1154 whether the proportional term is saturated (equal to the maximum value as discussed above). If the proportional term is saturated the integral term is set to zero in step 1156. This prevents integral windup, or the effect where Integral term accumulates a large value before the proportional term comes out of saturation.

In step 1158 the forward, proportional and integral terms are added. Another check is then made in step 1160 whether this total value is higher than the maximum value at which the PWM is saturated. If it is, the value is set to the maximum value in step 1162. Finally, at step 1160, the new value for the PWM is output. This value is used until the next temperature measurement is taken and a new value is calculated.

Autofocus Control Method

Autofocus is provided to align the laser with the CE chip capillary accurately. The small diameter of the focussed laser beam and the capillary make it difficult to align an inserted CE chip with the laser without some method of active adjustment.

The mechanical features provided align the CE chip capillary close to the laser, but to improve the alignment, an automatic alignment and focus method is provided. In a first stage of the method, the laser is turned on and the CE chip is moved relative to the laser while monitoring the output of the CCD. The CE chip is moved to scan the laser from one wall to the other of the capillary, and the location of maximum CCD output determined. The CCD output is by reflection or fluorescence from the CE chip and the capillary within it. The CE chip is then moved to the position of the maximum, which corresponds to the correct alignment. Alternatively a particular CCD detection pattern corresponding to the aligned position may be used. In another alternative the position of the walls of the capillary may be detected and the alignment position calculated as the center point between the walls.

Once aligned, the laser is turned on and objective lens is moved while monitoring the output of the CCD for a maximum. The position of the maximum corresponds to the correct focus. Alternatively a particular CCD detection pattern corresponding to the focus position may be used.

The invention claimed is:

1. An apparatus for processing a sample, the apparatus comprising:
   a circuit board; and
   a removable sample cartridge having an inserted state in the apparatus;
   wherein the circuit board has an interface with the removable sample cartridge in the inserted state;

wherein the sample cartridge comprises a working surface defining a plurality of sections for processing a sample;

wherein the circuit board is configured to be adjacent the working surface in the inserted state and comprises:

a plurality of elements, each of the plurality of elements is associated with one of the plurality of sections and is adjacent the associated one of the plurality of sections in the inserted state; and wherein the circuit board further includes at least one alignment feature for engaging a corresponding alignment feature on the removable sample cartridge and ensuring that the plurality of elements are positioned adjacent the associated one of the plurality of sections in the inserted state;

wherein the circuit board further comprises an edge delineating an opening in the circuit board which in the inserted state corresponds to a sample processing chamber on the sample cartridge;

wherein additional components separate from the circuit board are configured for processing in the sample processing chamber; the opening in the circuit board being configured to provide access to the sample processing chamber by the additional components.

2. Apparatus according to claim 1, wherein one or more elements are provided and the elements are selected from the group comprising: a heater for heating the sample cartridge, an electrical contact for powering features on the sample cartridge, an electrical contact for powering a pump on the sample cartridge.

3. Apparatus according to claim 1, wherein the sample cartridge provides a plurality of sections and the circuit board enables these sections to be activated as required for processing the sample by the at least one alignment feature ensuring that the features on the circuit board are aligned correctly with the corresponding features on the sample cartridge in the plurality of sections.

4. Apparatus according to claim 1, wherein the circuit board further defines a window allowing, in use, a feature of the working surface to be visually inspected through the circuit board.

5. Apparatus according to claim 1, wherein the circuit board further comprises projections extending from its surface in a direction such that, in use, they are directed towards the cartridge, the projections being conductive to allow an electrical current to be supplied to the sample cartridge through the projections.

6. Apparatus according to claim 5, wherein the projections are resiliently mounted, so that when a sample cartridge is installed in the apparatus a force is applies to the projections to bias them towards the sample cartridge and improve the electrical contact.

7. Apparatus according to claim 1, wherein at least part of a section of the apparatus for receiving the sample cartridge is be mounted with a resilient element for providing a force to press the circuit board and the working surface of the sample cartridge together in use.

8. Apparatus according to claim 1, wherein a platen is provided by the apparatus, the platen acting against a non-working surface of the sample cartridge and the platen being moved to press the working surface of the sample cartridge against the circuit board.

9. Apparatus according to claim 1, wherein the sample cartridge is placed in a holder before being inserted into the apparatus provided with the circuit board.

* * * * *